(12) United States Patent
Maurer et al.

(10) Patent No.: US 7,129,060 B1
(45) Date of Patent: Oct. 31, 2006

(54) EXPORT SYSTEMS FOR RECOMBINANT PROTEINS

(75) Inventors: Jochen Maurer, Tübingen (DE); Joachim Jose, Tübingen (DE); Thomas F. Meyer, Tübingen (DE)

(73) Assignee: Max-Planck-Gesellschaft zur Forderung der Wissenschaften e.V, Munich (DE)

(*) Notice: Subject to any disclaimer, the term of this patent is extended or adjusted under 35 U.S.C. 154(b) by 0 days.

(21) Appl. No.: 09/147,036

(22) PCT Filed: Mar. 15, 1996

(86) PCT No.: PCT/EP96/01130

§ 371 (c)(1),
(2), (4) Date: Dec. 15, 1998

(87) PCT Pub. No.: WO97/35022

PCT Pub. Date: Sep. 25, 1997

(51) Int. Cl.
*C12P 21/06* (2006.01)
*C12P 21/04* (2006.01)
*C12N 15/00* (2006.01)
*C07H 21/02* (2006.01)
*C07H 21/04* (2006.01)

(52) U.S. Cl. .................... 435/69.1; 425/69.7; 425/71.1; 425/320.1; 536/23.1; 536/23.7; 536/24.1

(58) Field of Classification Search ................ 435/69.1, 435/69.3, 69.7, 7.1, 7.2
See application file for complete search history.

(56) References Cited

U.S. PATENT DOCUMENTS 5,348,867 A * 9/1994 Georgiou et al. .......... 435/69.7

OTHER PUBLICATIONS

Klauser et al, The EMBO Journal, vol. 9, p. 1991-1999, 1990.*
Benz et al, Molecular Microbiology, 1992, 6(11), p. 1539-1546.*
Kozono et al, (Nature, vol. 39, May 1994).*
Benz et al, Molecular Microbiology, 1992, 6(11), 1539-1546.*
Benz et al, Infection and immunity, May 1989, p. 1506-1511.*
Benz et al (Infection and Immunity, May 1989, p. 1506-1511).*
Benz et al (Molecular Microbiology, 1992, 6(11), 1539-1546).*
Maurer et al, 1997, (Journal of Bacteriology, 1997, 794-804).*
Hickman et al (Microbial Pathogenesis, 1991, 11, 19-31).*
Schaffer et al (Biochemie 83, 2001, pp. 591-599).*
Benz et al (Molecular Microbiology, 220, 45(2), p. 267-276).*

* cited by examiner

*Primary Examiner*—Nita Minnifield
*Assistant Examiner*—Vanessa L. Ford
(74) *Attorney, Agent, or Firm*—Rothwell, Figg, Ernst & Manbeck

(57) ABSTRACT

The present invention relates to vectors, host-vector combinations and processes for preparing stable fusion proteins consisting of a carrier protein and a passenger protein, where expression of the fusion proteins leads to exposure of the passenger domains on the surface of bacterial cells, especially *Escherichia coli* cells. If required, the passenger domains can be released into the medium by proteases, for example by selected host factors such as, for example, OmpT.

25 Claims, 27 Drawing Sheets a) *E.coli* UT5600 pBA b) *E.coli* UT5600 pTK1 c) *E.coli* UT5600 pJM7

Fig.6

DNA sequences of the oligonucleotides used

| Name | Use 1) | Length (bp) | Sequence (5'-3') |
|------|--------|-------------|------------------|
| EF16 | PCR (+) | 36 | TGTAAAACGACGGCCAGTATCACGAGGCCCTTTCGT |
| JM1 | PCR (-) | 27 | GGAAGATCTGCCTCAGAAATGAGGGCC |
| JM6 | PCR (-) | 30 | CATGGTACCAGGCGTTTTATTATTCCCTAC |
| JM7 | PCR (+) | 30 | CGGGGTACCCTTAATCCTACAAAAGAAAGT |
| JM20 | PCR (+) | 44 | AAGGGTACCTTTGAAATACTCCGGAGTAATATTTTTGAGGTGTTC |

1)
(+) and (-) relate to the coding (+) and the DNA strand complementary thereto (-).

Fig.7

```
    GCATCCGTGTGGATGAAGATCACTGGAGGAATAAGCTCTGGTAAGCTTAATGACGGGCAA
  1 ------------------------------------------------------------+ 60
    A  S  V  W  M  K  I  T  G  G  I  S  S  G  K  L  N  D  G  Q  -

AATAAAACAACAACCAATCAGTTTATCAATCAGCTCGGGGGGGATATTTATAAATTCCAT
 61 ------------------------------------------------------------+ 120
    N  K  T  T  T  N  Q  F  I  N  Q  L  G  G  D  I  Y  K  F  H  -

GCTGAACAACTGGGTGATTTTACCTTAGGGATTATGGGAGGATACGCGAATGCAAAAGGT
121 ------------------------------------------------------------+ 180
    A  E  Q  L  G  D  F  T  L  G  I  M  G  G  Y  A  N  A  K  G  -

AAAACGATAAATTACACGAGCAACAAAGCTGCCAGAAACACACTGGATGGTTATTCTGTC
181 ------------------------------------------------------------+ 240
    K  T  I  N  Y  T  S  N  K  A  A  R  N  T  L  D  G  Y  S  V  -

GGGGTATACGGTACGTGGTATCAGAATGGGGAAAATGCAACAGGGCTCTTTGCTGAAACT
241 ------------------------------------------------------------+ 300
    G  V  Y  G  T  W  Y  Q  N  G  E  N  A  T  G  L  F  A  E  T  -

TGGATGCAATATAACTGGTTTAATGCATCAGTGAAAGGTGACGGACTGGAAGAAGAAAAA
301 ------------------------------------------------------------+ 360
    W  M  Q  Y  N  W  F  N  A  S  V  K  G  D  G  L  E  E  E  K  -

TATAATCTGAATGGTTTAACCGCTTCTGCAGGTGGGGGATATAACCTGAATGTGCACACA
361 ------------------------------------------------------------+ 420
    Y  N  L  N  G  L  T  A  S  A  G  G  Y  N  L  N  V  H  T  -

TGGACATCACCTGAAGGAATAACAGGTGAATTCTGGTTACAGCCTCATTTGCAGGCTGTC
421 ------------------------------------------------------------+ 480
    W  T  S  P  E  G  I  T  G  E  F  W  L  Q  P  H  L  Q  A  V  -

TGGATGGGGGTTACACCGGATACACATCAGGAGGATAACGGAACGGTGGTGCAGGGAGCA
481 ------------------------------------------------------------+ 540
    W  M  G  V  T  P  D  T  H  Q  E  D  N  G  T  V  V  Q  G  A  -

GGGAAAAATAATATTCAGACAAAAGCAGGTATTCGTGCATCCTGGAAGGTGAAAAGCACC
541 ------------------------------------------------------------+ 600
    G  K  N  N  I  Q  T  K  A  G  I  R  A  S  W  K  V  K  S  T  -

CTGGATAAGGATACCGGGCGGAGGTTCCGTCCGTATATAGAGGCAAACTGGATCCATAAC
601 ------------------------------------------------------------+ 660
    L  D  K  D  T  G  R  R  F  R  P  Y  I  E  A  N  W  I  H  N  -

ACTCATGAATTTGGTGTTAAAATGAGTGATGACAGCCAGTTGTTGTCAGGTAGCCGAAAT
661 ------------------------------------------------------------+ 720
    T  H  E  F  G  V  K  M  S  D  D  S  Q  L  L  S  G  S  R  N  -

CAGGGAGAGATAAAGACAGGTATTGAAGGGGTGATTACTCAAAACTTGTCAGTGAATGGC
721 ------------------------------------------------------------+ 780
    Q  G  E  I  K  T  G  I  E  G  V  I  T  Q  N  L  S  V  N  G  -

GGAGTCGCATATCAGGCAGGAGGTCACGGGAGCAATGCCATCTCCGGAGCACTGGGGATA
781 ------------------------------------------------------------+ 840
    G  V  A  Y  Q  A  G  G  H  G  S  N  A  I  S  G  A  L  G  I  -

AAATACAGCTTC
841 ---------+-- 852
    K  Y  S  F  -
```

Fig.8

```
      CTGCGCCTGCGCGCCGACGCCGGCGGGCCATGGGCGCGTACGTTCAGCGAGCGCCAGCAG
  1   ------------+---------+---------+---------+---------+---------+  60
      L  R  L  R  A  D  A  G  G  P  W  A  R  T  F  S  E  R  Q  Q   -

ATCAGCAACCGCCACGCCCGCGCCTACGACCAGACGGTCAGCGGGCTGGAGATCGGCCTG
 61   ------------+---------+---------+---------+---------+---------+ 120
      I  S  N  R  H  A  R  A  Y  D  Q  T  V  S  G  L  E  I  G  L   -

GACCGTGGCTGGAGCGCGTCGGGCGGGCGCTGGTACGCCGGCGGCCTGCTCGGCTACACC
121   ------------+---------+---------+---------+---------+---------+ 180
      D  R  G  W  S  A  S  G  G  R  W  Y  A  G  G  L  L  G  Y  T   -

TATGCCGACCGCACCTATCCCGGCGACGGTGGCGGCAAGGTCAAGGGCCTGCACGTCGGC
181   ------------+---------+---------+---------+---------+---------+ 240
      Y  A  D  R  T  Y  P  G  D  G  G  G  K  V  K  G  L  H  V  G   -

GGCTACGCCGCCTATGTCGGCGATGGCGGCTACTATCTCGACACCGTGCTGCGGCTGGGC
241   ------------+---------+---------+---------+---------+---------+ 300
      G  Y  A  A  Y  V  G  D  G  G  Y  Y  L  D  T  V  L  R  L  G   -

CGCTACGATCAGCAATACAACATTGCCGGCACCGATGGCGGCCGCGTCACCGCCGACTAC
301   ------------+---------+---------+---------+---------+---------+ 360
      R  Y  D  Q  Q  Y  N  I  A  G  T  D  G  G  R  V  T  A  D  Y   -

CGCACAAGCGGCGCCGCATGGTCGCTCGAAGGCGGGCGCCGGTTCGAGCTGCCCAACGAC
361   ------------+---------+---------+---------+---------+---------+ 420
      R  T  S  G  A  A  W  S  L  E  G  G  R  R  F  E  L  P  N  D   -

TGGTTCGCCGAACCGCAGGCCGAGGTCATGCTGTGGCGCACGTCAGGCAAGCGCTATCGC
421   ------------+---------+---------+---------+---------+---------+ 480
      W  F  A  E  P  Q  A  E  V  M  L  W  R  T  S  G  K  R  Y  R   -

GCCAGCAATGGCCTGCGCGTCAAGGTGGACGCCAACACCGCCACGCTGGGCCGCCTGGGC
481   ------------+---------+---------+---------+---------+---------+ 540
      A  S  N  G  L  R  V  K  V  D  A  N  T  A  T  L  G  R  L  G   -

TTGCGCTTCGGCCGCCGCATCGCCCTGGCCGGCGGCAACATCGTGCAGCCCTACGCCAGG
541   ------------+---------+---------+---------+---------+---------+ 600
      L  R  F  G  R  R  I  A  L  A  G  G  N  I  V  Q  P  Y  A  R   -

CTCGGCTGGACGCAGGAGTTCAAAAGCACGGGCGATGTGCGCACCAATGGCATTGGCCAT
601   ------------+---------+---------+---------+---------+---------+ 660
      L  G  W  T  Q  E  F  K  S  T  G  D  V  R  T  N  G  I  G  H   -

GCCGGCGCAGGCCGCCACGGCCGCGTGGAACTGGGCGCGGGCGTCGACGCCGCGTTGGGC
661   ------------+---------+---------+---------+---------+---------+ 720
      A  G  A  G  R  H  G  R  V  E  L  G  A  G  V  D  A  A  L  G   -

AAGGGGCACAACCTCTATGCTTCGTACGAGTACGCGGCGGGCGACCGGATCAACATTCCG
721   ------------+---------+---------+---------+---------+---------+ 780
      K  G  H  N  L  Y  A  S  Y  E  Y  A  A  G  D  R  I  N  I  P   -

TGGTCGTTCCACGCCGGCTACCGCTACAGCTTC
781   ------------+---------+---------+---- 813
      W  S  F  H  A  G  Y  R  Y  S  F   -
```

Fig. 9

```
     CAAAGCCTGTTCGCATTAGAAGCCGCACTTGAGGTTATTGATGCCCCACAGCAATCGGAA
  1  ---------+---------+---------+---------+---------+---------+  60
     Q  S  L  F  A  L  E  A  A  L  E  V  I  D  A  P  Q  Q  S  E   -

AAAGATCGTCTAGCTCAAGAAGAAGCGGAAAAACAACGCAAACAAAAAGACTTGATCAGC
 61  ---------+---------+---------+---------+---------+---------+ 120
      K  D  R  L  A  Q  E  E  A  E  K  Q  R  K  Q  K  D  L  I  S  -

CGTTATTCAAATAGTGCGTTATCAGAATTATCTGCAACAGTAAATAGTATGCTTTCTGTT
121  ---------+---------+---------+---------+---------+---------+ 180
      R  Y  S  N  S  A  L  S  E  L  S  A  T  V  N  S  M  L  S  V  -

CAAGATGAATTAGATCGTCTTTTTGTAGATCAAGCACAATCTGCCGTGTGGACAAATATC
181  ---------+---------+---------+---------+---------+---------+ 240
     Q  D  E  L  D  R  L  F  V  D  Q  A  Q  S  A  V  W  T  N  I   -

GCACAGGATAAAAGACGCTATGATTCTGATGCGTTCCGTGCTTATCAGCAGCAGAAAACG
241  ---------+---------+---------+---------+---------+---------+ 300
     A  Q  D  K  R  R  Y  D  S  D  A  F  R  A  Y  Q  Q  Q  K  T   -

AACTTACGTCAAATTGGGGTGCAAAAAGCCTTAGCTAATGGACGAATTGGGGCAGTTTTC
301  ---------+---------+---------+---------+---------+---------+ 360
     N  L  R  Q  I  G  V  Q  K  A  L  A  N  G  R  I  G  A  V  F   -

TCGCATAGCCGTTCAGATAATACCTTTGATGAACAGGTTAAAAATCACGCGACATTAACG
361  ---------+---------+---------+---------+---------+---------+ 420
      S  H  S  R  S  D  N  T  F  D  E  Q  V  K  N  H  A  T  L  T  -

ATGATGTCGGGTTTTGCCCAATATCAATGGGGCGATTTACAATTTGGTGTAAACGTGGGA
421  ---------+---------+---------+---------+---------+---------+ 480
     M  M  S  G  F  A  Q  Y  Q  W  G  D  L  Q  F  G  V  N  V  G   -

ACGGGAATCAGTGCGAGTAAAATGGCTGAAGAACAAAGCCGAAAAATTCATCGAAAAGCG
481  ---------+---------+---------+---------+---------+---------+ 540
     T  G  I  S  A  S  K  M  A  E  E  Q  S  R  K  I  H  R  K  A   -

ATAAATTATGGCGTGAATGCAAGTTATCAGTTCCGTTTAGGGCAATTGGGCATTCAGCCT
541  ---------+---------+---------+---------+---------+---------+ 600
     I  N  Y  G  V  N  A  S  Y  Q  F  R  L  G  Q  L  G  I  Q  P   -

TATTTTGGAGTTAATCGCTATTTTATTGAACGTGAAAATTATCAATCTGAGGAAGTGAGA
601  ---------+---------+---------+---------+---------+---------+ 660
     Y  F  G  V  N  R  Y  F  I  E  R  E  N  Y  Q  S  E  E  V  R   -

GTGAAAACGCCTAGCCTTGCATTTAATCGCTATAATGCTGGCATTCGAGTTGATTATACA
661  ---------+---------+---------+---------+---------+---------+ 720
     V  K  T  P  S  L  A  F  N  R  Y  N  A  G  I  R  V  D  Y  T   -

TTTACTCCGACAGATAATATCAGCGTTAAGCCTTATTTCTTCGTCAATTATGTTGATGTT
721  ---------+---------+---------+---------+---------+---------+ 780
     F  T  P  T  D  N  I  S  V  K  P  Y  F  F  V  N  Y  V  D  V   -

TCAAACGCTAACGTACAAACCACGGTAAATCTCACGGTGTTGCAACAACCATTTGGACGT
781  ---------+---------+---------+---------+---------+---------+ 840
     S  N  A  N  V  Q  T  T  V  N  L  T  V  L  Q  Q  P  F  G  R   -

TATTGGCAAAAAGAAGTGGGATTAAAGGCAGAAATTTTACATTTCCAAATTTCCGCTTTT
841  ---------+---------+---------+---------+---------+---------+ 900
     Y  W  Q  K  E  V  G  L  K  A  E  I  L  H  F  Q  I  S  A  F   -

ATCTCAAAATCTCAAGGTTCACAACTCGGCAAACAGCAAAATGTGGGCGTGAAATTGGGC
901  ---------+---------+---------+---------+---------+---------+ 960
     I  S  K  S  Q  G  S  Q  L  G  K  Q  Q  N  V  G  V  K  L  G   -

TATCGTTGG
961  --------- 969
     Y  R  W   -
```

Figure 10

```
      ACCTCAATCTACACCACAGTACAGGCAGGATGGGATCATGTATTTGGCAGCGAGGGTGGA
  1   ---------+---------+---------+---------+---------+---------+  60
      T  S  I  Y  T  T  V  Q  A  G  W  D  H  V  F  G  S  E  G  G   -

AATGACTTTTTAGGTTTTGCTGTGGCTTATGCAGGTGCAGCGATGAGCTCTGAGAAGAAA
 61   ---------+---------+---------+---------+---------+---------+ 120
      N  D  F  L  G  F  A  V  A  Y  A  G  A  A  M  S  S  E  K  K   -

GAACAGCTAGTAAATGGTGCACAAAAGGGAGTAAAATCCAGCGGTGGAAATGCCTTTGAA
121   ---------+---------+---------+---------+---------+---------+ 180
      E  Q  L  V  N  G  A  Q  K  G  V  K  S  S  G  G  N  A  F  E   -

ATCTCGCTCTACAACTCCTATGTACAAGATGGTGCTGCTTCTAGCACAGATTTCAAGTAT
181   ---------+---------+---------+---------+---------+---------+ 240
      I  S  L  Y  N  S  Y  V  Q  D  G  A  A  S  S  T  D  F  K  Y   -

GGTTTTTATAGTGATAGCGTGGCAAAATTCAGCTTCTTGTGGAACAAGCTTACAATGTTT
241   ---------+---------+---------+---------+---------+---------+ 300
      G  F  Y  S  D  S  V  A  K  F  S  F  L  W  N  K  L  T  M  F   -

GGTGAGGACAGCTCTCCTAACATGCAAAACTTTGGTTTCACCTTCTCTCAAGAGATTGGT
301   ---------+---------+---------+---------+---------+---------+ 360
      G  E  D  S  S  P  N  M  Q  N  F  G  F  T  F  S  Q  E  I  G   -

TATCGCTTCTTGCTAGGAAATCACAACGAGTGGTATATCACTCCACAAGGGCAAGTTGCT
361   ---------+---------+---------+---------+---------+---------+ 420
      Y  R  F  L  L  G  N  H  N  E  W  Y  I  T  P  Q  G  Q  V  A   -

TTAGGTTATTTCAACCAAAGCAATATCAAGCAAACCCTAGGAAGCCACTGGCTAAAAGGC
421   ---------+---------+---------+---------+---------+---------+ 480
      L  G  Y  F  N  Q  S  N  I  K  Q  T  L  G  S  H  W  L  K  G   -

GAGCAAAGTTCTATCTTCACAGTGCAGGGGCGAATTGGAAGCAACTTTGGTTATAGATTT
481   ---------+---------+---------+---------+---------+---------+ 540
      E  Q  S  S  I  F  T  V  Q  G  R  I  G  S  N  F  G  Y  R  F   -

AATCAATTCACTGAAGACAAGGGCTGGGCTTCAGAGCTTTATTTGGGCTTGTGGTACATC
541   ---------+---------+---------+---------+---------+---------+ 600
      N  Q  F  T  E  D  K  G  W  A  S  E  L  Y  L  G  L  W  Y  I   -

GGCGATTATATCAGTGGTGGCAATCTTACCCTCGTGTCTGACCTAGGTTCTGTAAACACT
601   ---------+---------+---------+---------+---------+---------+ 660
      G  D  Y  I  S  G  G  N  L  T  L  V  S  D  L  G  S  V  N  T   -

TTAAGGACTTTGAGCTCTACTGGTAGATTTGCCTTTAACATTGGTACAAACTTCGTCGTC
661   ---------+---------+---------+---------+---------+---------+ 720
      L  R  T  L  S  S  T  G  R  F  A  F  N  I  G  T  N  F  V  V   -

AAAGATAATCATAGATTCTACTTTGATTTTGAAAGAAGCTTTGGAGGCAAAATCATCACA
721   ---------+---------+---------+---------+---------+---------+ 780
      K  D  N  H  R  F  Y  F  D  F  E  R  S  F  G  G  K  I  I  T   -

GATTACCAATTCAACATTGGCTATCGCTATAACTTTGGCGAAAACAGAAAATACGTTTCT
781   ---------+---------+---------+---------+---------+---------+ 840
      D  Y  Q  F  N  I  G  Y  R  Y  N  F  G  E  N  R  K  Y  V  S   -

CTTCTTGCAGGTAGTATGAAAGACACTATCAAAAAAGATGATAAGAAAGAAAACAAAGAA
841   ---------+---------+---------+---------+---------+---------+ 900
      L  L  A  G  S  M  K  D  T  I  K  K  D  D  K  K  E  N  K  E   -

GAGACAGAAGAAATTGAG
901   ---------+-------- 918
      E  T  E  E  I  E   -
```

Figure 11

```
        GAAACCACCATGTGGATTCGTACTGTTGGTGGACATAATGAGCATAATTTAGCTGATAGA
   1    ----------+----------+----------+----------+----------+----------+  60
        E  T  T  M  W  I  R  T  V  G  G  H  N  E  H  N  L  A  D  R   -

CAATTAAAAACCACAGCTAACAGGATGGTTTATCAGATTGGTGGAGATATTTTGAAGACA
   61   ----------+----------+----------+----------+----------+----------+  120
        Q  L  K  T  T  A  N  R  M  V  Y  Q  I  G  G  D  I  L  K  T   -

AACTTCACTGATCATGATGGCTTGCATGTGGGTATTATGGGAGCTTATGGATATCAGGAT
   121  ----------+----------+----------+----------+----------+----------+  180
        N  F  T  D  H  D  G  L  H  V  G  I  M  G  A  Y  G  Y  Q  D   -

AGCAAAACTCATAATAAGTATACTAGTTATAGTTCACGAGGAACTGTGAGCGGTTATACT
   181  ----------+----------+----------+----------+----------+----------+  240
        S  K  T  H  N  K  Y  T  S  Y  S  S  R  G  T  V  S  G  Y  T   -

GCCGGTTTGTACAGTTCTTGGTTTCAGGATGAAAAAGAACGAACAGGTCTATATATGGAT
   241  ----------+----------+----------+----------+----------+----------+  300
        A  G  L  Y  S  S  -W  F  Q  D  E  K  E  R  T  G  L  Y  M  D   -

GCTTGGTTGCAGTACAGTTGGTTTAATAATACAGTCAAAGGAGATGGGTTAACTGGTGAG
   301  ----------+----------+----------+----------+----------+----------+  360
        A  W  L  Q  Y  S  W  F  N  N  T  V  K  G  D  G  L  T  G  E   -

AAATATTCCAGCAAAGGAATAACAGGAGCTTTGGAAGCTGGCTATATCTACCCAACCATA
   361  ----------+----------+----------+----------+----------+----------+  420
        K  Y  S  S  K  G  I  T  G  A  L  E  A  G  Y  I  Y  P  T  I   -

CGCTGGACTGCTCATAATAATATTGACAACGCATTGTATCTCAATCCACAAGTCCAGATA
   421  ----------+----------+----------+----------+----------+----------+  480
        R  W  T  A  H  N  N  I  D  N  A  L  Y  L  N  P  Q  V  Q  I   -

ACTAGGCATGGGGTAAAAGCAAACGACTATATTGAACACAATGGCACTATGGTCACATCC
   481  ----------+----------+----------+----------+----------+----------+  540
        T  R  H  G  V  K  A  N  D  Y  I  E  H  N  G  T  M  V  T  S   -

TCTGGGGGCAATAATATTCAAGCAAAATTGGGATTGCGTACATCCTTAATTAGTCAGAGT
   541  ----------+----------+----------+----------+----------+----------+  600
        S  G  G  N  N  I  Q  A  K  L  G  L  R  T  S  L  I  S  Q  S   -

TGTATCGATAAGGAGACTCTTCGTAAGTTCGAACCATTTTTGGAAGTGAATTGGAAATGG
   601  ----------+----------+----------+----------+----------+----------+  660
        C  I  D  K  E  T  L  R  K  F  E  P  F  L  E  V  N  W  K  W   -

AGCTCAAAGCAATATGGTGTAATTATGAATGGCATGTCAAATCACCAGATAGGCAACCGT
   661  ----------+----------+----------+----------+----------+----------+  720
        S  S  K  Q  Y  G  V  I  M  N  G  M  S  N  H  Q  I  G  N  R   -

AATGTGATTGAACTCAAAACTGGTGTGGGGGGCGTCTTGCAGATAACCTAAGCATCTGG
   721  ----------+----------+----------+----------+----------+----------+  780
        N  V  I  E  L  K  T  G  V  G  G  R  L  A  D  N  L  S  I  W   -

GGAAACGTATCTCAGCAATTGGGTAATAACAGTTACAGAGACACCCAAGGTATTTTGGGT
   781  ----------+----------+----------+----------+----------+----------+  840
        G  N  V  S  Q  Q  L  G  N  N  S  Y  R  D  T  Q  G  I  L  G   -

GTGAAATATACCTTC
   841  ----------+-----  855
        V  K  Y  T  F   -
```

Fig. 12

```
     CTGGGCGAGTTGCGCCTGAATCCGGACGCCGGCGGCGCCTGGGGCCGCGGCTTCGCGCAA
  1  ---------+---------+---------+---------+---------+---------+ 60
     L  G  E  L  R  L  N  P  D  A  G  G  A  W  G  R  G  F  A  Q  -

CGCCAGCAGCTGGACAACCGCGCCGGGCGGCGCTTCGACCAGAAGGTGGCCGGCTTCGAG
 61  ---------+---------+---------+---------+---------+---------+ 120
     R  Q  Q  L  D  N  R  A  G  R  R  F  D  Q  K  V  A  G  F  E  -

CTGGGCGCCGACCACGCGGTGGCGGTGGCCGGCGGACGCTGGCACCTGGGCGGGCTGGCC
121  ---------+---------+---------+---------+---------+---------+ 180
     L  G  A  D  H  A  V  A  V  A  G  G  R  W  H  L  G  G  L  A  -

GGCTATACGCGCGGCGACCGCGGCTTCACCGGCGACGGCGGCGGCCACACCGACAGCGTG
181  ---------+---------+---------+---------+---------+---------+ 240
     G  Y  T  R  G  D  R  G  F  T  G  D  G  G  G  H  T  D  S  V  -

CATGTCGGGGGCTATGCCACATATATCGCCGACAGCGGTTTCTACCTGGACGCGACGCTG
241  ---------+---------+---------+---------+---------+---------+ 300
     H  V  G  G  Y  A  T  Y  I  A  D  S  G  F  Y  L  D  A  T  L  -

CGCGCCAGCCGCCTGGAGAATGACTTCAAGGTGGCGGGCAGCGACGGGTACGCGGTCAAG
301  ---------+---------+---------+---------+---------+---------+ 360
     R  A  S  R  L  E  N  D  F  K  V  A  G  S  D  G  Y  A  V  K  -

GGCAAGTACCGCACCCATGGGGTGGGCGCCTCGCTCGAGGCGGGCCGGCGCTTTACCCAT
361  ---------+---------+---------+---------+---------+---------+ 420
     G  K  Y  R  T  H  G  V  G  A  S  L  E  A  G  R  R  F  T  H  -

GCCGACGGCTGGTTCCTCGAGCCGCAGGCCGAGCTGGCGGTATTCCGGGCCGGCGGCGGT
421  ---------+---------+---------+---------+---------+---------+ 480
     A  D  G  W  F  L  E  P  Q  A  E  L  A  V  F  R  A  G  G  G  -

GCGTACCGCGCGGCCAACGGCCTGCGGGTGCGCGACGAAGGCGGCAGCTCGGTGCTGGGT
481  ---------+---------+---------+---------+---------+---------+ 540
     A  Y  R  A  A  N  G  L  R  V  R  D  E  G  G  S  S  V  L  G  -

CGCCTGGGCCTGGAGGTCGGCAAGCGCATCGAACTGGCAGGCGGCAGGCAGGTGCAGCCA
541  ---------+---------+---------+---------+---------+---------+ 600
     R  L  G  L  E  V  G  K  R  I  E  L  A  G  G  R  Q  V  Q  P  -

TACATCAAGGCCAGCGTGCTGCAGGAGTTCGACGGCGCGGGTACGGTACACACCAACGGC
601  ---------+---------+---------+---------+---------+---------+ 660
     Y  I  K  A  S  V  L  Q  E  F  D  G  A  G  T  V  H  T  N  G  -

ATCGCGCACCGCACCGAACTGCGCGGCACGCGCGCCGAACTGGGCCTGGGCATGGCCGCC
661  ---------+---------+---------+---------+---------+---------+ 720
     I  A  H  R  T  E  L  R  G  T  R  A  E  L  G  L  G  M  A  A  -

GCGCTGGGCCGCGGCCACAGCCTGTATGCCTCGTACGAGTACTCCAAGGGCCCGAAGCTG
721  ---------+---------+---------+---------+---------+---------+ 780
     A  L  G  R  G  H  S  L  Y  A  S  Y  E  Y  S  K  G  P  K  L  -

GCCATGCCGTGGACCTTCCACGCGGGCTACCGGTACAGCTGG
781  ---------+---------+---------+---------+-- 822
     A  M  P  W  T  F  H  A  G  Y  R  Y  S  W  -
```

Fig. 13

```
      CTGGGCGAGTTGCGCCTGAATCCGGACGCCGGCGGCGCTTGGGCCGCGGCTTCGCGCAA
  1   ------------+---------+---------+---------+---------+---------+  60
       L  G  E  L  R  L  N  P  D  A  G  G  A  W  G  R  G  F  A  Q   -

CGCCAGCAACTGGACAACCGCGCCGGGCGGCGCTTCGACCAGAAGGTGGCCGGCTTCGAG
 61   ------------+---------+---------+---------+---------+---------+ 120
       R  Q  Q  L  D  N  R  A  G  R  R  F  D  Q  K  V  A  G  F  E   -

CTGGGCGCCGACCACGCGGTGGCGGTGGCCGGCGGGCGCTGGCACCTGGGCGGGCTGGCC
121   ------------+---------+---------+---------+---------+---------+ 180
       L  G  A  D  H  A  V  A  V  A  G  G  R  W  H  L  G  G  L  A   -

GGCTATACGCGCGGCGACCGCGGCTTTACCGGCGACGGCGGCGGCCACACCGACAGCGTG
181   ------------+---------+---------+---------+---------+---------+ 240
       G  Y  T  R  G  D  R  G  F  T  G  D  G  G  H  T  D  S  V   -

CATGTCGGGGGCTATGCCACCTATATCGCCAACAGCGGTTTCTACCTGGACGCGACGCTG
241   ------------+---------+---------+---------+---------+---------+ 300
       H  V  G  G  Y  A  T  Y  I  A  N  S  G  F  Y  L  D  A  T  L   -

CGCGCCAGCCGCCTCGAAAATGACTTCAAGGTGGCGGGCAGCGATGGGTACGCGGTCAAG
301   ------------+---------+---------+---------+---------+---------+ 360
       R  A  S  R  L  E  N  D  F  K  V  A  G  S  D  G  Y  A  V  K   -

GGCAAGTACCGCACCCATGGGGTAGGCGTCTCGCTCGAGGCGGGCCGGCGCTTCGCCCAT
361   ------------+---------+---------+---------+---------+---------+ 420
       G  K  Y  R  T  H  G  V  G  V  S  L  E  A  G  R  R  F  A  H   -

GCCGACGGCTGGTTCCTCGAGCCGCAGGCCGAGCTGGCGGTGTTCCGGGTCGGCGGCGGT
421   ------------+---------+---------+---------+---------+---------+ 480
       A  D  G  W  F  L  E  P  Q  A  E  L  A  V  F  R  V  G  G   -

GCGTACCGCGCGGCCAATGGCCTGCGGGTGCGCGACGAAGGCGGCAGCTCGGTGCTGGGT
481   ------------+---------+---------+---------+---------+---------+ 540
       A  Y  R  A  A  N  G  L  R  V  R  D  E  G  G  S  S  V  L  G   -

CGCCTGGGCCTGGAGGTCGGCAAGCGCATCGAACTGGCAGGCGGCAGGCAGGTGCAGCCA
541   ------------+---------+---------+---------+---------+---------+ 600
       R  L  G  L  E  V  G  K  R  I  E  L  A  G  G  R  Q  V  Q  P   -

TACATCAAGGCCAGCGTGTTGCAGGAGTTCGACGGCGCGGGTACGGTACGCACCAACGGC
601   ------------+---------+---------+---------+---------+---------+ 660
       Y  I  K  A  S  V  L  Q  E  F  D  G  A  G  T  V  R  T  N  G   -

ATCGCGCATCGCACCGAACTGCGCGGCACGCGCGCCGAACTGGGCCTGGGCATGGCCGCC
661   ------------+---------+---------+---------+---------+---------+ 720
       I  A  H  R  T  E  L  R  G  T  R  A  E  L  G  L  G  M  A  A   -

GCGCTGGGCCGCGGCCACAGCCTGTATGCCTCGTACGAGTACTCCAAGGGCCCGAAGCTG
721   ------------+---------+---------+---------+---------+---------+ 780
       A  L  G  R  G  H  S  L  Y  A  S  Y  E  Y  S  K  G  P  K  L   -

GCCATGCCGTGGACCTTCCACGCGGGCTACCGGTACAGCTGG
781   ------------+---------+---------+---------+--- 822
       A  M  P  W  T  F  H  A  G  Y  R  Y  S  W   -
```

Fig.14

```
     AAGTTTGGTGCGTGGATAAGCCCGTTTGTCGGTAATGCAACGCAGAAGATGTGTAACAGT
  1  ------------+---------+---------+---------+---------+---------+ 60
     K  F  G  A  W  I  S  P  F  V  G  N  A  T  Q  K  M  C  N  S  -

ATAAGTGGTTATAAGTCTGATACAACTGGTGGCACTATAGGTTTTGACGGCTTCGTTAGC
 61  ------------+---------+---------+---------+---------+---------+ 120
     I  S  G  Y  K  S  D  T  T  G  G  T  I  G  F  D  G  F  V  S  -

GATGATCTAGCACTCGGACTTGCATATACAAGAGCCGATACTGACATTAAGCTAAAAAAT
121  ------------+---------+---------+---------+---------+---------+ 180
     D  D  L  A  L  G  L  A  Y  T  R  A  D  T  D  I  K  L  K  N  -

AATAAAACGGGCGATAAGAATAAGGTAGAGAGCAACATCTATTCTTTATACGGTTTATAT
181  ------------+---------+---------+---------+---------+---------+ 240
     N  K  T  G  D  K  N  K  V  E  S  N  I  Y  S  L  Y  G  L  Y  -

AATGTACCTTATGAAAATCTCTTCGTTGAAGCTATAGCATCTTACTCAGATAATAAGATA
241  ------------+---------+---------+---------+---------+---------+ 300
     N  V  P  Y  E  N  L  F  V  E  A  I  A  S  Y  S  D  N  K  I  -

AGAAGCAAATCAAGACGTGTTATTGCAACGACACTAGAGACTGTCGGTTATCAAACTGCA
301  ------------+---------+---------+---------+---------+---------+ 360
     R  S  K  S  R  R  V  I  A  T  T  L  E  T  V  G  Y  Q  T  A  -

AACGGTAAGTATAAATCCGAAAGCTATACAGGTCAGTTAATGGCTGGTTATACCTATATG
361  ------------+---------+---------+---------+---------+---------+ 420
     N  G  K  Y  K  S  E  S  Y  T  G  Q  L  M  A  G  Y  T  Y  M  -

ATGCCTGAGAACATTAACTTAACACCGCTAGCTGGGCTTAGATATTCGACTATCAAAGAT
421  ------------+---------+---------+---------+---------+---------+ 480
     M  P  E  N  I  N  L  T  P  L  A  G  L  R  Y  S  T  I  K  D  -

AAGGGCTATAAGGAAACCGGTACTACTTACCAAAATCTTACCGTTAAAGGCAAGAACTAT
481  ------------+---------+---------+---------+---------+---------+ 540
     K  G  Y  K  E  T  G  T  T  Y  Q  N  L  T  V  K  G  K  N  Y  -

AATACTTTCGACGGTTTACTCGGTGCTAAAGTATCAAGTAATATCAATGTCAATGAAATA
541  ------------+---------+---------+---------+---------+---------+ 600
     N  T  F  D  G  L  L  G  A  K  V  S  S  N  I  N  V  N  E  I  -

GTGCTAACACCTGAGCTTTACGCAATGGTCGATTATGCATTCAAGAATAAAGTTTCGGCG
601  ------------+---------+---------+---------+---------+---------+ 660
     V  L  T  P  E  L  Y  A  M  V  D  Y  A  F  K  N  K  V  S  A  -

ATTGATGCAAGGTTACAAGGTATGACTGCTCCTCTTCCAACCAACAGCTTTAAGCAAAGC
661  ------------+---------+---------+---------+---------+---------+ 720
     I  D  A  R  L  Q  G  M  T  A  P  L  P  T  N  S  F  K  Q  S  -

AAAACAAGTTTTGATGTCGGTGTCGGTGTTACTGCTAAGCATAAAATGATGGAATACAGG
721  ------------+---------+---------+---------+---------+---------+ 780
     K  T  S  F  D  V  G  V  G  V  T  A  K  H  K  M  M  E  Y  R  -

ATTAACTACGATACCAATATCGGAAGTAAGTATTTCGCTCAGCAAGGTAGTGTAAAAGTT
781  ------------+---------+---------+---------+---------+---------+ 840
     I  N  Y  D  T  N  I  G  S  K  Y  F  A  Q  Q  G  S  V  K  V  -

CGTGTTAATTTT
841  ---------+-- 852
     R  V  N  F  -
```

Fig. 15

```
    TCTTATGGTGTATGGGCTAAACCTTTCTATAACATTGCAGAACAAGACAAAAAAGGTGGT
  1 ---------+---------+---------+---------+---------+---------+ 60
    S  Y  G  V  W  A  K  P  F  Y  N  I  A  E  Q  D  K  K  G  G  -

ATAGCTGGTTATAAAGCAAAAACTACTGGGGTTGTAGTTGGTTTAGATACTCTCGCTAGC
 61 ---------+---------+---------+---------+---------+---------+ 120
    I  A  G  Y  K  A  K  T  T  G  V  V  V  G  L  D  T  L  A  S  -

GATAACCTAATGATTGGGGCAGCTATTGGGATCACTAAAACTGATATAAAACACCAAGAT
121 ---------+---------+---------+---------+---------+---------+ 180
    D  N  L  M  I  G  A  A  I  G  I  T  K  T  D  I  K  H  Q  D  -

TATAAGAAAGGTGATAAAACTGATATTAATGGTTTATCATTCTCTCTATATGGTTCCCAA
181 ---------+---------+---------+---------+---------+---------+ 240
    Y  K  K  G  D  K  T  D  I  N  G  L  S  F  S  L  Y  G  S  Q  -

CAGCTTGTTAAGAATTTCTTTGCTCAAGGTAATTCAATCTTTACCTTAAACAAAGTCAAA
241 ---------+---------+---------+---------+---------+---------+ 300
    Q  L  V  K  N  F  F  A  Q  G  N  S  I  F  T  L  N  K  V  K  -

AGTAAAAGTCAGCGTTACTTCTTCGAGTCTAATGGTAAGATGAGCAAGCAAATTGCTGCT
301 ---------+---------+---------+---------+---------+---------+ 360
    S  K  S  Q  R  Y  F  F  E  S  N  G  K  M  S  K  Q  I  A  A  -

GGTAATTACGATAACATGACATTTGGTGGTAATTTAATATTTGGTTATGATTATAATGCA
361 ---------+---------+---------+---------+---------+---------+ 420
    G  N  Y  D  N  M  T  F  G  G  N  L  I  F  G  Y  D  Y  N  A  -

ATGCCAAATGTATTAGTAACTCCAATGGCAGGACTTAGCTACTTAAAATCTTCTAATGAA
421 ---------+---------+---------+---------+---------+---------+ 480
    M  P  N  V  L  V  T  P  M  A  G  L  S  Y  L  K  S  S  N  E  -

AATTATAAAGAAACCGGTACAACAGTTGCAAATAAGCGCATTAATAGCAAATTTAGTGAT
481 ---------+---------+---------+---------+---------+---------+ 540
    N  Y  K  E  T  G  T  T  V  A  N  K  R  I  N  S  K  F  S  D  -

AGAGTCGATTTAATAGTAGGGGCTAAAGTAGCTGGTAGTACTGTGAATATAACTGATATT
541 ---------+---------+---------+---------+---------+---------+ 600
    R  V  D  L  I  V  G  A  K  V  A  G  S  T  V  N  I  T  D  I  -

GTGATATATCCGGAAATTCATTCTTTTGTGGTGCACAAAGTAAATGGTAAATTATCTAAC
601 ---------+---------+---------+---------+---------+---------+ 660
    V  I  Y  P  E  I  H  S  F  V  V  H  K  V  N  G  K  L  S  N  -

TCTCAGTCTATGTTAGATGGACAAACTGCTCCATTTATCAGTCAACCTGATAGAACTGCT
661 ---------+---------+---------+---------+---------+---------+ 720
    S  Q  S  M  L  D  G  Q  T  A  P  F  I  S  Q  P  D  R  T  A  -

AAAACGTCTTATAATATAGGCTTAAGTGCAAACATAAAATCTGATGCTAAGATGGAGTAT
721 ---------+---------+---------+---------+---------+---------+ 780
    K  T  S  Y  N  I  G  L  S  A  N  I  K  S  D  A  K  M  E  Y  -

GGTATCGGTTATGATTTTAATTCTGCAAGTAAATATACTGCACATGAAGGTACTTTAAAA
781 ---------+---------+---------+---------+---------+---------+ 840
    G  I  G  Y  D  F  N  S  A  S  K  Y  T  A  H  Q  G  T  L  K  -

GTACGTGTAAACTTC
841 ---------+----- 855
    V  R  V  N  F  -
```

Fig.16

```
    GCTTACGGTATATGGGCAAAACCTTTCTATACTGATGCACATCAAAGTAAGAAAGGTGGT
1   ------------+---------+---------+---------+---------+---------+ 60
    A  Y  G  I  W  A  K  P  F  Y  T  D  A  H  Q  S  K  K  G  G   -

TTAGCTGGTTATAAAGCTAAAACCACCGGTGTCGTAATCGGTTTAGATACGCTAGCTAAC
61  ------------+---------+---------+---------+---------+---------+ 120
    L  A  G  Y  K  A  K  T  T  G  V  V  I  G  L  D  T  L  A  N   -

GATAATTTAATGATCGGTGCTGCTATCGGTATCACTAAAACTGATATAAAACATCAAGAT
121 ------------+---------+---------+---------+---------+---------+ 180
    D  N  L  M  I  G  A  A  I  G  I  T  K  T  D  I  K  H  Q  D   -

TATAAGAAAGGTGATAAAACCGACGTTAACGGTTTCTCATTCTCTCTATATGGTGCCCAG
181 ------------+---------+---------+---------+---------+---------+ 240
    Y  K  K  G  D  K  T  D  V  N  G  F  S  F  S  L  Y  G  A  Q   -

CAGCTTGTTAAGAACTTCTTTGCTCAAGGTAGTGCAATATTTAGCTTAAACCAAGTGAAG
241 ------------+---------+---------+---------+---------+---------+ 300
    Q  L  V  K  N  F  F  A  Q  G  S  A  I  F  S  L  N  Q  V  K   -

AACAAAAGTCAGCGTTACTTCTTCGATGCTAACGGTAATATGAGCAAGCAAATTGCTGCC
301 ------------+---------+---------+---------+---------+---------+ 360
    N  K  S  Q  R  Y  F  F  D  A  N  G  N  M  S  K  Q  I  A  A   -

GGTCATTACGATAACATGACATTTGGTGGTAACTTAACAGTCGGTTATGATTACAATGCA
361 ------------+---------+---------+---------+---------+---------+ 420
    G  H  Y  D  N  M  T  F  G  G  N  L  T  V  G  Y  D  Y  N  A   -

ATGCAAGGTGTGTTAGTAACTCCAATGGCAGGACTTAGCTACTTAAAGTCTTCTGACGAA
421 ------------+---------+---------+---------+---------+---------+ 480
    M  Q  G  V  L  V  T  P  M  A  G  L  S  Y  L  K  S  S  D  E   -

AACTACAAAGAAACCGGTACAACAGTTGCAAACAAGCAAGTTAACAGCAAATTTAGCGAT
481 ------------+---------+---------+---------+---------+---------+ 540
    N  Y  K  E  T  G  T  T  V  A  N  K  Q  V  N  S  K  F  S  D   -

AGAACCGATTTAATAGTAGGTGCTAAAGTAGCCGGCAGTACTATGAACATAACTGATCTT
541 ------------+---------+---------+---------+---------+---------+ 600
    R  T  D  L  I  V  G  A  K  V  A  G  S  T  M  N  I  T  D  L   -

GCGGTATATCCAGAAGTTCACGCTTTTGTGGTTCACAAAGTAACCGGTAGATTATCTAAA
601 ------------+---------+---------+---------+---------+---------+ 660
    A  V  Y  P  E  V  H  A  F  V  V  H  K  V  T  G  R  L  S  K   -

ACTCAGTCTGTATTAGACGGACAAGTTACTCCGTGTATCAACCAGCCTGACAGAACCACT
661 ------------+---------+---------+---------+---------+---------+ 720
    T  Q  S  V  L  D  G  Q  V  T  P  C  I  N  Q  P  D  R  T  T   -

AAAACATCTTATAATTTAGGTTTAAGTGCAAGCATAAGATCTGATGCTAAGATGGAGTAC
721 ------------+---------+---------+---------+---------+---------+ 780
    K  T  S  Y  N  L  G  L  S  A  S  I  R  S  D  A  K  M  E  Y   -

GGAATCGGTTACGATGCTCAGATTTCAAGTAAATATACTGCACATCAAGGTACTCTAAAA
781 ------------+---------+---------+---------+---------+---------+ 840
    G  I  G  Y  D  A  Q  I  S  S  K  Y  T  A  H  Q  G  T  L  K   -

GTCCGTGTAAACTTC
841 ------------+----- 855
    V  R  V  N  F   -
```

Fig. 17

```
     TCTTATGGTGTATGGGCTAAACCTTTCTATAACATCGCAGAACAAGATAAAAAAGGTGGT
  1  ------------------------------------------------------------  60
      S  Y  G  V  W  A  K  P  F  Y  N  I  A  E  Q  D  K  K  G  G  -

CTAGCTGGTTATAAAGCAAAAACTGCTGGTGTTGTAGTTGGTTTAGATACTCTCGCTAAT
 61  ------------------------------------------------------------ 120
      L  A  G  Y  K  A  K  T  A  G  V  V  V  G  L  D  T  L  A  N  -

GATAACCTAATGATTGGTGCAGCTATTGGTATCACTAAAACTGACATAAAACACCAAGAT
121  ------------------------------------------------------------ 180
      D  N  L  M  I  G  A  A  I  G  I  T  K  T  D  I  K  H  Q  D  -

TATAAAAAGGTGATAAAACTGATATTAAGGGTTTATCCTTCTCTCTATATGGTGCCCAG
181  ------------------------------------------------------------ 240
      Y  K  K  G  D  K  T  D  I  K  G  L  S  F  S  L  Y  G  A  Q  -

CAGCTTGTTAAGAATTTCTTTGCTCAAGGTAGTGCAATATTTACCTTAAACAAAGTCAAA
241  ------------------------------------------------------------ 300
      Q  L  V  K  N  F  F  A  Q  G  S  A  I  F  T  L  N  K  V  K  -

AGTAAAAGTCAGCGTTACTTCTTCGATGCTAATGGTAAGATGAACAAGCAAATTGCTGCC
301  ------------------------------------------------------------ 360
      S  K  S  Q  R  Y  F  F  D  A  N  G  K  M  N  K  Q  I  A  A  -

GGTAATTATGATAACATAACATTCGGTGGTAATTTAATGTTTGGTTATGATTATAATGCA
361  ------------------------------------------------------------ 420
      G  N  Y  D  N  I  T  F  G  G  N  L  M  F  G  Y  D  Y  N  A  -

CTGCAAGGTGTATTAGTGACTCCAATGGCAGGGCTTAGCTACTTAAAATCTTCTAATGAA
421  ------------------------------------------------------------ 480
      L  Q  G  V  L  V  T  P  M  A  G  L  S  Y  L  K  S  S  N  E  -

AACTATAAAGAAACTGGTACTACAGTTGCAAATAAGCGCATTCACAGCAAATTTAGTGAT
481  ------------------------------------------------------------ 540
      N  Y  K  E  T  G  T  T  V  A  N  K  R  I  H  S  K  F  S  D  -

AGAATCGATTTAATAGTAGGTGCTAAAGTAACTGGTAGTGCTATGAATATAAATGATATT
541  ------------------------------------------------------------ 600
      R  I  D  L  I  V  G  A  K  V  T  G  S  A  M  N  I  N  D  I  -

GTGATATATCCAGAAATTCATTCTTTTGTAGTGCACAAAGTAAATGGTAAGCTATCTAAG
601  ------------------------------------------------------------ 660
      V  I  Y  P  E  I  H  S  F  V  V  H  K  V  N  G  K  L  S  K  -

GCTCAGTCTATGTTAGATGGACAAACTGCTCCATTTATCAGTCAGCCTGATAGAACTGCT
661  ------------------------------------------------------------ 720
      A  Q  S  M  L  D  G  Q  T  A  P  F  I  S  Q  P  D  R  T  A  -

AAAACATCTTATAATATAGGCTTAAGTGCAAATATAAGATCTGATGCTAAGATGGAGTAT
721  ------------------------------------------------------------ 780
      K  T  S  Y  N  I  G  L  S  A  N  I  R  S  D  A  K  M  E  Y  -

GGTATCGGTTATGATTTTAATGCTGCAAGTAAATATACTGCACATCAAGGTACTTTAAAA
781  ------------------------------------------------------------ 840
      G  I  G  Y  D  F  N  A  A  S  K  Y  T  A  H  Q  G  T  L  K  -

GTACGTATAAATTTC
841  --------------- 855
      V  R  I  N  F  -
```

Fig. 18

```
     CAGGGGGATGCCGGTGTCTGGGCACGCATAATGAATGGTACCGGTTCGGCAGATGGTGAC
  1  ---------+---------+---------+---------+---------+---------+  60
     Q  G  D  A  G  V  W  A  R  I  M  N  G  T  G  S  A  D  G  D  -

TACAGCGATAACTACACTCACGTTCAGATTGGTGTCGACAGAAAGCATGAGCTGGACGGT
 61  ---------+---------+---------+---------+---------+---------+ 120
     Y  S  D  N  Y  T  H  V  Q  I  G  V  D  R  K  H  E  L  D  G  -

GTGGATTTATTTACGGGGGCATTGCTGACCTATACGGACAGCAATGCAAGCAGCCACGCA
121  ---------+---------+---------+---------+---------+---------+ 180
     V  D  L  F  T  G  A  L  L  T  Y  T  D  S  N  A  S  S  H  A  -

TTCAGTGGAAAAAACAAATCCGTGGGTGGCGGTCTGTATGCCTCTGCACTCTTTAATTCC
181  ---------+---------+---------+---------+---------+---------+ 240
     F  S  G  K  N  K  S  V  G  G  G  L  Y  A  S  A  L  F  N  S  -

GGAGCTTATTTTGACCTGATTGGTAAATATCTCCATCATGATAATCAGCACACGGCGAAT
241  ---------+---------+---------+---------+---------+---------+ 300
     G  A  Y  F  D  L  I  G  K  Y  L  H  H  D  N  Q  H  T  A  N  -

TTTGCCTCACTGGGAACAAAAGACTACAGCTCTCATTCCTGGTATGCCGGTGCTGAAGTT
301  ---------+---------+---------+---------+---------+---------+ 360
     F  A  S  L  G  T  K  D  Y  S  S  H  S  W  Y  A  G  A  E  V  -

GGTTATCGTTACCACCTGACGAAAGAGTCCTGGGTGGAGCCACAGATAGAGCTGGTTTAC
361  ---------+---------+---------+---------+---------+---------+ 420
     G  Y  R  Y  H  L  T  K  E  S  W  V  E  P  Q  I  E  L  V  Y  -

GGTTCTGTATCAGGAAAAGCTTTTAGCTGGGAAGCCCGGGGAATGGCTCTGAGCATGAAA
421  ---------+---------+---------+---------+---------+---------+ 480
     G  S  V  S  G  K  A  F  S  W  E  A  R  G  M  A  L  S  M  K  -

GACAAGGATTATAACCCACTGATTGGCCGTACTGGTGTTGACGTGGGAAGAGCCTTCTCC
481  ---------+---------+---------+---------+---------+---------+ 540
     D  K  D  Y  N  P  L  I  G  R  T  G  V  D  V  G  R  A  F  S  -

GGAGACGACTGGAAAATCACAGCTCGAGCCGGGCTGGGTTATCAGTTCGACCTGCTGGCG
541  ---------+---------+---------+---------+---------+---------+ 600
     G  D  D  W  K  I  T  A  R  A  G  L  G  Y  Q  F  D  L  L  A  -

AACGGAGAAACGGTTCTGCAGGATGCTTCCGGAGAGAAACGTTTCGAAGGTGAAAAAGAT
601  ---------+---------+---------+---------+---------+---------+ 660
     N  G  E  T  V  L  Q  D  A  S  G  E  K  R  F  E  G  E  K  D  -

AGCAGGATGCTGATGACGGTAGGGATGAATGCGGAAATTAAGGATAATATGCGTTTGGGA
661  ---------+---------+---------+---------+---------+---------+ 720
     S  R  M  L  M  T  V  G  M  N  A  E  I  K  D  N  M  R  L  G  -

CTGGAGCTGGAGAAATCAGCGTTCGGGAAATATAATGTGGATAATGCGATAAACGCCAAC
721  ---------+---------+---------+---------+---------+---------+ 780
     L  E  L  E  K  S  A  F  G  K  Y  N  V  D  N  A  I  N  A  N  -

TTCCGTTATGTTTTC
781  ---------+----- 795
     F  R  Y  V  F  -
```

Figure 19

```
     ACCCGTCAACTGTCCGGCCAGATCCACGCGGATATGGCGTCCGCCCAGATTAACGAAAGC
1    ------------------------------------------------------------+ 60
     T  R  Q  L  S  G  Q  I  H  A  D  M  A  S  A  Q  I  N  E  S  -

CGTTATCTGCGCGATACCGCCACCGAGCGGTTGCGCCAGGCCGATGGCCGCCGCACCGCT
61   ------------------------------------------------------------+ 120
     R  Y  L  R  D  T  A  T  E  R  L  R  Q  A  D  G  R  R  T  A  -

TCCGATATCAAAGCGGATGATAATGGCGCCTGGGCGAAATTGCTGGGCAACTGGGGGCAT
121  ------------------------------------------------------------+ 180
     S  D  I  K  A  D  D  N  G  A  W  A  K  L  L  G  N  W  G  H  -

GCTTCCGGCAACGACAACGCTACCGGTTACCAGACATCCACCTATGGCGTGCTGTTGGGT
181  ------------------------------------------------------------+ 240
     A  S  G  N  D  N  A  T  G  Y  Q  T  S  T  Y  G  V  L  L  G  -

CTGGACAGCGAACTGTTTGACGACGGCCGGCTGGGCGTGATGACCGGGTATACCCGCACG
241  ------------------------------------------------------------+ 300
     L  D  S  E  L  F  D  D  G  R  L  G  V  M  T  G  Y  T  R  T  -

TCGCTGGTAGGCGGTCTACAGTCAGTAGTCCACAGCGACACTACACATCTGGGGCTGTAC
301  ------------------------------------------------------------+ 360
     S  L  V  G  G  L  Q  S  V  V  H  S  D  T  T  H  L  G  L  Y  -

GGCGACAAACGCTTCGGCGCGTTGGCGCTGCCAGCGGGCGGCACCTATACCTGGCATCGC
361  ------------------------------------------------------------+ 420
     G  D  K  R  F  G  A  L  A  L  P  A  G  G  T  Y  T  W  H  R  -

ATCGACACGTCGCGCTCGGTAAACTACGGCGCGCAGGCGGATCGCGAAAAGGCCCGCTAT
421  ------------------------------------------------------------+ 480
     I  D  T  S  R  S  V  N  Y  G  A  Q  A  D  R  E  K  A  R  Y  -

AACGCGCGCACCGGTCAGCTGTTTATCGAAAGCGGCTACGATTGGAGCAACGACGTGGTC
481  ------------------------------------------------------------+ 540
     N  A  R  T  G  Q  L  F  I  E  S  G  Y  D  W  S  N  D  V  V  -

AATCTTGAGCCGTTCGCCAACCTGGCGTACACCCACTATCGCAACGAGGGGATCAACGAG
541  ------------------------------------------------------------+ 600
     N  L  E  P  F  A  N  L  A  Y  T  H  Y  R  N  E  G  I  N  E  -

CAAGGCGGGGCGGCGGCGCTGCGCGGCGATAAGCAAAGTCAGTCCGCCACCGCTTCGACG
601  ------------------------------------------------------------+ 660
     Q  G  G  A  A  A  L  R  G  D  K  Q  S  Q  S  A  T  A  S  T  -

CTGGGCCTGCGCGCCGATACGCAATGGCAGACCGACAGCGTGGCGATCGCCCTGCCGGGC
661  ------------------------------------------------------------+ 720
     L  G  L  R  A  D  T  Q  W  Q  T  D  S  V  A  I  A  L  P  G  -

GAGCTGGGTTGGCAACATCAGTACGGCAAGCTGGAGCGTAAAACACAGCTGATGTTCAAA
721  ------------------------------------------------------------+ 780
     E  L  G  W  Q  H  Q  Y  G  K  L  E  R  K  T  Q  L  M  F  K  -

CGCAGCGATGTCGCGTTCGACGTGAACAGCGTCCCTGTTTCTCGCGATGGGGCCATTCTG
781  ------------------------------------------------------------+ 840
     R  S  D  V  A  F  D  V  N  S  V  P  V  S  R  D  G  A  I  L  -

AAAGCGGGCGTCGATGTATCGATTAACAAAAACGTCGTCCTGTCCCTTGGGTACGGCGGG
841  ------------------------------------------------------------+ 900
     K  A  G  V  D  V  S  I  N  K  N  V  V  L  S  L  G  Y  G  G  -

CAGCTGTCGTCCAACCACCAGGACAACAGCGTCAACGCCGGCCTGACCTGGCGGTTC
901  ---------------------------------------------------------  957
     Q  L  S  S  N  H  Q  D  N  S  V  N  A  G  L  T  W  R  F
```

Fig.20

```
    ACCCGTCAACTGTCCGGCCAGATCCACGCGGATATGGCTTCCGCCCAGATCAACGAAAGC
  1 ------------+---------+---------+---------+---------+---------+ 60
    T  R  Q  L  S  G  Q  I  H  A  D  M  A  S  A  Q  I  N  E  S  -

CGTTACCTGCGCGATACCGCCACCGAGCGCTTGCGCCAGGCGGAAGGCCGCCGCACCGCT
 61 ------------+---------+---------+---------+---------+---------+ 120
    R  Y  L  R  D  T  A  T  E  R  L  R  Q  A  E  G  R  R  T  A  -

ACCGACATTAAAGCGGATGACAACGGCGCCTGGGCGAAACTGCTGGGTAGCTGGGGGCAT
121 ------------+---------+---------+---------+---------+---------+ 180
    T  D  I  K  A  D  D  N  G  A  W  A  K  L  L  G  S  W  G  H  -

GCTTCCGGCAACGACAACGCCACCGGTTACCAGACCTCCACCTATGGCGTGCTGTTAGGT
181 ------------+---------+---------+---------+---------+---------+ 240
    A  S  G  N  D  N  A  T  G  Y  Q  T  S  T  Y  G  V  L  L  G  -

CTGGACAGCGAACTGTTTGGCGACGGCCGGCTTGGCATGATGACCGGGTATACCCGCACT
241 ------------+---------+---------+---------+---------+---------+ 300
    L  D  S  E  L  F  G  D  G  R  L  G  M  M  T  G  Y  T  R  T  -

TCGCTGGATGGAGGTTATCAGTCAGATGCTCACAGCGACAACTACCATCTGGGGCTGTAC
301 ------------+---------+---------+---------+---------+---------+ 360
    S  L  D  G  G  Y  Q  S  D  A  H  S  D  N  Y  H  L  G  L  Y  -

GGCGACAAACGCTTCGGCGCGTTGGCGCTGCGAGCGGGCGGCACCTATACCTGGCATCGC
361 ------------+---------+---------+---------+---------+---------+ 420
    G  D  K  R  F  G  A  L  A  L  R  A  G  G  T  Y  T  W  H  R  -

ATCGACACCTCGCGTTCGGTGAACTACGGCGCGCAGTCGGATCGCGAGAAGGCCAAGTAT
421 ------------+---------+---------+---------+---------+---------+ 480
    I  D  T  S  R  S  V  N  Y  G  A  Q  S  D  R  E  K  A  K  Y  -

AACGCGCGCACCGGTCAGCTGTTCATCGAAAGCGGCTACGATTGGACGAGCGATGCGGTC
481 ------------+---------+---------+---------+---------+---------+ 540
    N  A  R  T  G  Q  L  F  I  E  S  G  Y  D  W  T  S  D  A  V  -

AACCTTGAGCCGTTCGCCAACCTGGCGTATACCCATTACCGTAACGAGGAGATCAACGAG
541 ------------+---------+---------+---------+---------+---------+ 600
    N  L  E  P  F  A  N  L  A  Y  T  H  Y  R  N  E  E  I  N  E  -

CAAGGCGGGGCAGCGGCGCTGCGCGGCGACAAACAAAGTCAGTCCGCCACCGCCTCGACG
601 ------------+---------+---------+---------+---------+---------+ 660
    Q  G  G  A  A  A  L  R  G  D  K  Q  S  Q  S  A  T  A  S  T  -

TTGGGTCTGCGCGCCGACACCGAGTGGCAAACCGACAGCGTGGCGATCGCGCTGCGCGGC
661 ------------+---------+---------+---------+---------+---------+ 720
    L  G  L  R  A  D  T  E  W  Q  T  D  S  V  A  I  A  L  R  G  -

GAGCTGGGTTGGCAGCATCAGTACGGCAAGCTGGAGCGTAAAACGCAGCTGATGTTCAAA
721 ------------+---------+---------+---------+---------+---------+ 780
    E  L  G  W  Q  H  Q  Y  G  K  L  E  R  K  T  Q  L  M  F  K  -

CGCACTGATGCGGCGTTCGACGTGAACAGCGTGCCTGTTTCTCGCGATGGCGCGATTCTG
781 ------------+---------+---------+---------+---------+---------+ 840
    R  T  D  A  A  F  D  V  N  S  V  P  V  S  R  D  G  A  I  L  -

AAAGCGGGCGTCGATGTATCGATTAACAAAAACGCCGTCCTGTCCCTTGGCTACGGCGGG
841 ------------+---------+---------+---------+---------+---------+ 900
    K  A  G  V  D  V  S  I  N  K  N  A  V  L  S  L  G  Y  G  G  -

CAGCTGTCGTCCAACCACCAGGACAACAGCGTCAACGCCGGTCTGACCTGGCGCTTC
901 ------------+---------+---------+---------+---------+------- 957
    Q  L  S  S  N  H  Q  D  N  S  V  N  A  G  L  T  W  R  F  -
```

Fig.21

```
    TTCCGTCAGCTGTCGGGGCAAATCCATGCGGACATCGCGTCGGCGCTGGTGAACGACAGC
  1 ------------+----------+----------+----------+----------+----------+ 60
    F  R  Q  L  S  G  Q  I  H  A  D  I  A  S  A  L  V  N  D  S  -

CGCTACCTGCGTGAGGCGCTGAACGGGCGTCTGCGTCAGGCGGAAGGGCTGGCGAGCTCG
 61 ------------+----------+----------+----------+----------+----------+ 120
    R  Y  L  R  E  A  L  N  G  R  L  R  Q  A  E  G  L  A  S  S  -

TCGGCCATCAAGGCGGACGAGGACGGCGCCTGGGCGCAGCTGCTGGGAGCGTGGGACCAT
121 ------------+----------+----------+----------+----------+----------+ 180
    S  A  I  K  A  D  E  D  G  A  W  A  Q  L  L  G  A  W  D  H  -

GCGTCGGGCGACGCCAACGCCACCGGCTATCAGGCCTCGACCTACGGGGTGCTGGTGGGG
181 ------------+----------+----------+----------+----------+----------+ 240
    A  S  G  D  A  N  A  T  G  Y  Q  A  S  T  Y  G  V  L  V  G  -

CTGGACTCGGCGGCGGCGGCCGACTGGCGGCTGGGGGTGGCGACCGGCTACACCCGCACC
241 ------------+----------+----------+----------+----------+----------+ 300
    L  D  S  A  A  A  A  D  W  R  L  G  V  A  T  G  Y  T  R  T  -

TCGCTGCACGGCGGGTATGGGTCGAAGGCGGACAGCGACAACTACCACCTGGCGGCGTAC
301 ------------+----------+----------+----------+----------+----------+ 360
    S  L  H  G  G  Y  G  S  K  A  D  S  D  N  Y  H  L  A  A  Y  -

GGCGACAAGCAGTTCGGGGCGCTGGCGCTGCGGGGCGGGGCGGGCTACACCTGGCACCGC
361 ------------+----------+----------+----------+----------+----------+ 420
    G  D  K  Q  F  G  A  L  A  L  R  G  G  A  G  Y  T  W  H  R  -

ATCGACACCAAGCGGTCGGTGAACTACGGGATGCAGTCGGACCGCGACACGGCGAAGTAC
421 ------------+----------+----------+----------+----------+----------+ 480
    I  D  T  K  R  S  V  N  Y  G  M  Q  S  D  R  D  T  A  K  Y  -

AGCGCGCGCACCGAGCAGCTGTTCGCGGAAGCGGGCTACAGCGTGAAGGGCGAGTGGCTG
481 ------------+----------+----------+----------+----------+----------+ 540
    S  A  R  T  E  Q  L  F  A  E  A  G  Y  S  V  K  G  E  W  L  -

AACCTGGAGCCGTTCGTCAACCTGGCGTACGTGAACTTTGAAAACAACGGCATCGCGGAA
541 ------------+----------+----------+----------+----------+----------+ 600
    N  L  E  P  F  V  N  L  A  Y  V  N  F  E  N  N  G  I  A  E  -

AGCGGCGGCGCAGCGGCGCTGCGCGGCGACAAGCAGCACACCGACGCGACGGTGTCGACG
601 ------------+----------+----------+----------+----------+----------+ 660
    S  G  G  A  A  A  L  R  G  D  K  Q  H  T  D  A  T  V  S  T  -

CTGGGACTGCGCGCGGACACTGAGTGGCAGGTGAGCCCGGGCACGACGGTGGCGCTGCGC
661 ------------+----------+----------+----------+----------+----------+ 720
    L  G  L  R  A  D  T  E  W  Q  V  S  P  G  T  T  V  A  L  R  -

AGCGAGCTGGGGTGGCAACACCAGTACGGCGGGCTGGAGCGTGGCACCGGGCTGCGGTTC
721 ------------+----------+----------+----------+----------+----------+ 780
    S  E  L  G  W  Q  H  Q  Y  G  G  L  E  R  G  T  G  L  R  F  -

AACGGCGGCAACGCGCCGTTCGTGGTGGACAGCGTGCCGGTGTCGCGCGACGGGATGGTG
781 ------------+----------+----------+----------+----------+----------+ 840
    N  G  G  N  A  P  F  V  V  D  S  V  P  V  S  R  D  G  M  V  -

CTGAAGGCGGGTGCGGAAGTGGCGGTGAACGAGAACGCCTCGCTGTCGCTGGGCTACGGC
841 ------------+----------+----------+----------+----------+----------+ 900
    L  K  A  G  A  E  V  A  V  N  E  N  A  S  L  S  L  G  Y  G  -

GGGCTGCTGTCGCAGAACCATCAGGACAACAGCGTCAACGCCGGCTTCACCTGGCGCTTC
901 ------------+----------+----------+----------+----------+----------+ 960
    G  L  L  S  Q  N  H  Q  D  N  S  V  N  A  G  F  T  W  R  F  -
```

Fig.22

```
    TTCCGTCAGCTGTCGGGGCAAATCCATGCGGACATCGCGTCGGCGCTGGTGAACGACAGC
  1 ------------------------------------------------------------ 60
    F  R  Q  L  S  G  Q  I  H  A  D  I  A  S  A  L  V  N  D  S  -

CGCTACCTGCGTGAGGCGCTGAACGGGCGTCTGCGTCAGGCGGAAGGGCTGGCGAGCTCG
 61 ------------------------------------------------------------ 120
    R  Y  L  R  E  A  L  N  G  R  L  R  Q  A  E  G  L  A  S  S  -

TCGGCCATCAAGGCGGACGAGGACGGCGCCTGGGCGCAGCTGCTGGGAGCGTGGGACCAT
121 ------------------------------------------------------------ 180
    S  A  I  K  A  D  E  D  G  A  W  Q  L  L  G  A  W  D  H  -

GCGTCGGGCGACGCCAACGCCACCGGCTATCAGGCCTCGACCTACGGGGTGCTGGTGGGG
181 ------------------------------------------------------------ 240
    A  S  G  D  A  N  A  T  G  Y  Q  A  S  T  Y  G  V  L  V  G  -

CTGGACTCGGCGGCGGCGGCCGACTGGCGGCTGGGGGTGGCGACCGGCTACACCCGCACC
241 ------------------------------------------------------------ 300
    L  D  S  A  A  A  A  D  W  R  L  G  V  A  T  G  Y  T  R  T  -

TCGCTGCACGGCGGGTATGGGTCGAAGGCGGACAGCGACAACTACCACCTGGCGGCGTAC
301 ------------------------------------------------------------ 360
    S  L  H  G  G  Y  G  S  K  A  D  S  D  N  Y  H  L  A  A  Y  -

GGCGACAAGCAGTTCGGGGCGCTGGCGCTGCGGGGCGGGGCGGGCTACACCTGGCACCGC
361 ------------------------------------------------------------ 420
    G  D  K  Q  F  G  A  L  A  L  R  G  G  A  G  Y  T  W  H  R  -

ATCGACACCAAGCGGTCGGTGAACTACGGGATGCAGTCGGACCGCGACACGGCGAAGTAC
421 ------------------------------------------------------------ 480
    I  D  T  K  R  S  V  N  Y  G  M  Q  S  D  R  D  T  A  K  Y  -

AGCGCGCGCACCGAGCAGCTGTTCGCGGAAGCGGGCTACAGCGTGAAGGGCGAGTGGCTG
481 ------------------------------------------------------------ 540
    S  A  R  T  E  Q  L  F  A  E  A  G  Y  S  V  K  G  E  W  L  -

AACCTGGAGCCGTTCGTCAACCTGGCGTACGTGAACTTTGAAAACAACGGCATCGCGGAA
541 ------------------------------------------------------------ 600
    N  L  E  P  F  V  N  L  A  Y  V  N  F  E  N  N  G  I  A  E  -

AGCGGCGGCGCAGCGGCGCTGCGCGGCGACAAGCAGCACACCGACGCGACGGTGTCGACG
601 ------------------------------------------------------------ 660
    S  G  G  A  A  A  L  R  G  D  K  Q  H  T  D  A  T  V  S  T  -

CTGGGACTGCGCGCGGACACTGAGTGGCAGGTGAGCCCGGGCACGACGGTGGCGCTGCGC
661 ------------------------------------------------------------ 720
    L  G  L  R  A  D  T  E  W  Q  V  S  P  G  T  T  V  A  L  R  -

AGCGAGCTGGGGTGGCAACACCAGTACGGCGGGCTGGAGCGTGGCACCGGGCTGCGGTTC
721 ------------------------------------------------------------ 780
    S  E  L  G  W  Q  H  Q  Y  G  G  L  E  R  G  T  G  L  R  F  -

AACGGCGGCAACGCGCCGTTCGTGGTGGACAGCGTGCCGGTGTCGCGCGACGGGATGGTG
781 ------------------------------------------------------------ 840
    N  G  G  N  A  P  F  V  V  D  S  V  P  V  S  R  D  G  M  V  -

CTGAAGGCGGGTGCGGAAGTGGCGGTGAACGAGAACGCCTCGCTGTCGCTGGGCTACGGC
841 ------------------------------------------------------------ 900
    L  K  A  G  A  E  V  A  V  N  E  N  A  S  L  S  L  G  Y  G  -

GGGCTGCTGTCGCAGAACCATCAGGACAACAGCGTCAACGCCGGCTTCACCTGGCGCTTC
901 ------------------------------------------------------------ 960
    G  L  L  S  Q  N  H  Q  D  N  S  V  N  A  G  F  T  W  R  F  -
```

Fig.23

```
    ATTAATGGCGAAGCCGGTACGTGGGTGCGTCTGCTGAACGGTTCCGGCTCTGCTGATGGC
  1 ---------+---------+---------+---------+---------+---------+ 60
     I  N  G  E  A  G  T  W  V  R  L  L  N  G  S  G  S  A  D  G  -

GGTTTCACTGACCACTATACCCTGCTGCAGATGGGGGCTGACCGTAAGCACGAACTGGGA
 61 ---------+---------+---------+---------+---------+---------+ 120
     G  F  T  D  H  Y  T  L  L  Q  M  G  A  D  R  K  H  E  L  G  -

AGTATGGACCTGTTTACCGGCGTGATGGCCACCTACACTGACACAGATGCGTCAGCAGAC
121 ---------+---------+---------+---------+---------+---------+ 180
     S  M  D  L  F  T  G  V  M  A  T  Y  T  D  T  D  A  S  A  D  -

CTGTACAGCGGTAAAACAAAATCATGGGGTGGTGGTTTCTATGCCAGTGGTCTGTTCCGG
181 ---------+---------+---------+---------+---------+---------+ 240
     L  Y  S  G  K  T  K  S  W  G  G  G  F  Y  A  S  G  L  F  R  -

TCCGGCGCTTACTTTGATGTGATTGCCAAATATATTCACAATGAAAACAAATATGACCTG
241 ---------+---------+---------+---------+---------+---------+ 300
     S  G  A  Y  F  D  V  I  A  K  Y  I  H  N  E  N  K  Y  D  L  -

AACTTTGCCGGAGCTGGTAAACAGAACTTCCGCAGCCATTCACTGTATGCAGGTGCAGAA
301 ---------+---------+---------+---------+---------+---------+ 360
     N  F  A  G  A  G  K  Q  N  F  R  S  H  S  L  Y  A  G  A  E  -

GTCGGATACCGTTATCATCTGACAGATACGACGTTTGTTGAACCTCAGGCGGAACTGGTC
361 ---------+---------+---------+---------+---------+---------+ 420
     V  G  Y  R  Y  H  L  T  D  T  T  F  V  E  P  Q  A  E  L  V  -

TGGGGAAGACTGCAGGGCCAAACATTTAACTGGAACGACAGTGGAATGGATGTCTCAATG
421 ---------+---------+---------+---------+---------+---------+ 480
     W  G  R  L  Q  G  Q  T  F  N  W  N  D  S  G  M  D  V  S  M  -

CGTCGTAACAGCGTTAATCCTCTGGTAGGCAGAACCGGCGTTGTTTCCGGTAAAACCTTC
481 ---------+---------+---------+---------+---------+---------+ 540
     R  R  N  S  V  N  P  L  V  G  R  T  G  V  V  S  G  K  T  F  -

AGTGGTAAGGACTGGAGTCTGACAGCCCGTGCCGGCCTGCATTATGAGTTCGATCTGACG
541 ---------+---------+---------+---------+---------+---------+ 600
     S  G  K  D  W  S  L  T  A  R  A  G  L  H  Y  E  F  D  L  T  -

GACAGTGCTGACGTTCATCTGAAGGATGCAGCGGGAGAACATCAGATTAATGGCAGAAAA
601 ---------+---------+---------+---------+---------+---------+ 660
     D  S  A  D  V  H  L  K  D  A  A  G  E  H  Q  I  N  G  R  K  -

GACAGTCGTATGCTTTACGGTGTGGGGTTAAATGCCCGGTTTGGCGACAATACGCGTTTG
661 ---------+---------+---------+---------+---------+---------+ 720
     D  S  R  M  L  Y  G  V  G  L  N  A  R  F  G  D  N  T  R  L  -

GGGCTGGAAGTTGAACGCTCTGCATTTGGTAAATACAACACAGATGATGCGATAAACGCT
721 ---------+---------+---------+---------+---------+---------+ 780
     G  L  E  V  E  R  S  A  F  G  K  Y  N  T  D  D  A  I  N  A  -

AATATTCGTTATTCATTC
781 ---------+-------- 798
     N  I  R  Y  S  F  -
```

Fig. 24

```
      TCTTTAGAAAGCGCGGCGGAAGTGTTGTATCAATTTGCCCCTAAATATGAAAAACCCACC
  1   ---------+---------+---------+---------+---------+---------+  60
      S  L  E  S  A  A  E  V  L  Y  Q  F  A  P  K  Y  E  K  P  T

AATGTTTCGCTAACGCTATTGGGGGAACGAGCTTGAATAGTGGCGGTAACGCTTCATTG
 61   ---------+---------+---------+---------+---------+---------+ 120
      N  V  W  A  N  A  I  G  G  T  S  L  N  S  G  G  N  A  S  L

TATGGCACAAGTGCGGGCGTAGATGCTTACCTTAACGGGGAAGTGGAAGCCATTGTGGGC
121   ---------+---------+---------+---------+---------+---------+ 180
      Y  G  T  S  A  G  V  D  A  Y  L  N  G  E  V  E  A  I  V  G

GGTTTTGGAAGCTATGGTTATAGCTCCTTTAGTAATCAAGCGAACTCTCTTAACTCTGGG
181   ---------+---------+---------+---------+---------+---------+ 240
      G  F  G  S  Y  G  Y  S  S  F  S  N  Q  A  N  S  L  N  S  G

GCCAATAACACTAATTTTGGCGTGTATAGCCGTATTTTTGCTAACCAGCATGAATTTGAC
241   ---------+---------+---------+---------+---------+---------+ 300
      A  N  N  T  N  F  G  V  Y  S  R  I  F  A  N  Q  H  E  F  D

TTTGAAGCTCAAGGGGCGCTAGGGAGTGATCAATCAAGCTTGAATTTCAAAAGCGCTTTA
301   ---------+---------+---------+---------+---------+---------+ 360
      F  E  A  Q  G  A  L  G  S  D  Q  S  S  L  N  F  K  S  A  L

TTGCGAGATTTGAATCAAAGCTATAATTACTTAGCCTATAGCGCTGCAACAAGAGCGAGC
361   ---------+---------+---------+---------+---------+---------+ 420
      L  R  D  L  N  Q  S  Y  N  Y  L  A  Y  S  A  A  T  R  A  S

TATGGTTATGACTTCGCGTTTTTTAGGAACGCTTTGGTGTTAAAACCAAGCGTGGGCGTG
421   ---------+---------+---------+---------+---------+---------+ 480
      Y  G  Y  D  F  A  F  F  R  N  A  L  V  L  K  P  S  V  G  V

AGCTATAACCATTTAGGTTCAACCAACTTTAAAAGCAACAGCAATCAAAAAGTGGCTTTG
481   ---------+---------+---------+---------+---------+---------+ 540
      S  Y  N  H  L  G  S  T  N  F  K  S  N  S  N  Q  K  V  A  L

AAAAATGGTGCAAGCAGTCAGCATTTATTCAACGCTAGTGCTAATGTGGAAGCGCGCTAT
541   ---------+---------+---------+---------+---------+---------+ 600
      K  N  G  A  S  S  Q  H  L  F  N  A  S  A  N  V  E  A  R  Y

TATTATGGGACACTTCATACTTCTACATGAACGCTGGAGTTTTACAAGAGTTCGCTAAC
601   ---------+---------+---------+---------+---------+---------+ 660
      Y  Y  G  D  T  S  Y  F  Y  M  N  A  G  V  L  Q  E  F  A  N

TTTGGTTCTAGCAATGCGGTGTCTTTAAACACCTTTAAAGTGAATGCTACTCGTAACCCT
661   ---------+---------+---------+---------+---------+---------+ 720
      F  G  S  S  N  A  V  S  L  N  T  F  K  V  N  A  T  R  N  P

TTAAATACCCATGCGAGAGTGATGATGGGTGGGGAATTAAAATTAGCTAAAGAAGTGTTT
721   ---------+---------+---------+---------+---------+---------+ 780
      L  N  T  H  A  R  V  M  M  G  G  E  L  K  L  A  K  E  V  F

TTGAATTTGGGCTTTGTTTATTTGCACAATTTGATTTCCAATATAGGCCATTTCGCTTCC
781   ---------+---------+---------+---------+---------+---------+ 840
      L  N  L  G  F  V  Y  L  H  N  L  I  S  N  I  G  H  F  A  S

AATTTAGGAATGAGGTATAGTTTC
841   ---------+---------+---- 864
      N  L  G  M  R  Y  S  F
```

US 7,129,060 B1

EXPORT SYSTEMS FOR RECOMBINANT PROTEINS

CROSS-REFERENCES TO RELATED APPLICATIONS

This application is a §371 of PCT/EP96/01130/01130 filed on Mar. 15, 1996.

BACKGROUND OF THE INVENTION

1. Field of the Invention

The present invention relates to vectors, host-vector combinations and processes for preparing stable fusion proteins consisting of a carrier protein and a passenger protein, where expression of the fusion proteins leads to exposure of the passenger domains on the surface of bacterial cells, especially *Escherichia coli* cells. If required, the passenger domains can be released into the medium by proteases, for example by selected host factors such as, for example, OmpT.

2. Description of Related Art

The exposure of recombinant proteins on the surface of bacterial cells is a method with a large number of possible microbiological, molecular biological, immunological or industrial applications. Production of recombinant proteins in this manner makes their properties, for example binding affinities or enzymatic activities (Francisco et al., Bio. Technology 11 (1993) 491–495) available without a further step such as, for example, disruption of the producer cell being necessary. Since only a limited number of factors are naturally expressed on the bacterial surface, there is in addition specific enrichment of the recombinant protein by comparison with cytosolic production. Another considerable advantage is that the same methods used to select the recombinant protein which is sought can also be used to isolate the producer of this protein, a bacterial cell, and thus a clonal producer which can be permanently stored, stably reproduced and grown on a large scale can be obtained.

Various systems have been used to date for the presentation of recombinant proteins on the cell surface, but these without exception are also used naturally for the transport or secretion of bacterial surface proteins (Little et al., TIBTECH 11 (1993), 3–5). Significantly, in these cases the DNA region which naturally codes for the protein to be transported, the passenger, was replaced or supplemented by the coding DNA region of the required recombinant protein, although the coding regions of the protein domains responsible for the transport, the carrier proteins, usually remained unchanged. It is clear from this that systems in which passenger and carrier components are present immediately adjacent or encoded in one gene, so-called one-component systems, have a considerable advantage by comparison with systems having several independent components (Gentschev et al., Behring Inst. Mitt. 95 (1994) 57–66), especially in the production of universally usable vectors which, besides the property of stable replication, one or more selection markers, and the protein domains needed for transport, must also contain an insertion site for the DNA fragment encoding the passenger. The carrier proteins used in many one-component systems used to date have been *E. coli* outer membrane proteins. These include, inter alia, LamB (Charbit et al., Gene 70 (1988), 181–189), PhoE (Agterberg et al., Gene 59 (1987), 145–150) or OmpA (Franscisco et al., Proc. Natl. Acad. Sci (1992), 2713–2717), whose use entails disadvantages, however. Thus, additional protein sequences can be integrated only in loops exposed on the surface, which on the one hand leads to fixed amino- and carboxyl-terminal ends on the flanking carrier protein sequences, and on the other hand has a limiting effect on the length of the sequences to be introduced. Although the use of peptidoglycan-associated lipoprotein (PAL) as carrier protein leads to transport to the outer membrane, no presentation of native protein sequences on the surface of *E. coli* is possible therewith (Fuchs et al., Biol. Technology 9 (1991), 1369–1372). Surface expression of relatively large proteins is possible using a fusion of OmpA and Lpp as carrier protein portion, to whose carboxyl end the passenger protein sequences are attached (Franscisco et al., Proc. Natl. Acad. Sci (1992), 2713–2717). A disadvantage which has to be accepted in this case is that the fixing of the N-terminus of the passenger may prevent correct folding or functioning.

Also known are so-called autotransporter-containing proteins, a family of secreted proteins in Gram-negative bacteria. The publication of Jose et al. (Mol. Microbiol. 18 (1995), 377–382) mentions some examples of such autotransporter proteins. These proteins contain a protein domain which enables an N-terminally attached protein domain to be transported through a pore structure formed from ú-pleated sheet structures in the outer membrane of Gram-negative bacteria. The autotransporter-containing proteins are synthesized as so-called polyprotein precursor molecule. The typical structure of such a precursor protein is divided into three. At the N-terminus there is a signal sequence which is responsible for the transport through the inner membrane, taking advantage of the Sec transport apparatus present in the host and being deleted during this. To this is attached the protein domain to be secreted, followed by a C-terminal helper domain which forms a pore in the outer membrane, through which the N-terminally attached protein domain to be secreted is translocated to the surface. Depending on its function to be carried out, the latter remains there linked to the helper, which is now serving as membrane anchor, on the bacterial surface, or is deleted by proteolytic activity, and this proteolytic activity may be intrinsic to the protein domain to be secreted or be a property derived from the host or be an external/specifically added activity (for example thrombin, IgA protease). Secretion of heterologous polypeptides or proteins using an expression system based on an autotransporter is known. Thus, for example, it is known from EP-A-0 254 090 or the publication of Klauser et al. (EMBO J. 11 (1992), 2327–2335) that the helper domain of the IgA protease from *N. gonorrhoeae* can express heterologous poly-peptides as passenger domains in the heterologous bacterial strains *E. coli* and *Salmonella typhimurium*.

In addition, the extracellular transport of the protein VirG by *shigella* is described in Suzuki et al. (J. Biol. Chem. 170 (1995) 30874–30880). This protein is likewise an IgA protease-like autotransporter which is capable of the expression of foreign polypeptides such as, for example, MalE and PhoA, which have been covalently linked to the N terminus of the auto-transporter domain of VirG. In addition, the paper by Shimada et al. (J. Biochem, 116 (1994), 327–334) describes the extracellular transport of a heterologous polypeptide, namely pseudoazurin from *A. faecales*, in *E. coli* using the autotransporter domain of the serine protease from *S. marcescens*.

In the processes described in the prior art for preparing for the expression of heterologous passenger proteins with the aid of autotransporter systems, however, considerable disadvantages have been found. Thus, on use of the transporter or helper domain of the IgA protease from *N. gonorrhoeae* in *E. coli* as host strain, considerable compatibility problems frequently arise. Excessive expression leads to cytolysis or the bacteria show reduced growth even with moderate expression, which in both cases leads to a considerable reduction in the yield of fusion protein and points to weaknesses in the stability of the system. The present invention was thus based on the technical problem of providing carrier proteins which, especially on use of *E. coli* as host strain, do not lead to these disadvantages because, for a variety of reasons, *E. coli* is to be preferred to, for example, *Neisseria gonorrhoeae* as host strain. On the one hand, *E. coli* strains with recombinant DNA can be cultured even in simple laboratories of safety level 1. In addition, *E. coli* strains have already been used in the commercial production of recombinant proteins. This means that there is a considerable advantage in the handling and manipulation of recombinant *E. coli* strains by comparison with other host strains. In addition, a large number of accurately characterized mutant strains of *E. coli* already exist and permit a selection of the host strain depending on the required use.

This problem is solved by a method for presenting peptides or/and polypeptides on the surface of Gram-negative host bacteria, where
a) there is provision of a host bacterium which is transformed with a vector on which is located, operatively linked to a promoter, a fused nucleic acid sequence comprising:
   (i) a signal peptide-encoding nucleic acid section,
   (ii) a nucleic acid section coding for the passenger peptide or/and passenger poly-peptide to be presented,
   (iii) where appropriate a nucleic acid section coding for a protease recognition site,
   (iv) a nucleic acid section coding for a transmembrane linker and
   (v) a nucleic acid section coding for a transporter domain of an autotransporter; and
(b) the host bacterium is cultivated under conditions with which there is expression of the fused nucleic acid sequence and presentation of the peptide or polypeptide encoded by the nucleic acid section (ii) on the surface of the host bacterium, characterized in that the nucleic acid section (ii) is heterologous relative to the nucleic acid section coding for the transporter domain (v), and the host bacterium is homologous relative to the nucleic acid section coding for the transporter domain (v).

BRIEF SUMMARY OF THE INVENTION

The present invention relates to vectors, host-vector combinations and processes for preparing stable fusion proteins consisting of a carrier protein and a passenger protein, where expression of the fusion proteins leads to exposure of the passenger domains on the surface of bacterial cells, especially *Escherichia coli* cells. If required, the passenger domains can be released into the medium by proteases, for example by selected host factors such as, for example, OmpT.

The present invention further relates to the use of carrier proteins or carrier protein portions from natural proteins which are present as amino-acid sequences in data banks or files and are called, in accordance with their properties, autotransporters.

Methods for identifying and selecting bacteria which express at least one passenger protein on their surface with defined affinity for a binding partner, and the use thereof for diagnostic purposes, are made possible by the present invention. In particular, the process according to the invention allows peptide libraries to be expressed on the surface of bacterial cells, with the aid of which it is possible, for example, to determine the ligands having the highest affinity in the case of antibodies, MHC molecules or other components of the immune system.

Also made possible by the process according to the invention is the production of fusion proteins which are composed of portions of heavy and light antibody domains and an autotransporter, and transport thereof through the bacterial cell coat. In a specific embodiment, finally, the targeted variation of recombinant antibodies with binding activity, and their functional presentation on the cell surface of *Escherichia coli* become possible.

The process according to the invention generally allows recombinant proteins, which may be receptors or ligands, to be expressed on the bacterial surface, and selection on the basis of the binding affinity for a binding partner, which makes selection, associated therewith, of a clonal producer possible.

The use of bacteria which express protein fusions on the cell surface and which are present bound to a carrier material or in solution for the specific enrichment or purification of a binding partner showing affinity for protein domains exposed on this surface is also according to the invention. Furthermore, the present invention also relates to the surface expression of enzymes or other proteins with biologically, chemically or industrially relevant properties, and, where needed, the specific release thereof into the surrounding medium.

The pore typical of autotransporters in the outer membrane of Gram-negative bacteria is formed by amphipatic ú-pleated sheet structures, that is to say by domains with ú-pleated sheet structure and alternating hydrophobic and hydrophilic amino acids. This can be demonstrated by plotting a relative hydrophobicity value of the amino acid, which has been assigned to the amino acid by means of a particular algorithm, against the position of the amino acid. The algorithm of Vogel and Jähnig (J. Mol. Biol. 190 (1986) 191–199) was used. The arrows show the possible membrane passages, with an arrow to the left denoting that the membrane passage runs from the inside to the outside and an arrow to the right indicating a membrane passage from the outside to the inside. SP indicates a relative surface probability of the amino acids calculated by the method of Emini et al. (J. Virol. 55 (1985), 836–839).

Figure 2:
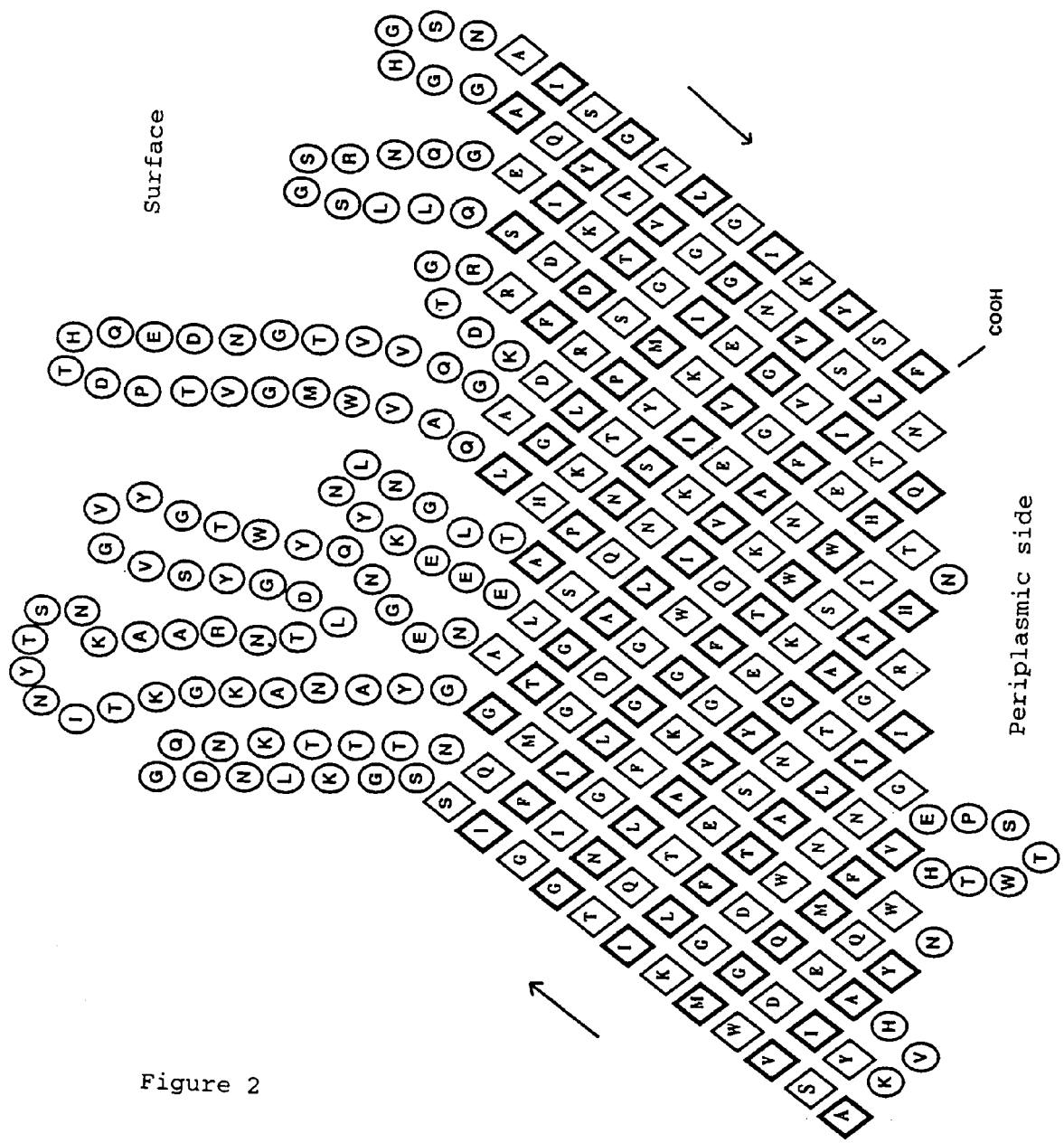

FIG. 2:
Model of the autotransporter from the AIDA-I protein.

Figure 1:
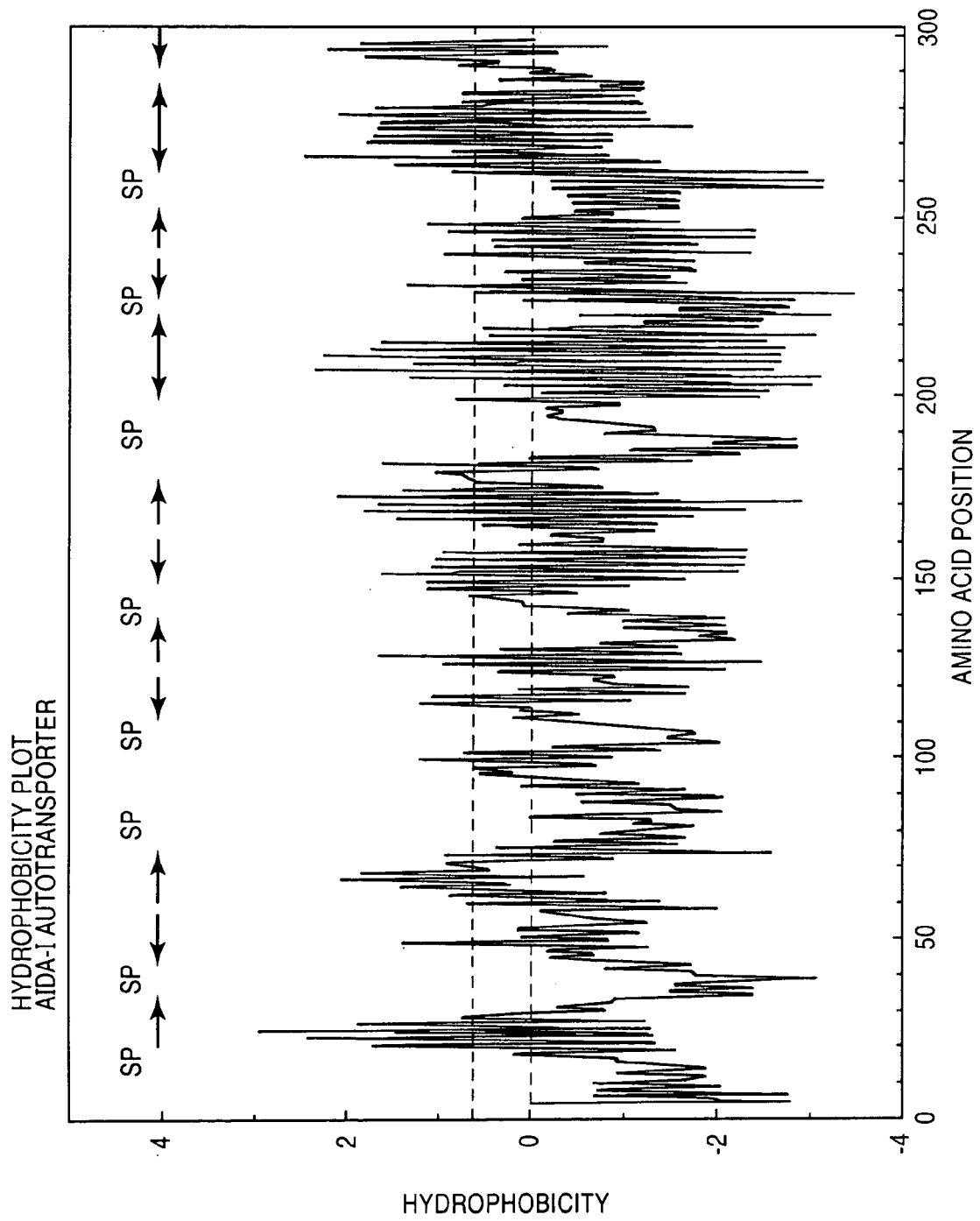
FIG. 1:
Hydrophobicity of the C-terminal 300 amino acids of the AIDA-I protein.

Starting from the plot of the relative hydrophobicity of an amino acid against its position (FIG. 1), the barrel structure formed by the antiparallel, amphipatic ú-pleated sheets can be depicted as model. The barrel structure which is depicted here cut open is closed in the membrane by interaction of the first with the antiparallel last membrane passage. The amino acids written inside rhombi are located in the membrane region, with those surrounded by thick lines being relatively hydrophobic and being oriented towards the outside of the barrel, that is to say towards the membrane, while those surrounded by thin lines are relatively hydrophilic and point with their side chains towards the inside of the pore. Amino acids shown in circles form loops outside the membrane. Alanine at position 1 of the model has the number 1014 in the complete sequence of the AIDA-I, while the terminal phenylalanine has the number 1286 in the complete sequence (Benz and Schmidt, Mol Microbiol 11 (1992), 1539–1546).

FIG. 3a:

Preparation of pJM7, a vector for surface expression of CtxB.

pJM7 contains a gene fusion (FP59) of cholera toxin B and the AIDA linker/ú-barrel region. This gene fusion is expressed constitutively under the control of the artificial promoter PTK (Klauser et al., EMBO J. 9 (1990) 1991–1999) in a vector with high copy number. The ctxB gene was amplified by PCR using the oligonucleotides EF16 and JM6 from the plasmid pTK1 (Klauser et al. EMBO J. 9 (1990) 1991–1999). The autotransporter consisting of the ú-barrel and the linker region from AIDA-I was amplified by amplification using the oligonucleotides JM1 and JM7 from a plasmid DNA preparation from E. coli EPEC 2787 (Benz and Schmidt, Infect. Immun. 57 (1989), 1506–1511). The oligonucleotide JM1 contains in its 5' projection a BglII recognition sequence, and oligonucleotides JM6 and JM7 each contain a KpnI recognition sequence. The vector DNA (pBA) was hydrolysed with ClaI and BamHI, and the two PCR products were then, following the amplification, cut with ClaI and KpnI (EF16/JM6 fragment) or with BglII and KpnI (JM7/JM1 fragment). The three fragments generated in this way were condensed in a ligation.

FIG. 3b:

Preparation of pJM22, a vector for surface expression of peptides.

pJM22 produces the fusion protein FP50 which consists of three domains. At the N-terminal end there is located the CtxB signal sequence which ensures export of the resulting fusion protein through the cell membrane (Sec mediator). This is followed by the passenger domain, in this case a peptide, the epitope PEYFK. At the C-terminal end of the fusion protein is the AIDA ú-barrel/linker region, the autotransporter, which conveys the passenger domain with N-terminal truncation by the signal peptide to the surface of E. coli. To construct pJM22, firstly the DNA of pJM7 was hydrolysed with XhoI, and the vector portion of pJM7 was amplified by PCR using the oligonucleotides JM7 and JM20. This entailed deletion of the ctxB gene apart from its signal sequence. The oligonucleotide JM20 contained in its 5' overhang, in addition to the KpnI cleavage sequence, five codons which code for the amino acids PEYFK. This amino-acid sequence represents a linear epitope for the monoclonal antibody Dü142. The PCR product was hydrolysed with KpnI and then self-ligated.

FIG. 4

Expression detection and protease sensitivity

Because of the strong stable expression of the fusion proteins FP59 (derived from pJM7) and FP50 (derived from pJM22) in E. coli, these can easily be identified in a whole cell lysate stained with Coomassie brilliant blue. Protease accessibility represents a conventional means for determining the location of a protein. Access is to be expected to cell-intrinsic proteins only if these are presented on the outside of the bacterium or if the outer membrane of the bacterium is permeable to proteases. To rule out the latter, it is possible to use a protease-sensitive marker which is known to be naturally present in the periplasm. The integrity of the outer membrane is ensured only if this marker is not attacked by the protease employed. Cells of E. coli UT5600 or JK321 were cultured overnight on LB agar (50 mg/l ampicillin) and suspended in PBS. The cell suspensions were adjusted to an OD578=4.0. Cells from 0.5 ml of cell suspension were sedimented for 1 min in a bench centrifuge and resuspended in 200 µl of PBS with 0.1 mg/ml protease. The mixtures were incubated at 37° C. for 20 min and stopped by cooling to 0° C., sedimenting for 1 minute and resuspending the pellet in 40 µl of SDS-PAGE sample buffer and immediately boiling for 15 minutes. The evaluation took place after SDS-PAGE by Western blotting (4b and 4c) or by staining with Coomassie brilliant blue (4a). Access of the proteases to the periplasm was ruled out by employing not only antisera specific for the passenger protein domains but also an antiserum specific for the C-terminal part of OmpA, which is naturally present inaccesibly in the periplasm and ought therefore not be capable of being attacked by externally added proteases such as trypsin (4c).

FIG. 4a:

SDS-PAGE and subsequent staining with Coomassie brilliant blue to detect protease sensitivity and quantify expression. Whole cell lysates of E. coli JK321 and E. coli UT5600 were loaded.

| Lane 1 | JK321 pJM7 C * |
| Lane 2 | JK321 pJM7 T** |
| Lane 3 | JK321 pJM7 -*** |
| Lane 4 | Molecular weight markers (94, 67, 43, 30, 20 and 14 kDa) |
| Lane 5 | JK321 pJM22 C |
| Lane 6 | JK321 pJM22 T |
| Lane 7 | JK321 pJM22 - |
| Lane 8 | JK321 pTK61 C |
| Lane 9 | JK321 pTK61 T |
| Lane 10 | JK321 pTK61 - |
| Lane 11 | UT5600 pJM7 C |
| Lane 12 | UT5600 pJM7 T |
| Lane 13 | UT5600 pJM7 - |
| Lane 14 | Molecular weight markers (94, 67, 43, 30, 20 and 14 kDa) |
| Lane 15 | UT5600 pJM22 C |
| Lane 16 | UT5600 pJM22 T |
| Lane 17 | UT5600 pJM22 - |
| Lane 18 | UT5600 pTK61 C |
| Lane 19 | UT5600 pTK61 T |
| Lane 20 | UT5600 pTK61 - |

C * Cells were digested with chymotrypsin
T** Cells were digested with trypsin
-*** Native cells

FIG. 4b:

Western blot for detecting expression and protease sensitivity

Whole cell lysates of E. coli JK321 and E. coli UT5600 were loaded. After the electrophoresis, the proteins were transferred from the gel by the semi-dry method to a nitrocellulose membrane. The filters were then blocked with blocking solution (PBS with 0.5% Tween 20 and 0.5 M NaCl) for 10 min, and the first antiserum, AK55 (rabbit anti-cholera toxin B) diluted 1:200 in blocking solution, was added. To detect the epitope PEYFK, the hybridoma supernatant Dü142, diluted 1:35 in blocking solution, was added. The filters were incubated with the primary antibodies for 1 h, then washed three times and incubated with protein A-alkaline phosphatase conjugate (1:500 in blocking solution) for 30 min. The filters were developed with NBT/BCIP colour solution.

| Lane 1 | JK321 pJM7 C * |
| Lane 2 | JK321 pJM7 T** |
| Lane 3 | JK321 pJM7 -*** |
| Lane 4 | Molecular weight markers (106, 80, 50, 32, 27 and 18 kDa) |

-continued

| Lane 5 | JK321 pJM22 C |
| Lane 6 | JK321 pJM22 T |
| Lane 7 | JK321 pJM22 - |
| Lane 8 | JK321 pTK61 C |
| Lane 9 | JK321 pTK61 T |
| Lane 10 | JK321 pTK61 - |
| Lane 11 | UT5600 pJM7 C |
| Lane 12 | UT5600 pJM7 T |
| Lane 13 | UT5600 pJM7 - |
| Lane 14 | Molecular weight markers (106, 80, 50, 32, 27 and 18 kDa) |
| Lane 15 | UT5600 pJM22 C |
| Lane 16 | UT5600 pJM22 T |
| Lane 17 | UT5600 pJM22 - |
| Lane 18 | UT5600 pTK61 C |
| Lane 19 | UT5600 pTK61 T |
| Lane 20 | UT5600 pTK61 - |

C * Cells were digested with chymotrypsin
T** Cells were digested with trypsin
-*** Native cells

FIG. 4c:

Demonstration of the integrity of the outer membrane by Western blot analysis.

Whole cell lysates of *E. coli* JK321 and *E. coli* UT5600 were loaded. After the electrophoresis, the proteins were transferred from the gel by the semi-dry method to a nitrocellulose membrane. The filters were then blocked with blocking solution (PBS with 0.5% Tween 20 and 0.5 M NaCl) for 10 min, and the first antiserum, K56 (rabbit anti-OmpA) diluted 1:1000 in blocking solution, was added. The filters were incubated with the primary antibodies for 1 h, then washed three times and incubated with protein A-alkaline phosphatase conjugate (1:500 in blocking solution) for 30 min. The filters were developed with NBT/BCIP colour solution. OmpA is an outer membrane protein of *E. coli* with a C-terminal periplasmic portion. This periplasmic part is trypsin-sensitive. If trypsin has access to the periplasm, a part about 10–11 kDa in size is digested off mature OmpA (35 kDa). Digestion would thus result in a displacement of the OmpA band in the Western blot from 35 kDa to 25 kDa (Klauser et al., EMBO J. 9 (1990) 1991–1999), which is obviously not the case on use of the AIDA-I autotransporter for transporting recombinant proteins.

| Lane 1 | JK321 pTK1 T* |
| Lane 2 | JK321 pJM7 T |
| Lane 3 | JK321 pJM22 T |
| Lane 4 | JK321 pTK61 T |
| Lane 5 | Molecular weight markers (106, 80, 50, 32, 27 and 18 kDa) |
| Lane 6 | JK321 pTK1 -** |
| Lane 7 | JK321 pJM7 - |
| Lane 8 | JK321 pJM22 - |
| Lane 9 | JK321 pTK6l - |
| Lane 10 | empty |
| Lane 11 | UT5600 pTK1 T* |
| Lane 12 | UT5600 pJM7 T |
| Lane 13 | UT5600 pJM22 T |
| Lane 14 | UT5600 pTK61 T |
| Lane 15 | Molecular weight markers (106, 80, 50, 32, 27 and 18 kDa) |
| Lane 16 | UT5600 pTK1 -** |
| Lane 17 | UT5600 pJM7 - |
| Lane 18 | UT5600 pJM22 - |
| Lane 19 | UT5600 pTK61 - |

T* Cells were digested with trypsin
-** Native cells

FIG. 5

Immunofluorescence

Immunofluorescence of whole, non-permeabilized cells represents a conventional method for detecting determinants exposed on the cell surface. Antibodies employed therein for detecting the determinants are too large to pass through the intact outer membrane. The control used for differentiation and for estimation of the background activity of periplasmically or cellularly expressed determinants comprises antibodies against antigens known to be expressed periplasmically or cellularly respectively.

Cells of *E. coli* UT5600 which contain one of the plasmids pBA, pTK1, pTK61, pJM7 or pJM22 were cultured overnight on LB agar (ampicillin 50 mg/l) and suspended in PBS to an optical density of 0.1 at 578 nm. 500 µl of this cell suspension were used to coat cover glasses which were placed in 24-well microtitre plates. The cells were sedimented onto the cover glasses in a plate centrifuge for 5 min. 450 µl of the supernatant were aspirated off and replaced by PBS with 2.5% PFA (paraformaldehyde), with which fixation was carried out for 20 min. The supernatant was completely aspirated off and three washes with 500 µl of PBS were carried out. Nonspecific binding sites were blocked by incubation with 300 µl of PBS containing 1% FCS for 5 min. The blocking solution was completely aspirated off, and the cover glasses were centred in their wells, covered with 15 µl of a 1:100 dilution of the rabbit serum AKS5 (raised against cholera toxin B) and incubated in a humidity chamber at room temperature for 1 h. This was followed by three washes with 500 µl of PBS each time, blocking with 350 µl of PBS/FCS for 5 min, and incubation with 15 µl of 1:100 dilution of a goat anti-rabbit-Texas red conjugate for 30 min. After a subsequent three washes, the cover glasses were placed on slides and embedded using embedding medium. The result of the immunofluorescence was assessed under the microscope and recorded by photography with exposure times of equal length.

a) *E. coli* UT5600 pBA (strain used as negative control containing only the cloning vector without insert)
b) *E. coli* UT5600 pTK1 (produces cholera toxin B which is exported into the periplasm. This construct is used for determining the background activity of the periplasmically expressed cholera toxin B).
c) *E. coli* UT5600 pJM7 (expresses FP59, the fusion protein of AIDA and cholera toxin B, which is presented on the surface of *E. coli*).
d) *E. coli* UT5600 pJM22 (expresses FP50, the fusion protein of AIDA and the epitope PEYFK. This construct is used to demonstrate that the AIDA portion of FP59 and FP50 shows no cross-reactivity with the AK55 used in this experiment).
e) *E. coli* UT5600 pTK61 (produces a fusion protein of cholera toxin B and Iga-ü which is presented on the surface of *E. coli* (Klauser et al., EMBO J. 9 (1990) 1991–1999). Used for comparison with the AIDA construct FP59).

FIG. 6. DNA sequences of the oligonucleotides used (SEQ ID NOS: 1–5)

FIGS. 7–24

DNA sequence (non-coding strand) and amino-acid sequences derived therefrom, of bacterial autotransporters.

FIG. 7. Depiction of the membrane-integrated part of the AIDA-I autotransporter from *Escherichia coli* (SEQ ID NOS: 6 and 7). (Benz and Schmidt, Mol. Microbiol. 6 (1992), 1539–1546).

FIG. 8. Depiction of the membrane-integrated part of the BrkA autotransporter from *Bordetella pertussis* (SEQ ID NOS: 8 and 9). (Fernandez and Weiss, Infect Immun. 62 (1994), 4727–4738).

FIG. 9. Depiction of the membrane-integrated part of the Hap autotransporter from *Haemophilus influenzae* (SEQ ID NOS: 10 and 11). (StGeme et al., Mol. Microbiol. 14 (1994), 217–233).

FIG. 10. Depiction of the membrane-integrated part of the Hsr autotransporter from *Helobacter mustelae* (SEQ ID NOS: 12 and 13). (O'Toole et al., Mol. Microbiol 11 (1994), 349–361).

FIG. 11. Depiction of the membrane-integrated part of the IcsA autotransporter from *Shigella flexneri* (SEQ ID NOS: 14 and 15). (Goldberg et al., J. Bacteriol 175 (1993), 2189–2196).

FIG. 12. Depiction of the membrane-integrated part of the Prn (outer membrane protein P96) autotransporter from *Bordetella pertussis* (SEQ ID NOS: 16 and 17). (Charles et al., Proc. Natl. Acad. Sci. USA 86 (1989), 3554–3558).

FIG. 13. Depiction of the membrane-integrated part of the Prn (P70 pertactin) autotransporter from *Bordetella parapertussis* (SEQ ID NOS: 18 and 19). (Li et al., J. Gen. Microbiol. 138 (1992), 1697–1705).

FIG. 14. Depiction of the membrane-integrated part of the 190 kDA cell surface antigen autotransporter from *Rickettsia rickettsii* (SEQ ID NOS: 20 and 21). (Anderson et al., unpublished, Genbank Accession No. M31227).

FIG. 15. Depiction of the membrane-integrated part of the SpaP autotransporter from *Rickettsia prowazekii* (SEQ ID NOS: 22 and 23). (Carl et al., Proc. Natl. Acad. Sci. USA 87 (1990), 8237–8241).

FIG. 16. Depiction of the membrane-integrated part of the 120 kilodalton outer membrane protein (rOmp B) autotransporter from *Rickettsia rickettsii* (SEQ ID NOS: 24 and 25). (Gilmore et al., Mol. Microbiol. 5 (1991), 2361–2370).

FIG. 17. Depiction of the membrane-integrated part of the SlpT autotransporter from *Rickettsia typhi*(SEQ ID NOS: 26 and 27). (Hahn et al., Gene 133 (1993), 129–133).

FIG. 18. Depiction of the membrane-integrated part of the SepA autotransporter from *Shigella flexneri* (SEQ ID NOS: 28 and 29). (Benjellou-Toumi et al., Mol. Microbiol.17 (1995), 123–135).

FIG. 19. Depiction of the membrane-integrated part of the Ssp autotransporter from *Serratia marcescens* RH1 (SEQ ID NOS: 30 and 31). (Roh, unpublished, Genbank Accession No. X59719).

FIG. 20 Depiction of the membrane-integrated part of the Ssp autotransporter from *S. marcescens* IFO-3046, clone pSP11 (SEQ ID NOS: 32 and 33). (Yanagida, et al. J. Bacteriol. 166 (1986), 937–944).

FIG. 21. Depiction of the membrane-integrated part of the Ssp-h1 autotransporter from *Serratia. marcescens*, strain IFO3046 (SEQ ID NOS: 34 and 35). (Onishi and Horinouchi, unpublished, Genbank Accession No. D78380).

FIG. 22. Depiction of the membrane-integrated part of the Ssp-h2 autotransporter from *Serratia. marcescens*, strain IFO3046 (SEQ ID NOS: 36 and 37). (Onishi and Horinouchi, unpublished, Genbank Accession No. D78380).

FIG. 23. Depiction of the membrane-integrated part of the Tsh autotransporter from *Escherichia coli* (SEQ ID NOS: 38 and 39). (Provence et al., Infect. Immun. 62 (1994), 1369–1380).

FIG. 24. Depiction of the membrane-integrated part of the VacA autotransporter from *Helicobacter pylori* (SEQ ID NOS: 40 and 41). (Schmitt and Haas, Mol. Microbiol. 12 (1994), 307–319). At least 3 other forms of VacA are also known in *Helicobacter pylori*, but they differ in the stated region to an inconsiderable extent.

DETAILED DESCRIPTION OF THE INVENTION

It is surprisingly possible by using a host bacterium which is homologous relative to the nucleic acid section coding for the transporter domain to achieve a surface presentation of peptides or and polypeptides, in particular including short synthetic peptides with a length of, preferably, 4–50 amino acids or of eukaryotic polypeptides, which is distinctly improved by comparison with the prior art.

In the process according to the invention there is provision of a host bacterium which is transformed with one or with a plurality of compatible recombinant vectors. A vector of this type contains, operatively linked to a promoter and, where appropriate, other sequences necessary for expression, a fused nucleic acid sequence. This fused nucleic acid sequence comprises (i) a signal peptide-encoding section, preferably a section which codes for a Gram-negative signal peptide which makes passage through the inner membrane into the periplasm possible. The fused nucleic acid sequence (ii) also comprises a section coding for the passenger peptide or polypeptide to be presented. A nucleic acid section coding for a protease recognition site is, where appropriate, located on the 3' side of this section (iii). Examples of suitable protease recognition sites are recognition sites for intrinsic, that is to say naturally present in the host cell, or externally added proteases. Examples of externally added proteases are the IgA protease (compare, for example, EP-A-0 254 090), thrombin or factor X. Examples of intrinsic proteases are OmpT, OmpK or protease X. On the 3' side of this section there is located (iv) a nucleic acid section coding for a transmembrane linker, which makes presentation of the peptide or polypeptide encoded by section (iii) on the outside of the outer membrane of the host bacterium possible. On the 3' side of this section is a nucleic acid section coding for a transporter domain of an autotransporter.

The transmembrane linker domains particularly preferably used are homologous in relation to the autotransporter, that is to say the transmembrane linker domains are encoded by nucleic acid sections directly on the 5' side of the autotransporter domains. The length of the transmembrane linkers is preferably 30–16 amino acids.

The transporter domain is able to form a so-called ú-barrel in the outer membrane of the host bacterium. The ú-barrel consists of an even number of antiparallel, amphipatic, ú-pleated sheets. This structure has, like other proteins of the outer membrane of Gram-negative bacteria, an aromatic amino acid such as phenylalanine or tryptophan at the C terminus. This is followed alternately by charged (polar) and uncharged (hydrophobic) amino acids, and this structure appears to play a part in the folding with the membrane. The number and location of the amphipatic, ú-pleated sheets can be identified with the aid of a suitable computer program and be used, with the aid of analogies to the outer membrane porins whose crystal structure is known (Cowan et al., Nature 358 (1992) 727–733), for constructing a model of the barrel structure. The barrel structure is preferably constructed as follows: 9–14, in particular about 12 amino acids (AA) for a membrane passage; no or a minimal number of charged AA point outwards in a ú-pleated sheet; small loops, or none at all, point inwards, where appropriate large or very large loops point outwards; the ú-barrel is composed of 12, 14, 16 or 18, in particular 14, antiparallel ú-pleated sheets.

Starting from the model of the barrel, it is now possible for the region necessary for self-transport through the outer membrane to be established and linked by a signal peptide and a passenger domain at the genetic level. Expression of this construct then makes transport of the passenger protein to the bacterial surface possible, it being possible for the signal peptide to derive originally from the passenger or from another protein. It must be taken into account in this connection that a linker region which is of suitable length and sequence and which extends through the pore which has formed and ensures that the passenger domains are completely exposed on the surface is also linked properly to the ú-barrel.

An essential feature of the process according to the invention is that the host bacterium is homologous relative to the nucleic acid section coding for the transporter domain, that is to say the host cell and the transporter domain are selected from homologous families, for example enterobacteria, preferably from homologous genera, for example *escherichia, salmonella*, or *helicobacter*, particularly preferably from homologous species, for example *Escherichia coli, Salmonella typhimurium*. It is particularly preferred to use *salmonella* or *E. coli* as host bacterium and a transporter domain which is likewise derived from *salmonella* or *E. coli*, or a variant thereof.

A particularly suitable *E. coli* host strain which may be mentioned here is the strain JK321 (DSM 8860) which is ompT⁻, dsbA⁻ and carries the genetic marker fpt, which leads to stable surface expression even of large proteins such as, for example, the $V_h$ chain of an antibody with the aid of the iga<sub>ú</sub> helper protein.

In a preferred embodiment, the present invention therefore relates to a carrier protein which performs an autotransporter function and makes surface exposure of recombinant proteins possible in *Escherichia coli* with high yield. In a typical example, this is the autotransporter of the "adhesin involved in diffuse adherence" (AIDA-I) from *E. coli* (Benz and Schmidt, Infect. Immun. 57 (1989), 1506–1511). The transporter domain of the AIDA-I protein is depicted in FIG. 2. Besides this specific sequence, it is also possible to use variants thereof which can be produced, for example, by modifying the amino-acid sequence in the loop structures not involved in the membrane passage. It is also possible, where appropriate, for the nucleic acid sections coding for the surface loops to be completely deleted.

It is also possible within the amphipatic ú-pleated sheet structures to carry out conservative amino acid exchanges, that is to say replacement of one hydrophilic by another hydrophilic amino acid or/and replacement of one hydrophobic by another hydrophobic amino acid. A variant preferably has a homology of at least 80% and, in particular, at least 90% with the sequence, indicated in FIG. 2, of the AIDA-I autotransporter domain, at least in the region of the ú-pleated sheet structures.

In another typical example, the autotransporter used is that of the SepA protein from *Shigella flexneri* (Benjellou-Touimi et al., Mol. Micobiol 17 (1995) 123–135) or a variant thereof. In another typical example, it is the autotransporter of the IcsA protein from *Shigella flexneri* (Goldberg et al., J. Bacteriol 175 (1993), 2189–2196) or of the Tsh protein from *E. coli* (Provence et al., Infect. Immun 62 (1994), 1369–1380). In another typical example, it is the autotransporter of the Hsr protein from *Helicobacter mustelae* (O'Toole et al., Mol. Microbiol. 11 (1994), 349–361), of the Prn protein from *Bordetella* ssp. (Charles et al., Proc. Natl. Acad. Sci USA 86 (1989), 3554–3558; Li et al., J. Gen. Microbiol. 138 (1992), 1697–1705), of the Ssp protein from *Serratia marcescens* (for example in Yanagida et al., J. Bacteriol. 166 (1986), 937–944 or Genbank Accession No. X59719, D78380), of the Hap protein from *Haemophilus influenzae* (StGeme et al., Mol. Microbiol. 14 (1994), 217–233), of the BrkA protein from *Bordetella pertussis* (Fernandez and Weiss, Infect. Immunol. 62 (1994), 4727–4738), of the VacA protein from *Helicobacter pylori* (Schmitt and Haas, Mol. Microbiol. 12 (1994), 307–319) or various rickettsial proteins (for example 190 kDa cell surface antigens, Genbank Accession No. M31227; SpaP, Carl et al., Proc. Natl. Acad. Sci. USA 87 (1990), 8237–8241; rOmpB, Gilmore et al., Mol. Microbiol. 5 (1991), 2361–2370 and Slp T, Hahn et al., Gene 133 (1993), 129–133) or a variant thereof as defined above.

The DNA sequences, and the amino-acid sequences derived therefrom, of the aforementioned auto-transporters are depicted in FIGS. 7–24.

Further autotransporter domains in bacterial surface proteins or in secreted bacterial proteins may be derived from protein sequences present in data banks from in protein sequences which are based on DNA sequences available in data banks, or from protein sequences determined by sequence analysis directly or indirectly via the DNA sequence. The corresponding coding regions (genes) can be used to prepare vectors or fusion protein genes which make efficient surface expression of passenger proteins possible in Gram-negative bacteria, especially *E. coli*.

Surface presentation or exposure means according to the invention that the fusion proteins or passenger domains are located on the side of the outer bacterial membrane facing the medium. In intact Gram-negative bacteria, passenger proteins exposed on the surface are freely accessible to binding partners.

In a preferred embodiment, the present invention thus makes possible the surface presentation of peptides or, in another embodiment, the surface presentation of peptide libraries in Gram-negative bacteria, especially in *E. coli*, and the use thereof for determining the affinity for an antibody or another receptor or for epitope mapping. Epitope mapping means that the peptide with the greatest affinity for an antibody or another receptor is identified exposed on the surface of the producing strain. This makes clear a crucial advantage of the present invention by comparison with previously used phage systems (Makowski, Gene 128, (1953), 5–11) for expressing peptide libraries. In the bacterial system according to the invention, identification of a peptide having the required properties takes place simultaneously with the selection of the clonal producer. The latter can be grown directly and used to produce larger amounts of the required peptide without the need for the elaborate cycles of infection (phage replication) and selection (phage selection) as with the phage system. The growing of the strain expressing the correct peptide exposed on the surface takes place over the same time as amplification of the corresponding coding gene, sequence analysis of which permits unambiguous identification and characterization of the peptide with simple and established techniques. These advantages according to the invention apply to all passenger domains expressed exposed on the surface using the present invention, that is to say peptides and polypeptides.

A peptide library produced according to the invention thus contains fusion proteins composed of an autotransporter, in a particularly preferred embodiment of the AIDA autotransporter, and of a peptide which is produced, exposed on the surface, in a Gram-negative bacterium, preferably *E. coli*. The wide variety of different expressed peptides results in a typical example from the cloning of degenerate, synthetically prepared oligonucleotides between the coding regions for the signal peptide and the autotransporter.

In another preferred embodiment, the present invention makes it possible to express proteins or protein fragments acting as antigen on the surface of Gram-negative bacteria, preferably *E. coli*. The construction of a fusion protein of this type takes place according to the invention using the ú subunit of the toxin *Vibrio cholerae* (CtxB) as passenger and the AIDA autotransporter as carrier protein. The accessibility of the surface-exposed antigenic domains for suitable binding partners has been demonstrated according to the invention by labelling with an antiserum specific for CtxB. It emerged from this that the recombinant fusion proteins embedded in the outer membrane of the *E. coli* host strain may comprise up to 5% of the total cell protein, which means a considerably improved efficiency by comparison with other systems. The process described here thus makes possible the stable production and presentation of proteins or protein fragments having antigenic activity on the surface of Gram-negative bacteria and, in a preferred embodiment, the use thereof as live vaccine, for oral vaccination or for screening sera or antibody banks. The use of bacterial cells, for example attenuated *salmonella* strains (Schorr et al., Vaccine 9 (1991) 675–681) with proteins which have antigenic activity and are expressed exposed on the surface has proved advantageous in live vaccination by comparison with the intracellular bacterial expression of antigens.

The present invention generally permits, in a preferred embodiment, the surface expression of all passengers which are in their essential constituent peptides or proteins on the surface of Gram-negative bacteria, in particular *E. coli*.

In another preferred embodiment, the C-terminal domain of the AIDA protein, the AIDA autotransporter, serves as membrane anchor for the presentation of recombinant polypeptides of the immune system, for example recombinant antibody domains on the surface of Gram-negative bacteria. Surface expression of recombinant antibody fragments makes it possible to modify them rapidly and to assess and investigate their antigen-binding properties. Thus, it becomes possible to produce whole libraries of functional antibody fragments exposed on the surface, and to test them for particular given binding properties or affinities. The advantage of the present invention by comparison with previously used phage systems is that the variation, that is to say the genetic manipulation and the production of the protein, can take place in the same host organism. It is moreover possible for the genetic manipulation to be targeted (site-specific mutagenesis) or random, using degenerate oligonucleotides to synthesize an intact fusion of antibody-encoding fragment as passenger and the autotransporter as carrier protein. It is likewise possible for the genetic manipulation to take place in the form of in vivo mutagenesis by exposing the bacteria which contain the gene for the fusion protein to high-energy radiation (for example UV) or chemical agents having mutagenic effects.

The selection, according to the invention, of the molecule having the correct binding properties takes place alongside the selection of the producing bacterial cell. It is evident from this that this procedure according to the invention, in its strategy consisting of variation and subsequent selection, is based on the natural strategy of the immune system for the best possible adaptation of binding properties of immunogenic molecules. Various procedures according to the invention are conceivable for expressing functional antigen-binding parts of antibodies, which are not usually glycosylated, on the surface of Gram-negative bacteria, preferably *E. coli*. Two monovalent fragments can be presented together through separate fusions of the light chain (VL) and the heavy chain (VH) with, in each case, an autotransporter domain, which are expressed independently of one another with different compatible vectors or under the control of different promoters on the same vector in a host cell. The two antibody domains which are present exposed on the surface assemble to form a functional Fv fragment on the surface, it being possible for the stability of the interaction to be promoted by chemically induced disulphite bridge formation or another type of chemical crosslinking.

In another procedure according to the invention there is preparation of fusion proteins which contain the autotransporter as carrier protein, and as passenger the light chain (VL) and the heavy chain (VH) of an antigen-binding domain of an antibody, linked via a short linker peptide (for example [Gly$_4$Ser]$_3$) which permits correct assembly of the two chains to form a functional Fv fragment. For construction of such single-chain (sc) Fv fragments, it is possible both to link the N terminus of the light chain to the C terminus of the heavy chain, and to link the N terminus of the heavy chain to the C terminus of the light chain (Pluckthun Immun. Rev. 130 (1992), 151–188). It is also possible using the procedures described to produce a complete Fab fragment.

In another preferred embodiment, the present invention makes possible the surface-exposed expression of MHC class II molecules in *E. coli*, where appropriate with defined embedded peptides. Two strategies are conceivable for this. In one variant, two different fusion proteins, both of which contain an autotransporter as carrier protein, are expressed on separate compatible vectors or on one vector under the control of different promoters in a host cell. The passenger protein employed is, on the one hand, the α chain of the required MHC class II subtype and, on the other hand, the ú chain of this subtype, to whose N terminus the required peptide can be attached via a linker (Kozono et al., Nature 369 (1994) 151–154).

In the second variant, a passenger protein consisting of the peptide, the ú chain and the α chain is fused to an autotransporter. The α chain and ú chain assemble on the bacterial surface to form a functional MHC molecule, with the peptide being correctly embedded in the binding cavity. The stability of the complex can be assisted by a chemically induced disulphide bridge formation. Variation of the embedded peptide is possible by site-specific mutagenesis or/and by using degenerate oligonucleotide primers in the preparation of the DNA fragments encoding the fusion proteins, as well as by in vivo mutagenesis methods using high-energy radiation or/and chemical mutagens.

Once again, the advantage of the process according to the invention becomes clear. Variation of the binding partner, expression, selection of the molecule having the optimal properties, sequence analysis and stable production can take place in one host strain. This also makes it possible, for example for variants of previously known ligands with improved binding properties to be rapidly characterized, and thus optimization of ligands or receptors.

In another preferred embodiment, the present invention makes possible the surface expression of immunomodulatory receptors such as, for example, CD1, Fc receptor or MHC class I molecules, and specific variation thereof.

In another preferred embodiment, the present invention makes possible the surface expression of T-cell receptors or parts thereof, but also of other surface antigens of eukaryotic cells or cells of the immune system.

In another preferred embodiment, the protein fragments or peptides expressed on the surface are T-cell epitopes which, following uptake of the bacteria by appropriate cell lines or primary cells such as, for example, macrophages, presented as peptides embedded in MHC molecules of class I or II and can serve to stimulate specific T cells.

In a particularly preferred embodiment, the process according to the invention makes possible the surface expression and the variation of a peptide or polypeptide having an affinity for a binding partner, of a ligand, of a receptor, of an antigen, of a toxin-binding protein, of a protein having enzymatic activity, of a nucleic acid-binding protein, of an inhibitor, of a protein having chelator properties, of an antibody or of an antigen-binding domain of an antibody.

The term "binding partner" means according to the invention an element, a molecule, a chemical compound or a macromolecule, where the binding partner and/or the bacterial cells expressing the fusion proteins are in a freely soluble form, bound to a matrix or else associated with a biological membrane.

The term "antigen-binding domain" refers according to the invention to at least the region of an antibody molecule which is sufficient for specific binding of an antigen.

In another preferred embodiment, the present invention makes chemical, physical or/and enzymatic modification of the passenger peptide or polypeptide, or parts thereof, exposed on the surface possible, it being possible for the modification to be a covalent modification, a non-covalent modification, a glycosilation, a phosphorylation or a proteolysis.

The process according to the invention for producing a variant population of peptides exposed on the surface and for identifying bacteria which carry peptides or polypeptides having a particular required property is divided into the following steps:

(1) preparation of one or more fusion genes by cloning the coding sequence of a required passenger in frame with the coding sequence of a transporter domain of an autotransporter and of a signal peptide, it being possible for the individual subfragments to be amplified by PCR or to derive from restriction digestions of other DNA, in at least one vector;
(2) variation of the passenger by mutagenesis, for example by site-specific mutagenesis, using degenerate oligonucleotide primers in the PCR, by chemical mutagenesis or by using high-energy radiation;
(3) introduction of the vector or vectors into host bacteria;
(4) expression of the fusion gene or fusion genes in the host bacteria which present the fusion protein or fusion proteins stably on the surface;
(5) cultivation of the bacteria, for example in liquid culture or on agar plates, to produce the passenger presented stably exposed on the surface or the passengers presented stably exposed on the surface;
(6) where appropriate selection of the bacteria which carry the passenger or passengers having the required properties on the surface, and
(7) where appropriate characterization of a binding partner for the passenger having the optimal properties.

It is moreover possible according to the invention to perform this process several times in order to adapt the properties of the surface-exposed peptide or polypeptide stepwise to the required binding behaviour, or to optimize, in a first step, the binding partner in respect of one property and, in a second step, in respect of one or more other properties. However, it is also possible according to the invention, depending on the required use, to link only a few constituent steps of the process together, in a typical example the constituent steps (1), (3), (4) and (5), but also all other possible combinations.

In a preferred embodiment of this process, the fusion protein contains as carrier protein the autotransporter domain of the AIDA protein or a variant thereof which makes secretion of the fusion protein possible.

In another preferred embodiment of this process, the fusion protein contains as carrier protein the SepA autotransporter or a part thereof, or the IcsA autotransporter or a part thereof, or the Tsh autotransporter or a part thereof, or the Ssp autotransporter or a part thereof, or the Hap autotransporter or a part thereof, or the Prn autotransporter or a part thereof, or the Hsr autotransporter of a part thereof, or the BrkA autotransporter or a part thereof, or the VacA autotransporter or a part thereof or a rickettsial autotransporter or a part thereof, each of which makes secretion of the fusion protein possible.

The expression of multimeric proteins is possible according to the invention by preparing in one cell different fusion proteins which assemble on the surface to form a functional unit.

The short generation time of the bacteria used as host organism makes it possible to have a permanent variation and selection cycle which makes it possible to adapt, in an evolutionary manner, the passenger potein, but also the autotransporter, to given properties. This may involve, in a typical example, the binding affinities between the passenger protein and a binding partner. The isolation of the bacteria having the stably exposed fusion protein takes place, in a preferred embodiment of this process, by binding to an immobilized or/and labelled binding partner, for example a matrix-fixed binding partner, to a binding partner with a fluorescent label, a binding partner labelled with magnetic particles, or a binding partner with a chromogenic label. In another preferred embodiment, the binding partner is modified so that it can be detected in a second step by a binding partner specific for the modification.

Another aim of the present invention is to provide stably expressed fusion proteins or parts thereof or fusion proteins expressed stably on the surface of bacteria, and the use thereof for therapeutic purposes or diagnostic purposes, in pollutant concentration or removal, in the inactivation of toxins, in the mobilization of raw materials, in food production or processing, in detergent production, in the labelling of selected eukaryotic or prokaryotic cells. It is possible according to the invention to use bacteria expressing antibodies or antibody fragments stably on the surface, in a typical example using the AIDA autotransporter as transporter domain, for the production thereof, these antibodies or antibody fragments subsequently being employed, where appropriate after purification, for diagnostic or therapeutic purposes. It would be possible, for example, to use such antibodies or antibody fragments to identify or select specifically cells with particular surface markers, a typical example which may be mentioned here being tumour antigens. In another typical example, the labelled surface markers are receptors, in which case the labelling takes place along with the blocking of the or one of the receptor properties, which makes it possible specifically to inhibit a signal transduction induced or mediated by the receptor, and the cell function associated therewith.

EXAMPLES

Example 1

Identification and Localization of the Autotransporter in a Surface Protein of *Escherichia coli*.

In order to find an autotransporter appropriate for the required use, that is to say adapted to the passenger protein and the host strain to be used, it is necessary to carry out an analysis of the C-terminal amino-acid sequence of a protein under consideration. This may be a protein already identified as surface factor, or else an amino-acid sequence, deposited in a data bank, of a protein of unknown function, or an amino-acid sequence, derived from a DNA sequence deposited in a data bank, of a protein, or the amino-acid sequence, derived from a gene following a sequence analysis, of a protein. The N terminus of the protein ought to contain a signal peptide sequence in order to make transport across the inner membrane possible, and the part integrated into the membrane ought to start at the C terminus with the aromatic amino acid phenylalanine or tryptophan, followed by alternately polar (or charged) and hydrophobic (or aromatic) amino acids. The passenger domain ought to contain few cysteines and no disulphide bridges at all, since it has emerged that this blocks transport of the passenger through the pore which is formed. The hydrophobicity plot ought to indicate an even number of amphipatic ú-pleated sheet structures from which the outer membrane pore is constituted. The amphipatic ú-pleated sheet structures ought to be about about 12 amino acids long and contain a minimum amount of charged amino acids oriented towards the membrane side, with the loops joining the membrane passages containing few amino acids towards the periplasm. Considerably more amino acids can be present towards the outside (medium). The results of this in the hydrophobicity plot are an assembly of the membrane passages in antiparallel pairs with the exception of the first and the last membrane passage, which complete the barrel structure of the pore by assembling together in antiparallel fashion. Based on compliance with these criteria, it is now possible to construct a model of the autotransporter, which can be used to establish the location and extent of the amino acids necessary for the transport. In addition to the amino acids needed for the pore, the fusion protein must also include, for an autotransporter capable of functioning, a so-called linker region which runs from the N terminus, located in the periplasm, of the ú-barrel structure through the pore to the surface, so that the surface exposure of all the passenger domains is completely ensured.

The first aim of the present invention was to provide a system for optimized surface exposure of recombinant proteins in E. coli. This is why an autotransporter was sought in a natural surface protein of E. coli. The choice fell on the adhesin AIDA-I (Adhesin Involved in Diffuse Adherence, Benz and Schmidt Infect. Immun. 57 (1989) 1506–1511), whose sequence was available in data banks. A signal sequence of 49 amino acids at the N terminus was shown according to the invention, while the requirements according to the invention at the C terminus were met by the amino-acid sequence FSYKI (phenylalanine-serine-tyrosin-lysine-isoleucine). The transported domain contained no cysteines, and the hydrophobicity plot (FIG. 1) predicted 14 antiparallel, amphipatic ú-pleated sheet structures. Thus, to form the pore, at least the amino acids from alanine at position 1014 of the complete amino-acid sequence (Benz and Schmidt, Mol. Microbiol. 6 (1992) 1539–1546) up to phenylalanine at position 1286 are necessary (FIG. 2). Additionally selected as linker region were amino acids attached to alanine 1014 on the N-terminal side. The functional autotransporter region selected in this way could then be isolated by PCR from the DNA of the corresponding E. coli EPEC2787 and used to construct a fusion protein.

Example 2

Construction of a Surface-Exposed Fusion Protein Having an Antigenic Determinant as Passenger Protein Based on the assumptions that AIDA-I is an autotransporter and that a gene fusion of any desired passenger and an autotransporter intrinsic to E. coli (namely AIDA-β) ought to be more compatible with E. coli than a gene fusion of the same passenger with a heterologous autotransporter (for example Iga-β), a gene fusion was produced between aida-β and a gene for a passenger protein. In order to ensure transport of the passenger, not only AIDA-β but also a connecting region ("linker") located on the N-terminal side of the β-barrel was cloned.

Figure 3A:
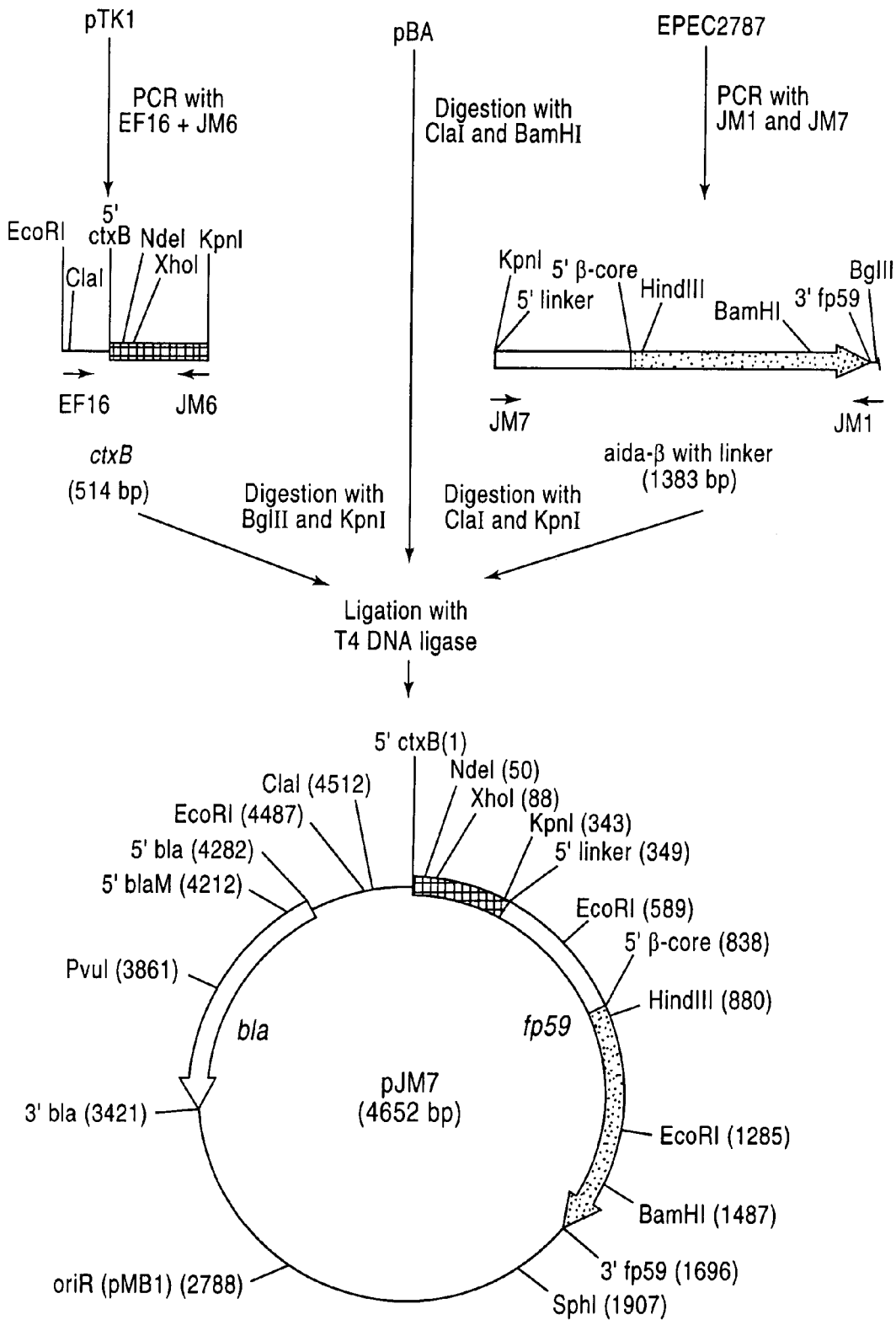

CtxB was selected as passenger, and the corresponding gene from pTK1 (Klauser et al, EMBO J. 9 (1990), 1991–1999) was amplified by PCR using the oligonucleotides EF16 and JM6. Since AIDA-I is plasmid-encoded in E. coli EPEC 2787 (Benz and Schmidt, Infect. Immun. 57 (1989), 1506–1511), the AIDA-I auto-transporter with linker region was likewise amplified from a plasmid preparation of E. coli EPEC 2787 by PCR using the oligonucleotides JM1 and JM7. The two PCR products were digested with restriction enzymes whose recognition sequences were present in the oligo-nucleotides. The two fragments produced in this way were cloned into an appropriately predigested cloning vector (pBA) with high copy number. This resulted in a construct with an artificial constitutive promoter (PTK; Klauser et al., EMBO J. 9 (1990) 1991–1999) in front of a gene fusion consisting of ctxB at the 5' end (coding for amino acids 1–113), followed by an AIDA-I linker (coding for amino acids 116–279 of the fusion protein) and the AIDA-I autotransporter (coding for amino acids 280–563 of the fusion protein) at the 3' end (FIG. 3a). The resulting gene fusion was called FP59.

Figure 4A:
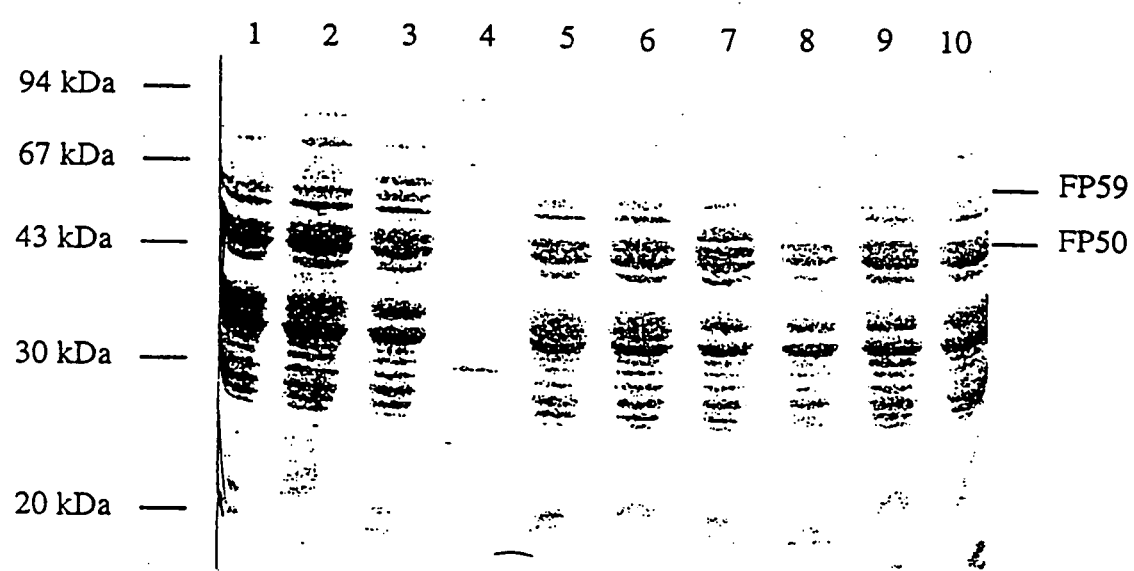
Figure 4A:
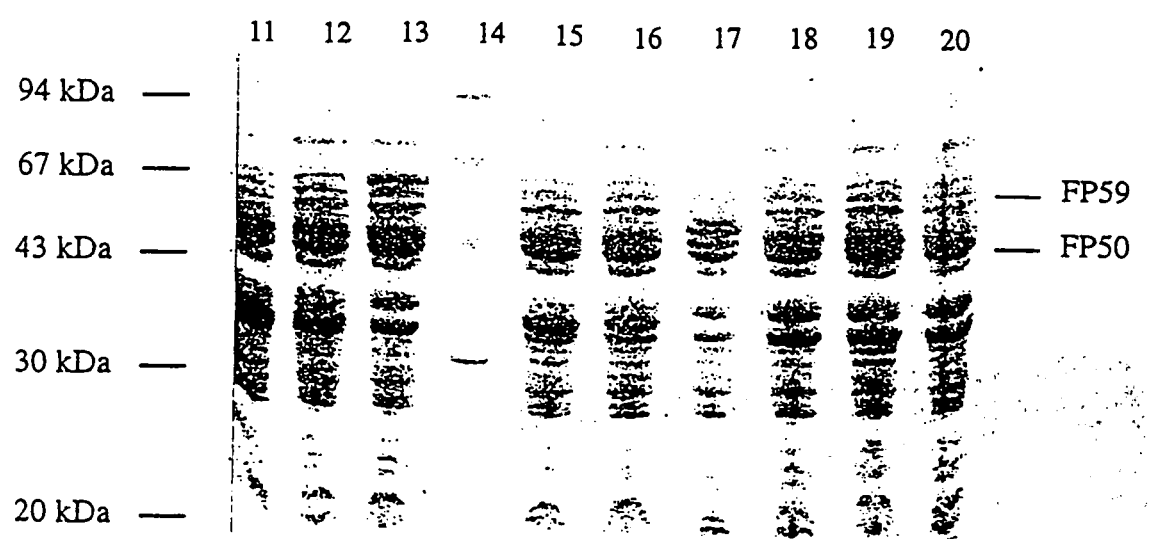

The expression, which was substantially greater than with the previously existing Iga-β system and which was achieved without the tendency to lysis which is to be observed with Iga-β, was unambiguously demonstrated by comparative electrophoresis of whole cell lysates (FIG. 4a).

Figure 4B:
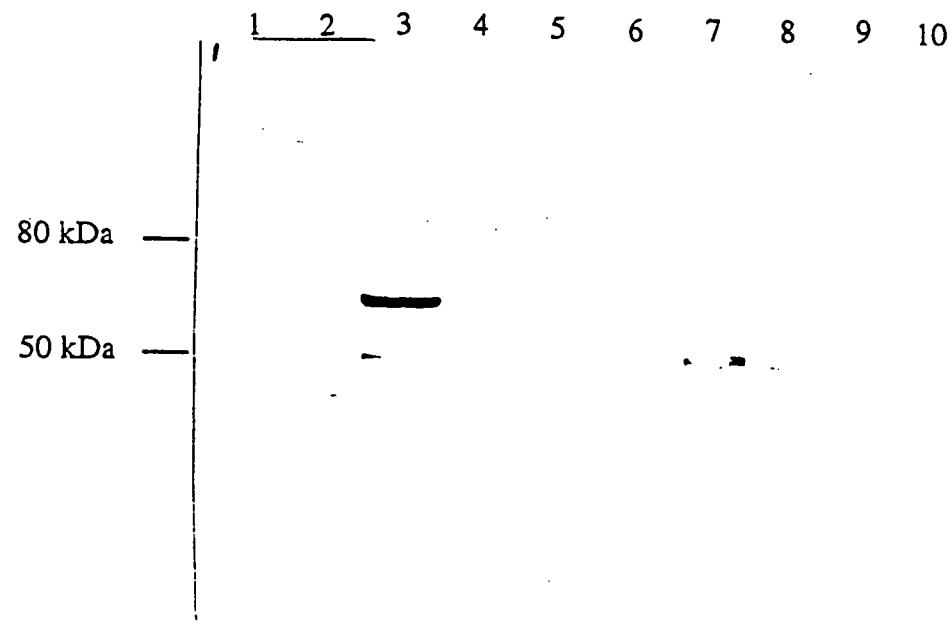
Figure 4B:
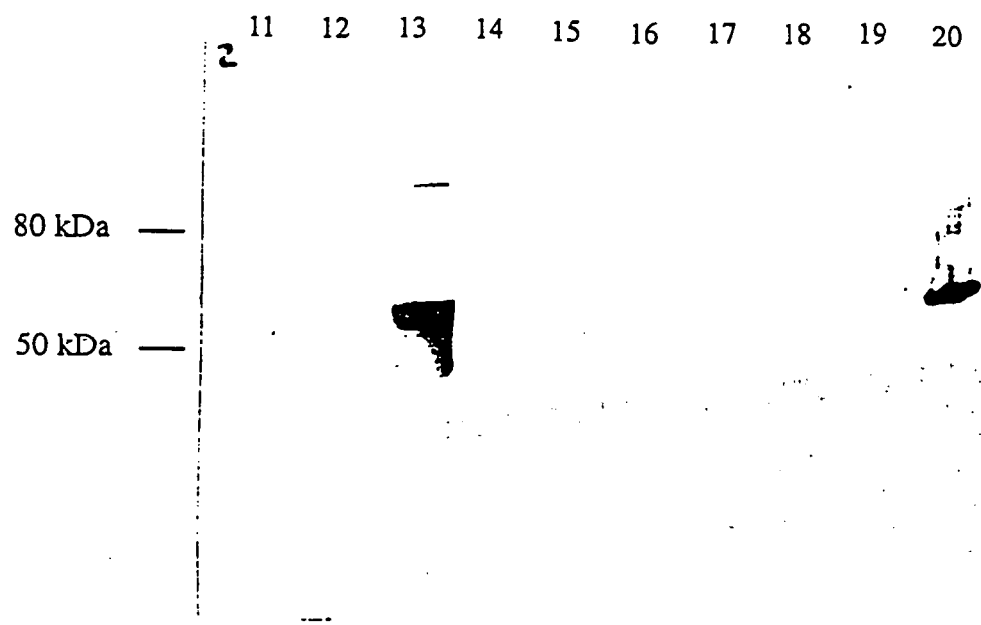

Demonstration of the surface exposure of FP59 was provided by various methods. The protease sensitivity of FP59 was shown in the protein gel by a reduction in the molecular weight following addition of trypsin or chymotrypsin (FIG. 3a). Protease-resistant fragments with, in each case, a mass of about 33–35 kDa were produced (FIG. 3a). These protease-resistant fragments contain no immunogenic portions of the passenger protein. This was shown by Western blot analysis of whole cell lysates using an anti-cholera toxin B serum and comparing with protease-digested and undigested FP59-expressing E. coli (FIG. 4b and comparison of 4a and 4b).

Partial N-terminal sequencing of the membrane-protected trypsin-digested products revealed that the membrane linker region in the AIDA autotransporter has a length of 55 amino acids.

Figure 4C:
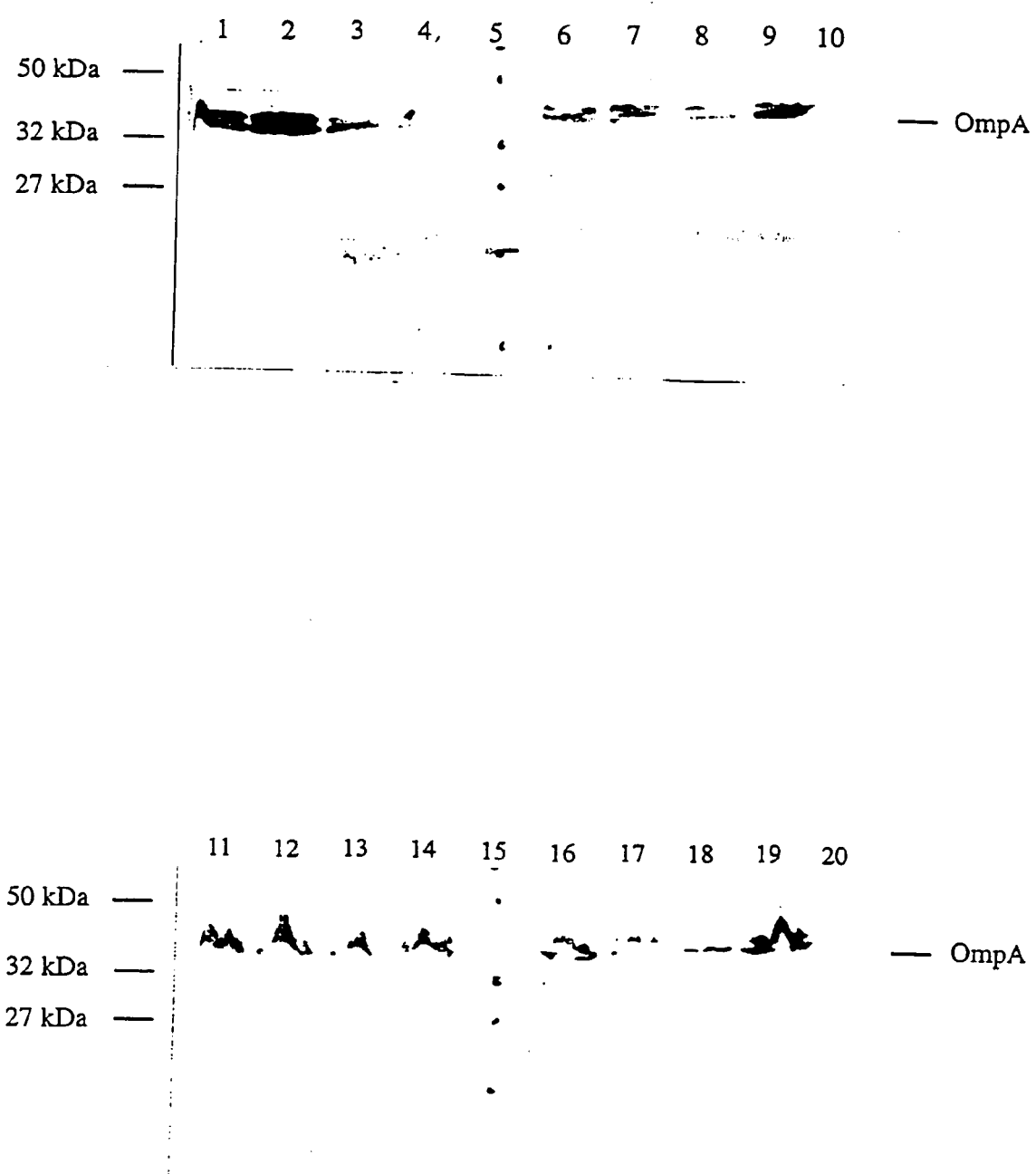

It was also possible with the protease digestions to show the integrity of the outer membrane of FP59-expressing E. coli (FIG. 4c). For this purpose, whole cell lysates were, following the trypsin digestion, developed by immunoblotting with an anti-OmpA serum. Both undigested cells and trypsin-digested cells showed intact OmpA as was to be expected for cells with an intact outer membrane.

Figure 3B:
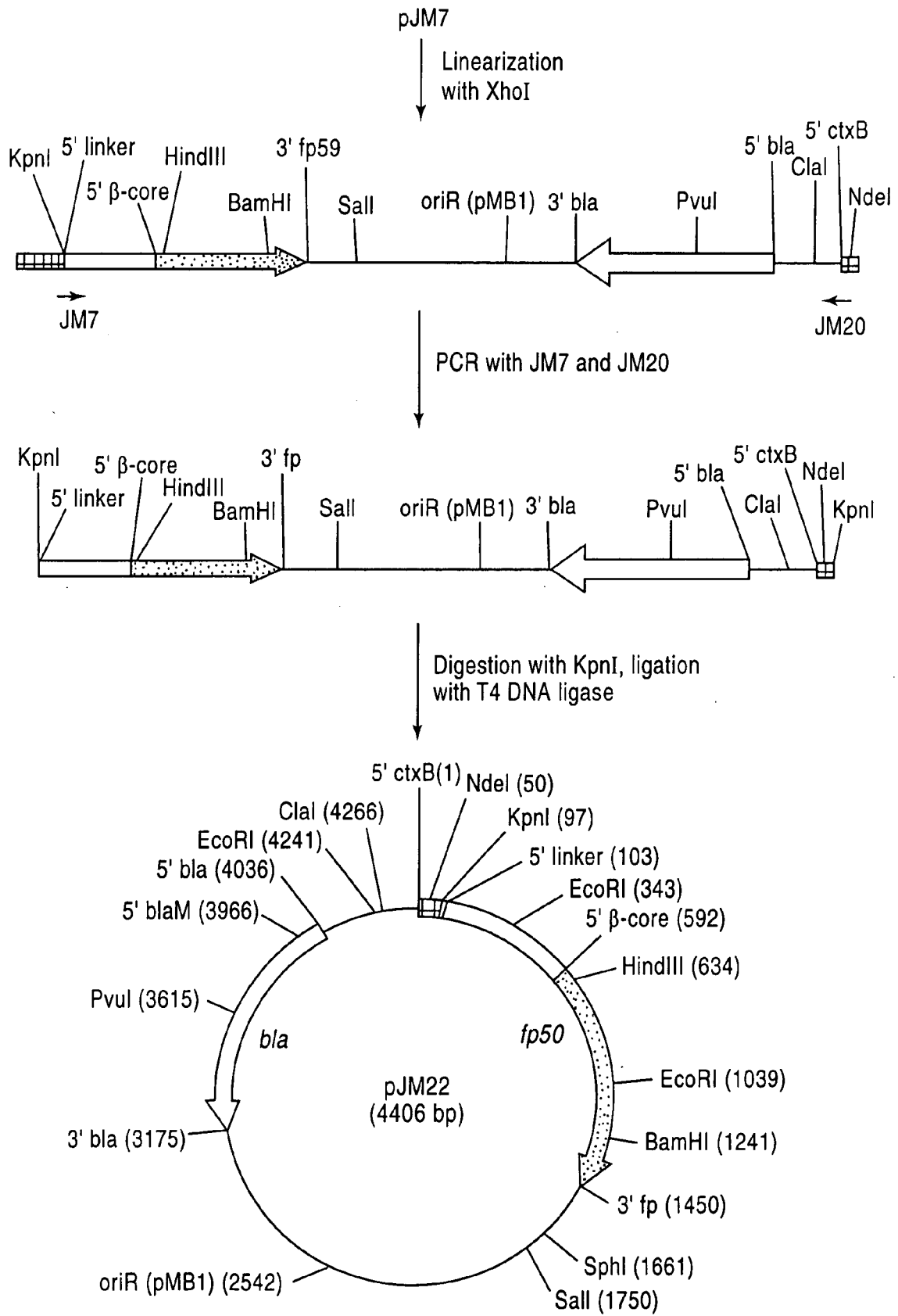
Figure 5:
Figure 5:
Figure 5:
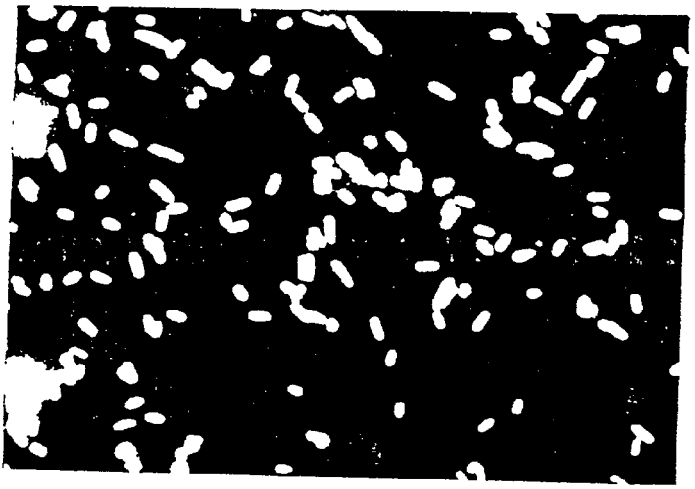

It was also possible to show surface exposure and strong expression of FP59 by immunofluorescence studies (FIG. 5). It is possible by binding fluorescence-labelled antibodies to demonstrate the surface exposure of an antigen on a bacterial cell with an intact outer membrane. This was shown by FP59-expressing E. coli cells by strong fluorescence. The E. coli cells used as negative controls, with peri-plasmically expressed cholera toxin B, with surface-exposed FP50 (FIG. 3b) and with non-recombinant cloning vector were unambiguously negative. The periplasmic cholera toxin B demonstrated the inaccessibility of the periplasm for antibodies (FIG. 5b), and the negative result of the immunofluorescence with FP50 made it possible to rule out cross-reactivity of the antiserum used (against the passenger protein) with the AIDA portions of FP59 (FIG. 5d). The immunofluorescence with the non-recombinant cloning vector was a measure of the background staining intrinsic to the method of measurement (FIG. 5a). This also made it possible to compare the expression of FP59 with B61, the surface-presented cholera toxin B-Iga-β fusion protein produced by pTK61 (FIGS. 5c and 5e), likewise making it possible to demonstrate an unambiguous advantage of the novel system according to the invention.

Example 3

Construction of a Surface-Presented Peptide Fusion

A peptide which acts as linear epitope for a monoclonal antibody (Dü142) was presented and detected on the surface. The peptide was cloned using a PCR-dependent strategy which is extremely suitable for the generation and surface exposure of peptide libraries. This entails formation of a triple gene fusion of the export signal of ctxB (bases 1–81), of a short sequence coding for a peptide (bases 82–96) and of the aida linker/aida-β region (bases 103–1450).

pJM7 (FIG. 3a) was linearized with XhoI and used as template (FIG. 3b) for a PCR with the oligonucleotides JM7 and JM20 (FIG. 6). Both oligonucleotides had a KpnI recognition sequence at their 5' ends [lacuna] JM7 was chosen so that, on use thereof in a PCR, the aida linker/aida-β domains were amplified. JM20 was chosen so that the PCR product contained the signal sequence present in ctxB for the Sec-dependent membrane transport through the cytoplasmic membrane and the six codons subsequent thereto. In addition, JM20 contained in its 5' extension, which was not complementary to the template, five codons which coded for the linear epitope of the antibody Dü142. The KpnI recognition sequence was located upstream of these codons. After the PCR, the resulting product was hydrolysed with KpnI, self-ligated and then transformed into *E. coli*. Correct gene fusions were identified by colony immunoblotting (no figure). Expression and surface exposure were demonstrated in analogy to the methods described in Example 2 by Western blot analysis of protease digests and analysis of protein stainings in the gel (FIGS. 4a, b, c).

The generation of extensive peptide libraries can be done by slightly modifying the cloning strategy described herein. The division described for JM20 of the various functional regions of this oligonucleotide must for this purpose be altered so that the region coding for the linear epitope is replaced by a region which is deliberately subjected to degeneration during the oligonucleotide synthesis. Degeneration means that, in place of defined bases at all position of this functional region, there is replacement of single, multiple or all bases by a base mixture composed of up to four different bases. This means that each codon can code for up to 20 different amino acids, instead of for one amino acid, resulting in a pool of coding sequences which are theoretically possible for all conceivable combinations of amino acids in a peptide of the given length. The cell which carries the peptide having the required property can now be isolated, mediated by binding of the surface-exposed peptide to a binding partner, which, for example, is in a form immobilized on a matrix, has a fluorescent label or is coupled to magnetic beads, and be used for continual production and characterization.

FIG. 1

Hydrophobicity plot
AIDA-I autotransporter
Hydrophobicity
Amino acid position

FIG. 2

Surface
Periplasmic side

FIG. 3a

| PCR with | Digestion with | PCR with |
|---|---|---|
| EF16 + JM6 | ClaI and BamHI | JM1 and JM7 |
| | | aida-β with linker |
| | Digestion with ClaI | Digestion with |
| | and KpnI | BglII and KpnI |
| | Ligation with | |
| | T4 DNA ligase | |

FIG. 3b

Linearization
with XhoI
PCR with JM7 and JM20
Digestion with KpnI, ligation
with T4 DNA ligase

FIGS. 4–24

FIG. 6

DNA sequences of the oligonucleotides used

Name    Use 1)    Length (bp)    Sequence (5'-3')

1) (+) and (−) relate to the coding (+) and the DNA strand complementary thereto (−).

---

The invention claimed is:

1. A process for presenting a passenger peptide or polypeptide on the surface of Gram-negative host bacteria, comprising
   a) providing a host bacterium transformed with a vector encoding a polynucleotide operatively linked to a promoter, wherein said polynucleotide comprises:
   (i) a nucleotide sequence encoding a signal peptide,
   (ii) a nucleotide sequence encoding a passenger peptide or polypeptide,
   (iii) a nucleotide sequence encoding a protease recognition site,
   (iv) a nucleotide sequence encoding a transmembrane linker, and
   (v) a nucleotide sequence encoding a transporter domain of the Adhesin Involved in Diffuse Adherence (AIDA) protein of *E. coli*, wherein the nucleotide sequence encoding the transporter domain is located downstream from the nucleotide sequence encoding the passenger peptide or polypeptide; and
   b) cultivating the host bacterium under conditions for inducing expression of the polynucleotide and presentation of the passenger peptide or polypeptide of (ii) on the surface of the host bacterium, wherein the passenger peptide or polypeptide of (ii) is heterologous in relation to the transporter domain of (v), and the host bacterium is homologous in relation to the transporter domain of (v).

2. The process according to claim 1, wherein the passenger peptide has a length of 4–50 amino acids.

3. The process according to claim 1, wherein the passenger polypeptide is of eukaryotic origin.

4. The process according to claim 3, wherein the passenger polypeptide is an antibody or an antigen-binding domain of an antibody.

5. The process according to claim 3, wherein the passenger polypeptide is the α chain of a Major Histocompatibility Complex (MHC) class II molecule.

6. The process according to claim 3, wherein the passenger polypeptide is the β chain of a MHC class II molecule.

7. The process according to claim 6, wherein the passenger polypeptide is the β chain of a MHC class II molecule comprising an N terminus to which amino acids for binding are attached.

8. The process according to claim 2, wherein libraries of variant passenger peptides or polypeptides are expressed in host cells and presented on the host cell-surface, and wherein each host cell expresses one passenger variant.

9. The process according to claim 8, further comprising selecting single passenger peptides or polypeptides from one of said libraries.

10. A process for obtaining a library of bacteria expressing a variant population of surface-exposed passenger peptides or polypeptides, the process comprising:
    a) providing at least one vector comprising a chimeric gene obtained by cloning in frame, a nucleotide sequence encoding a signal peptide, a nucleotide sequence encoding a passenger peptide or polypeptide, and a nucleotide sequence encoding a transporter domain for an AIDA protein of *E. coli*, wherein the nucleotide sequence encoding the transporter domain is located downstream from the nucleotide sequence encoding the passenger peptide or polypeptide;
    b) mutagenizing the at least one vector to introduce variation into the nucleotide sequence encoding the passenger peptide or polypeptide;
    c) transfecting the at least one vector of step (b) into host bacteria capable of stably presenting the passenger peptide or polypeptide on the cell surface;
    d) expressing the chimeric gene in the host bacteria;

e) culturing the host bacteria of step (d) to produce the passenger peptide or polypeptide stably exposed on the cell surface;

f) selecting the host bacteria of step (e) with a surface-exposed passenger peptide or polypeptide, g) identifying and characterizing a binding partner for the surface-exposed passenger peptide or polypeptide of f), and wherein steps a) to g) are repeated several times in order to obtain the library of bacteria expressing the variant population of surface-exposed passenger peptides or polypeptides.

11. The process according to claim 10, wherein the passenger peptides or polypeptides have an affinity for a binding partner selected from the group consisting of a ligand, a receptor, an antigen, a toxin-binding protein, a protein with enzymatic activity, a nucleic acid-binding protein, an inhibitor, a protein having chelator properties, an antibody and an antigen-binding domain of an antibody.

12. The process according to claim 10, wherein the bacteria expressing the surface-exposed passenger peptides or polypeptides have a binding affinity identified by binding to a labeled or unlabeled immobilized binding partner.

13. The process according to claim 10, comprising introducing a modification into the binding partner of step g) wherein the modification is subsequently detected.

14. The process according to claim 10, wherein the passenger peptides or polypeptides are chemically or enzymatically modified on the bacterial surface.

15. The process according to claim 14, wherein the modification is a non-covalent modification.

16. The process according to claim 14, wherein the modification is a covalent modification.

17. The process according to claim 14, wherein the modification is a glycosylation.

18. The process according to claim 14, wherein the modification is a phosphorylation.

19. The process according to claim 14, wherein the modification is a proteolysis.

20. The process according to claim 19, wherein the passenger peptides or polypeptides are selectively released from the bacterial surface by endogenous or exogenous proteases.

21. The process according to claim 20, wherein the passenger peptides or polypeptides are released by an endogenous protease of the host cell comprising OmpT protease, OmpK protease or protease X.

22. A recombinant vector encoding a chimeric polynucleotide operatively linked to a promoter, the chimeric polynucleotide comprising:

a) a nucleotide sequence encoding a signal peptide, b) a nucleotide sequence encoding a passenger peptide or polypeptide, c) a nucleotide sequence encoding a protease recognition site, d) a nucleotide sequence encoding a transmembrane linker, and e) a nucleotide sequence encoding a transporter domain for an AIDA protein of *E. coli*, wherein the nucleotide sequence encoding the transporter domain is located downstream from the nucleotide sequence encoding the passenger peptide or polypeptide;

wherein the nucleotide sequence encoding the passenger peptide or polypeptide of b) is heterologous in relation to the nucleotide sequence encoding the transporter domain of e).

23. A recombinant Gram-negative host bacterium, wherein the bacterium is transformed with a vector according to claim 22.

24. A recombinant Gram-negative host bacterium transformed with a recombinant vector encoding a chimeric polynucleotide operatively linked to a promoter, the chimeric polynucleotide comprising:

a) a nucleotide sequence encoding a signal peptide, b) a nucleotide sequence encoding a passenger peptide or polypeptide, c) a nucleotide sequence encoding a protease recognition site, d) a nucleotide sequence encoding a transmembrane linker, and e) a nucleotide sequence encoding a transporter domain of the AIDA protein of *E. coli*, wherein the nucleotide sequence encoding the transporter domain is located downstream from the nucleotide sequence encoding the passenger peptide or polypeptide;

wherein the nucleotide sequence encoding the passenger peptide or polypeptide of b) is heterologous in relation to the nucleotide sequence encoding the transporter domain of e), and wherein the host bacterium is homologous in relation to the nucleotide sequence encoding the transporter domain of e).

25. The host bacterium according to claim 24, wherein the bacterium is an *E. coli* cell.

* * * * *

SEQUENCE LISTING (1) GENERAL INFORMATION:

(iii) NUMBER OF SEQUENCES: 41

(2) INFORMATION FOR SEQ ID NO: 1:

(i) SEQUENCE CHARACTERISTICS:
      (A) LENGTH: 36 base pairs
      (B) TYPE: nucleic acid -continued (C) STRANDEDNESS: single
        (D) TOPOLOGY: linear (xi) SEQUENCE DESCRIPTION: SEQ ID NO: 1:

TGTAAAACGA CGGCCAGTAT CACGAGGCCC TTTCGT                          36

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 2:

GGAAGATCTG CCTCAGAAAT GAGGGCC                                    27

(2) INFORMATION FOR SEQ ID NO: 3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 3:

CATGGTACCA GGCGTTTTAT TATTCCCTAC                                 30

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 4:

CGGGGTACCC TTAATCCTAC AAAAGAAAGT                                 30

(2) INFORMATION FOR SEQ ID NO: 5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 5:

AAGGGTACCT TTGAAATACT CCGGAGTAAT ATTTTTGAGG TGTTC                45

(2) INFORMATION FOR SEQ ID NO: 6:

(i) SEQUENCE CHARACTERISTICS:
        (A) LENGTH: 852 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..852

(xi) SEQUENCE DESCRIPTION: SEQ ID NO: 6:

GCA TCC GTG TGG ATG AAG ATC ACT GGA GGA ATA AGC TCT GGT AAG CTT    48
Ala Ser Val Trp Met Lys Ile Thr Gly Gly Ile Ser Ser Gly Lys Leu
 1               5                  10                  15

AAT GAC GGG CAA AAT AAA ACA ACA ACC AAT CAG TTT ATC AAT CAG CTC    96

| | | |
|---|---|---|
| Asn Asp Gly Gln Asn Lys Thr Thr Thr Asn Gln Phe Ile Asn Gln Leu<br>                  20                      25                30 | | |
| GGG GGG GAT ATT TAT AAA TTC CAT GCT GAA CAA CTG GGT GAT TTT ACC<br>Gly Gly Asp Ile Tyr Lys Phe His Ala Glu Gln Leu Gly Asp Phe Thr<br>        35                      40                      45 | 144 | |
| TTA GGG ATT ATG GGA GGA TAC GCG AAT GCA AAA GGT AAA ACG ATA AAT<br>Leu Gly Ile Met Gly Gly Tyr Ala Asn Ala Lys Gly Lys Thr Ile Asn<br> 50                      55                      60 | 192 | |
| TAC ACG AGC AAC AAA GCT GCC AGA AAC ACA CTG GAT GGT TAT TCT GTC<br>Tyr Thr Ser Asn Lys Ala Ala Arg Asn Thr Leu Asp Gly Tyr Ser Val<br>65                      70                      75                      80 | 240 | |
| GGG GTA TAC GGT ACG TGG TAT CAG AAT GGG GAA AAT GCA ACA GGG CTC<br>Gly Val Tyr Gly Thr Trp Tyr Gln Asn Gly Glu Asn Ala Thr Gly Leu<br>                  85                      90                      95 | 288 | |
| TTT GCT GAA ACT TGG ATG CAA TAT AAC TGG TTT AAT GCA TCA GTG AAA<br>Phe Ala Glu Thr Trp Met Gln Tyr Asn Trp Phe Asn Ala Ser Val Lys<br>                100                    105                  110 | 336 | |
| GGT GAC GGA CTG GAA GAA GAA AAA TAT AAT CTG AAT GGT TTA ACC GCT<br>Gly Asp Gly Leu Glu Glu Glu Lys Tyr Asn Leu Asn Gly Leu Thr Ala<br>                115                    120                  125 | 384 | |
| TCT GCA GGT GGG GGA TAT AAC CTG AAT GTG CAC ACA TGG ACA TCA CCT<br>Ser Ala Gly Gly Gly Tyr Asn Leu Asn Val His Thr Trp Thr Ser Pro<br>130                      135                    140 | 432 | |
| GAA GGA ATA ACA GGT GAA TTC TGG TTA CAG CCT CAT TTG CAG GCT GTC<br>Glu Gly Ile Thr Gly Glu Phe Trp Leu Gln Pro His Leu Gln Ala Val<br>145                      150                    155                  160 | 480 | |
| TGG ATG GGG GTT ACA CCG GAT ACA CAT CAG GAG GAT AAC GGA ACG GTG<br>Trp Met Gly Val Thr Pro Asp Thr His Gln Glu Asp Asn Gly Thr Val<br>                165                    170                  175 | 528 | |
| GTG CAG GGA GCA GGG AAA AAT AAT ATT CAG ACA AAA GCA GGT ATT CGT<br>Val Gln Gly Ala Gly Lys Asn Asn Ile Gln Thr Lys Ala Gly Ile Arg<br>                  180                    185                  190 | 576 | |
| GCA TCC TGG AAG GTG AAA AGC ACC CTG GAT AAG GAT ACC GGG CGG AGG<br>Ala Ser Trp Lys Val Lys Ser Thr Leu Asp Lys Asp Thr Gly Arg Arg<br>                195                    200                  205 | 624 | |
| TTC CGT CCG TAT ATA GAG GCA AAC TGG ATC CAT AAC ACT CAT GAA TTT<br>Phe Arg Pro Tyr Ile Glu Ala Asn Trp Ile His Asn Thr His Glu Phe<br>210                      215                    220 | 672 | |
| GGT GTT AAA ATG AGT GAT GAC AGC CAG TTG TTG TCA GGT AGC CGA AAT<br>Gly Val Lys Met Ser Asp Asp Ser Gln Leu Leu Ser Gly Ser Arg Asn<br>225                      230                    235                  240 | 720 | |
| CAG GGA GAG ATA AAG ACA GGT ATT GAA GGG GTG ATT ACT CAA AAC TTG<br>Gln Gly Glu Ile Lys Thr Gly Ile Glu Gly Val Ile Thr Gln Asn Leu<br>                  245                    250                  255 | 768 | |
| TCA GTG AAT GGC GGA GTC GCA TAT CAG GCA GGA GGT CAC GGG AGC AAT<br>Ser Val Asn Gly Gly Val Ala Tyr Gln Ala Gly Gly His Gly Ser Asn<br>                260                    265                  270 | 816 | |
| GCC ATC TCC GGA GCA CTG GGG ATA AAA TAC AGC TTC<br>Ala Ile Ser Gly Ala Leu Gly Ile Lys Tyr Ser Phe<br>                275                    280 | 852 | |

(2) INFORMATION FOR SEQ ID NO: 7:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO: 7:

```
Ala Ser Val Trp Met Lys Ile Thr Gly Gly Ile Ser Ser Gly Lys Leu
 1               5                  10                 15

Asn Asp Gly Gln Asn Lys Thr Thr Thr Asn Gln Phe Ile Asn Gln Leu
            20                  25                  30

Gly Gly Asp Ile Tyr Lys Phe His Ala Glu Gln Leu Gly Asp Phe Thr
            35                  40                  45

Leu Gly Ile Met Gly Gly Tyr Ala Asn Ala Lys Gly Lys Thr Ile Asn
    50                  55                  60

Tyr Thr Ser Asn Lys Ala Ala Arg Asn Thr Leu Asp Gly Tyr Ser Val
 65                 70                  75                  80

Gly Val Tyr Gly Thr Trp Tyr Gln Asn Gly Glu Asn Ala Thr Gly Leu
                85                  90                  95

Phe Ala Glu Thr Trp Met Gln Tyr Asn Trp Phe Asn Ala Ser Val Lys
            100                 105                 110

Gly Asp Gly Leu Glu Glu Lys Tyr Asn Leu Asn Gly Leu Thr Ala
            115                 120                 125

Ser Ala Gly Gly Tyr Asn Leu Asn Val His Thr Trp Thr Ser Pro
130                 135                 140

Glu Gly Ile Thr Gly Glu Phe Trp Leu Gln Pro His Leu Gln Ala Val
145                 150                 155                 160

Trp Met Gly Val Thr Pro Asp Thr His Gln Glu Asp Asn Gly Thr Val
                165                 170                 175

Val Gln Gly Ala Gly Lys Asn Asn Ile Gln Thr Lys Ala Gly Ile Arg
            180                 185                 190

Ala Ser Trp Lys Val Lys Ser Thr Leu Asp Lys Asp Thr Gly Arg Arg
            195                 200                 205

Phe Arg Pro Tyr Ile Glu Ala Asn Trp Ile His Asn Thr His Glu Phe
210                 215                 220

Gly Val Lys Met Ser Asp Asp Ser Gln Leu Leu Ser Gly Ser Arg Asn
225                 230                 235                 240

Gln Gly Glu Ile Lys Thr Gly Ile Glu Gly Val Ile Thr Gln Asn Leu
                245                 250                 255

Ser Val Asn Gly Gly Val Ala Tyr Gln Ala Gly His Gly Ser Asn
            260                 265                 270

Ala Ile Ser Gly Ala Leu Gly Ile Lys Tyr Ser Phe
            275                 280
```

(2) INFORMATION FOR SEQ ID NO: 8:

(i) SEQUENCE CHARACTERISTICS:
        (A) LENGTH: 813 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..813

(xi) SEQUENCE DESCRIPTION: SEQ ID NO: 8:

```
CTG CGC CTG CGC GCC GAC GCC GGC GGG CCA TGG GCG CGT ACG TTC AGC     48
Leu Arg Leu Arg Ala Asp Ala Gly Gly Pro Trp Ala Arg Thr Phe Ser
285                 290                 295                 300

GAG CGC CAG CAG ATC AGC AAC CGC CAC GCC CGC GCC TAC GAC CAG ACG     96
Glu Arg Gln Gln Ile Ser Asn Arg His Ala Arg Ala Tyr Asp Gln Thr
                305                 310                 315

GTC AGC GGG CTG GAG ATC GGC CTG GAC CGT GGC TGG AGC GCG TCG GGC    144
Val Ser Gly Leu Glu Ile Gly Leu Asp Arg Gly Trp Ser Ala Ser Gly
```

-continued

```
              320                 325                 330
GGG CGC TGG TAC GCC GGC GGC CTG CTC GGC TAC ACC TAT GCC GAC CGC         192
Gly Arg Trp Tyr Ala Gly Gly Leu Leu Gly Tyr Thr Tyr Ala Asp Arg
        335                 340                 345

ACC TAT CCC GGC GAC GGT GGC GGC AAG GTC AAG GGC CTG CAC GTC GGC         240
Thr Tyr Pro Gly Asp Gly Gly Gly Lys Val Lys Gly Leu His Val Gly
350                 355                 360

GGC TAC GCC GCC TAT GTC GGC GAT GGC GGC TAC TAT CTC GAC ACC GTG         288
Gly Tyr Ala Ala Tyr Val Gly Asp Gly Gly Tyr Tyr Leu Asp Thr Val
365                 370                 375                 380

CTG CGG CTG GGC CGC TAC GAT CAG CAA TAC AAC ATT GCC GGC ACC GAT         336
Leu Arg Leu Gly Arg Tyr Asp Gln Gln Tyr Asn Ile Ala Gly Thr Asp
                385                 390                 395

GGC GGC CGC GTC ACC GCC GAC TAC CGC ACA AGC GGC GCC GCA TGG TCG         384
Gly Gly Arg Val Thr Ala Asp Tyr Arg Thr Ser Gly Ala Ala Trp Ser
        400                 405                 410

CTC GAA GGC GGG CGC CGG TTC GAG CTG CCC AAC GAC TGG TTC GCC GAA         432
Leu Glu Gly Gly Arg Arg Phe Glu Leu Pro Asn Asp Trp Phe Ala Glu
        415                 420                 425

CCG CAG GCC GAG GTC ATG CTG TGG CGC ACG TCA GGC AAG CGC TAT CGC         480
Pro Gln Ala Glu Val Met Leu Trp Arg Thr Ser Gly Lys Arg Tyr Arg
430                 435                 440

GCC AGC AAT GGC CTG CGC GTC AAG GTG GAC GCC AAC ACC GCC ACG CTG         528
Ala Ser Asn Gly Leu Arg Val Lys Val Asp Ala Asn Thr Ala Thr Leu
445                 450                 455                 460

GGC CGC CTG GGC TTG CGC TTC GGC CGC CGC ATC GCC CTG GCC GGC GGC         576
Gly Arg Leu Gly Leu Arg Phe Gly Arg Arg Ile Ala Leu Ala Gly Gly
                465                 470                 475

AAC ATC GTG CAG CCC TAC GCC AGG CTC GGC TGG ACG CAG GAG TTC AAA         624
Asn Ile Val Gln Pro Tyr Ala Arg Leu Gly Trp Thr Gln Glu Phe Lys
        480                 485                 490

AGC ACG GGC GAT GTG CGC ACC AAT GGC ATT GGC CAT GCC GGC GCA GGC         672
Ser Thr Gly Asp Val Arg Thr Asn Gly Ile Gly His Ala Gly Ala Gly
        495                 500                 505

CGC CAC GGC CGC GTG GAA CTG GGC GCG GGC GTC GAC GCC GCG TTG GGC         720
Arg His Gly Arg Val Glu Leu Gly Ala Gly Val Asp Ala Ala Leu Gly
510                 515                 520

AAG GGG CAC AAC CTC TAT GCT TCG TAC GAG TAC GCG GCG GGC GAC CGG         768
Lys Gly His Asn Leu Tyr Ala Ser Tyr Glu Tyr Ala Ala Gly Asp Arg
525                 530                 535                 540

ATC AAC ATT CCG TGG TCG TTC CAC GCC GGC TAC CGC TAC AGC TTC             813
Ile Asn Ile Pro Trp Ser Phe His Ala Gly Tyr Arg Tyr Ser Phe
                545                 550                 555
```

(2) INFORMATION FOR SEQ ID NO: 9:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO: 9:

```
Leu Arg Leu Arg Ala Asp Ala Gly Gly Pro Trp Ala Arg Thr Phe Ser
1               5                   10                  15

Glu Arg Gln Gln Ile Ser Asn Arg His Ala Arg Ala Tyr Asp Gln Thr
                20                  25                  30

Val Ser Gly Leu Glu Ile Gly Leu Asp Arg Gly Trp Ser Ala Ser Gly
        35                  40                  45
```

```
Gly Arg Trp Tyr Ala Gly Gly Leu Leu Gly Tyr Thr Tyr Ala Asp Arg
     50                  55                  60

Thr Tyr Pro Gly Asp Gly Gly Lys Val Lys Gly Leu His Val Gly
 65              70                  75                  80

Gly Tyr Ala Ala Tyr Val Gly Asp Gly Gly Tyr Tyr Leu Asp Thr Val
                 85                  90                  95

Leu Arg Leu Gly Arg Tyr Asp Gln Gln Tyr Asn Ile Ala Gly Thr Asp
             100                 105                 110

Gly Gly Arg Val Thr Ala Asp Tyr Arg Thr Ser Gly Ala Ala Trp Ser
             115                 120                 125

Leu Glu Gly Gly Arg Arg Phe Glu Leu Pro Asn Asp Trp Phe Ala Glu
130                 135                 140

Pro Gln Ala Glu Val Met Leu Trp Arg Thr Ser Gly Lys Arg Tyr Arg
145                 150                 155                 160

Ala Ser Asn Gly Leu Arg Val Lys Val Asp Ala Asn Thr Ala Thr Leu
                 165                 170                 175

Gly Arg Leu Gly Leu Arg Phe Gly Arg Arg Ile Ala Leu Ala Gly Gly
             180                 185                 190

Asn Ile Val Gln Pro Tyr Ala Arg Leu Gly Trp Thr Gln Glu Phe Lys
             195                 200                 205

Ser Thr Gly Asp Val Arg Thr Asn Gly Ile Gly His Ala Gly Ala Gly
210                 215                 220

Arg His Gly Arg Val Glu Leu Gly Ala Gly Val Asp Ala Ala Leu Gly
225                 230                 235                 240

Lys Gly His Asn Leu Tyr Ala Ser Tyr Glu Tyr Ala Ala Gly Asp Arg
                 245                 250                 255

Ile Asn Ile Pro Trp Ser Phe His Ala Gly Tyr Arg Tyr Ser Phe
             260                 265                 270
```

(2) INFORMATION FOR SEQ ID NO: 10:

(i) SEQUENCE CHARACTERISTICS:
        (A) LENGTH: 969 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..969

(xi) SEQUENCE DESCRIPTION: SEQ ID NO: 10:

```
CAA AGC CTG TTC GCA TTA GAA GCC GCA CTT GAG GTT ATT GAT GCC CCA        48
Gln Ser Leu Phe Ala Leu Glu Ala Ala Leu Glu Val Ile Asp Ala Pro
         275                 280                 285

CAG CAA TCG GAA AAA GAT CGT CTA GCT CAA GAA GAA GCG GAA AAA CAA        96
Gln Gln Ser Glu Lys Asp Arg Leu Ala Gln Glu Glu Ala Glu Lys Gln
         290                 295                 300

CGC AAA CAA AAA GAC TTG ATC AGC CGT TAT TCA AAT AGT GCG TTA TCA       144
Arg Lys Gln Lys Asp Leu Ile Ser Arg Tyr Ser Asn Ser Ala Leu Ser
305                 310                 315

GAA TTA TCT GCA ACA GTA AAT AGT ATG CTT TCT GTT CAA GAT GAA TTA       192
Glu Leu Ser Ala Thr Val Asn Ser Met Leu Ser Val Gln Asp Glu Leu
320                 325                 330                 335

GAT CGT CTT TTT GTA GAT CAA GCA CAA TCT GCC GTG TGG ACA AAT ATC       240
Asp Arg Leu Phe Val Asp Gln Ala Gln Ser Ala Val Trp Thr Asn Ile
                 340                 345                 350

GCA CAG GAT AAA AGA CGC TAT GAT TCT GAT GCG TTC CGT GCT TAT CAG       288
Ala Gln Asp Lys Arg Arg Tyr Asp Ser Asp Ala Phe Arg Ala Tyr Gln
```

```
CAG CAG AAA ACG AAC TTA CGT CAA ATT GGG GTG CAA AAA GCC TTA GCT      336
Gln Gln Lys Thr Asn Leu Arg Gln Ile Gly Val Gln Lys Ala Leu Ala
        370                 375                 380

AAT GGA CGA ATT GGG GCA GTT TTC TCG CAT AGC CGT TCA GAT AAT ACC      384
Asn Gly Arg Ile Gly Ala Val Phe Ser His Ser Arg Ser Asp Asn Thr
        385                 390                 395

TTT GAT GAA CAG GTT AAA AAT CAC GCG ACA TTA ACG ATG ATG TCG GGT      432
Phe Asp Glu Gln Val Lys Asn His Ala Thr Leu Thr Met Met Ser Gly
400                 405                 410                 415

TTT GCC CAA TAT CAA TGG GGC GAT TTA CAA TTT GGT GTA AAC GTG GGA      480
Phe Ala Gln Tyr Gln Trp Gly Asp Leu Gln Phe Gly Val Asn Val Gly
                420                 425                 430

ACG GGA ATC AGT GCG AGT AAA ATG GCT GAA GAA CAA AGC CGA AAA ATT      528
Thr Gly Ile Ser Ala Ser Lys Met Ala Glu Glu Gln Ser Arg Lys Ile
                435                 440                 445

CAT CGA AAA GCG ATA AAT TAT GGC GTG AAT GCA AGT TAT CAG TTC CGT      576
His Arg Lys Ala Ile Asn Tyr Gly Val Asn Ala Ser Tyr Gln Phe Arg
                450                 455                 460

TTA GGG CAA TTG GGC ATT CAG CCT TAT TTT GGA GTT AAT CGC TAT TTT      624
Leu Gly Gln Leu Gly Ile Gln Pro Tyr Phe Gly Val Asn Arg Tyr Phe
465                 470                 475

ATT GAA CGT GAA AAT TAT CAA TCT GAG GAA GTG AGA GTG AAA ACG CCT      672
Ile Glu Arg Glu Asn Tyr Gln Ser Glu Glu Val Arg Val Lys Thr Pro
480                 485                 490                 495

AGC CTT GCA TTT AAT CGC TAT AAT GCT GGC ATT CGA GTT GAT TAT ACA      720
Ser Leu Ala Phe Asn Arg Tyr Asn Ala Gly Ile Arg Val Asp Tyr Thr
                500                 505                 510

TTT ACT CCG ACA GAT AAT ATC AGC GTT AAG CCT TAT TTC TTC GTC AAT      768
Phe Thr Pro Thr Asp Asn Ile Ser Val Lys Pro Tyr Phe Phe Val Asn
                515                 520                 525

TAT GTT GAT GTT TCA AAC GCT AAC GTA CAA ACC ACG GTA AAT CTC ACG      816
Tyr Val Asp Val Ser Asn Ala Asn Val Gln Thr Thr Val Asn Leu Thr
                530                 535                 540

GTG TTG CAA CAA CCA TTT GGA CGT TAT TGG CAA AAA GAA GTG GGA TTA      864
Val Leu Gln Gln Pro Phe Gly Arg Tyr Trp Gln Lys Glu Val Gly Leu
545                 550                 555

AAG GCA GAA ATT TTA CAT TTC CAA ATT TCC GCT TTT ATC TCA AAA TCT      912
Lys Ala Glu Ile Leu His Phe Gln Ile Ser Ala Phe Ile Ser Lys Ser
560                 565                 570                 575

CAA GGT TCA CAA CTC GGC AAA CAG CAA AAT GTG GGC GTG AAA TTG GGC      960
Gln Gly Ser Gln Leu Gly Lys Gln Gln Asn Val Gly Val Lys Leu Gly
                580                 585                 590

TAT CGT TGG                                                          969
Tyr Arg Trp (2) INFORMATION FOR SEQ ID NO: 11:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO: 11:

Gln Ser Leu Phe Ala Leu Glu Ala Ala Leu Glu Val Ile Asp Ala Pro
 1               5                  10                  15

Gln Gln Ser Glu Lys Asp Arg Leu Ala Gln Glu Glu Ala Glu Lys Gln
                20                  25                  30
```

```
Arg Lys Gln Lys Asp Leu Ile Ser Arg Tyr Ser Asn Ser Ala Leu Ser
             35                  40                  45

Glu Leu Ser Ala Thr Val Asn Ser Met Leu Ser Val Gln Asp Glu Leu
         50                  55                  60

Asp Arg Leu Phe Val Asp Gln Ala Gln Ser Ala Val Trp Thr Asn Ile
 65                  70                  75                  80

Ala Gln Asp Lys Arg Arg Tyr Asp Ser Asp Ala Phe Arg Ala Tyr Gln
                 85                  90                  95

Gln Gln Lys Thr Asn Leu Arg Gln Ile Gly Val Gln Lys Ala Leu Ala
            100                 105                 110

Asn Gly Arg Ile Gly Ala Val Phe Ser His Ser Arg Ser Asp Asn Thr
        115                 120                 125

Phe Asp Glu Gln Val Lys Asn His Ala Thr Leu Thr Met Met Ser Gly
130                 135                 140

Phe Ala Gln Tyr Gln Trp Gly Asp Leu Gln Phe Gly Val Asn Val Gly
145                 150                 155                 160

Thr Gly Ile Ser Ala Ser Lys Met Ala Glu Glu Ser Arg Lys Ile
                165                 170                 175

His Arg Lys Ala Ile Asn Tyr Gly Val Asn Ala Ser Tyr Gln Phe Arg
            180                 185                 190

Leu Gly Gln Leu Gly Ile Gln Pro Tyr Phe Gly Val Asn Arg Tyr Phe
        195                 200                 205

Ile Glu Arg Glu Asn Tyr Gln Ser Glu Glu Val Arg Val Lys Thr Pro
    210                 215                 220

Ser Leu Ala Phe Asn Arg Tyr Asn Ala Gly Ile Arg Val Asp Tyr Thr
225                 230                 235                 240

Phe Thr Pro Thr Asp Asn Ile Ser Val Lys Pro Tyr Phe Phe Val Asn
                245                 250                 255

Tyr Val Asp Val Ser Asn Ala Asn Val Gln Thr Thr Val Asn Leu Thr
            260                 265                 270

Val Leu Gln Gln Pro Phe Gly Arg Tyr Trp Gln Lys Glu Val Gly Leu
        275                 280                 285

Lys Ala Glu Ile Leu His Phe Gln Ile Ser Ala Phe Ile Ser Lys Ser
    290                 295                 300

Gln Gly Ser Gln Leu Gly Lys Gln Gln Asn Val Gly Val Lys Leu Gly
305                 310                 315                 320

Tyr Arg Trp (2) INFORMATION FOR SEQ ID NO: 12:

(i) SEQUENCE CHARACTERISTICS:
        (A) LENGTH: 918 base pairs
        (B) TYPE: nucleic acid
        (C) STRANDEDNESS: both
        (D) TOPOLOGY: linear (ix) FEATURE:
         (A) NAME/KEY: CDS
         (B) LOCATION:1..918

(xi) SEQUENCE DESCRIPTION: SEQ ID NO: 12:

ACC TCA ATC TAC ACC ACA GTA CAG GCA GGA TGG GAT CAT GTA TTT GGC      48
Thr Ser Ile Tyr Thr Thr Val Gln Ala Gly Trp Asp His Val Phe Gly
325                 330                 335

AGC GAG GGT GGA AAT GAC TTT TTA GGT TTT GCT GTG GCT TAT GCA GGT     96
Ser Glu Gly Gly Asn Asp Phe Leu Gly Phe Ala Val Ala Tyr Ala Gly
340                 345                 350                 355
```

```
GCA GCG ATG AGC TCT GAG AAG AAA GAA CAG CTA GTA AAT GGT GCA CAA         144
Ala Ala Met Ser Ser Glu Lys Lys Glu Gln Leu Val Asn Gly Ala Gln
            360                 365                 370

AAG GGA GTA AAA TCC AGC GGT GGA AAT GCC TTT GAA ATC TCG CTC TAC         192
Lys Gly Val Lys Ser Ser Gly Gly Asn Ala Phe Glu Ile Ser Leu Tyr
                375                 380                 385

AAC TCC TAT GTA CAA GAT GGT GCT GCT TCT AGC ACA GAT TTC AAG TAT         240
Asn Ser Tyr Val Gln Asp Gly Ala Ala Ser Ser Thr Asp Phe Lys Tyr
                390                 395                 400

GGT TTT TAT AGT GAT AGC GTG GCA AAA TTC AGC TTC TTG TGG AAC AAG         288
Gly Phe Tyr Ser Asp Ser Val Ala Lys Phe Ser Phe Leu Trp Asn Lys
            405                 410                 415

CTT ACA ATG TTT GGT GAG GAC AGC TCT CCT AAC ATG CAA AAC TTT GGT         336
Leu Thr Met Phe Gly Glu Asp Ser Ser Pro Asn Met Gln Asn Phe Gly
420                 425                 430                 435

TTC ACC TTC TCT CAA GAG ATT GGT TAT CGC TTC TTG CTA GGA AAT CAC         384
Phe Thr Phe Ser Gln Glu Ile Gly Tyr Arg Phe Leu Leu Gly Asn His
                440                 445                 450

AAC GAG TGG TAT ATC ACT CCA CAA GGG CAA GTT GCT TTA GGT TAT TTC         432
Asn Glu Trp Tyr Ile Thr Pro Gln Gly Gln Val Ala Leu Gly Tyr Phe
                455                 460                 465

AAC CAA AGC AAT ATC AAG CAA ACC CTA GGA AGC CAC TGG CTA AAA GGC         480
Asn Gln Ser Asn Ile Lys Gln Thr Leu Gly Ser His Trp Leu Lys Gly
            470                 475                 480

GAG CAA AGT TCT ATC TTC ACA GTG CAG GGG CGA ATT GGA AGC AAC TTT         528
Glu Gln Ser Ser Ile Phe Thr Val Gln Gly Arg Ile Gly Ser Asn Phe
            485                 490                 495

GGT TAT AGA TTT AAT CAA TTC ACT GAA GAC AAG GGC TGG GCT TCA GAG         576
Gly Tyr Arg Phe Asn Gln Phe Thr Glu Asp Lys Gly Trp Ala Ser Glu
500                 505                 510                 515

CTT TAT TTG GGC TTG TGG TAC ATC GGC GAT TAT ATC AGT GGT GGC AAT         624
Leu Tyr Leu Gly Leu Trp Tyr Ile Gly Asp Tyr Ile Ser Gly Gly Asn
                520                 525                 530

CTT ACC CTC GTG TCT GAC CTA GGT TCT GTA AAC ACT TTA AGG ACT TTG         672
Leu Thr Leu Val Ser Asp Leu Gly Ser Val Asn Thr Leu Arg Thr Leu
            535                 540                 545

AGC TCT ACT GGT AGA TTT GCC TTT AAC ATT GGT ACA AAC TTC GTC GTC         720
Ser Ser Thr Gly Arg Phe Ala Phe Asn Ile Gly Thr Asn Phe Val Val
            550                 555                 560

AAA GAT AAT CAT AGA TTC TAC TTT GAT TTT GAA AGA AGC TTT GGA GGC         768
Lys Asp Asn His Arg Phe Tyr Phe Asp Phe Glu Arg Ser Phe Gly Gly
            565                 570                 575

AAA ATC ATC ACA GAT TAC CAA TTC AAC ATT GGC TAT CGC TAT AAC TTT         816
Lys Ile Ile Thr Asp Tyr Gln Phe Asn Ile Gly Tyr Arg Tyr Asn Phe
580                 585                 590                 595

GGC GAA AAC AGA AAA TAC GTT TCT CTT CTT GCA GGT AGT ATG AAA GAC         864
Gly Glu Asn Arg Lys Tyr Val Ser Leu Leu Ala Gly Ser Met Lys Asp
                600                 605                 610

ACT ATC AAA AAA GAT GAT AAG AAA GAA AAC AAA GAA GAG ACA GAA GAA         912
Thr Ile Lys Lys Asp Asp Lys Lys Glu Asn Lys Glu Glu Thr Glu Glu
            615                 620                 625

ATT GAG                                                                 918
Ile Glu
```

(2) INFORMATION FOR SEQ ID NO: 13:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO: 13:

```
Thr Ser Ile Tyr Thr Thr Val Gln Ala Gly Trp Asp His Val Phe Gly
  1               5                  10                  15

Ser Glu Gly Gly Asn Asp Phe Leu Gly Phe Ala Val Ala Tyr Ala Gly
                 20                  25                  30

Ala Ala Met Ser Ser Glu Lys Lys Glu Gln Leu Val Asn Gly Ala Gln
             35                  40                  45

Lys Gly Val Lys Ser Ser Gly Gly Asn Ala Phe Glu Ile Ser Leu Tyr
 50                  55                  60

Asn Ser Tyr Val Gln Asp Gly Ala Ala Ser Ser Thr Asp Phe Lys Tyr
 65                  70                  75                  80

Gly Phe Tyr Ser Asp Ser Val Ala Lys Phe Ser Phe Leu Trp Asn Lys
                 85                  90                  95

Leu Thr Met Phe Gly Glu Asp Ser Ser Pro Asn Met Gln Asn Phe Gly
                100                 105                 110

Phe Thr Phe Ser Gln Glu Ile Gly Tyr Arg Phe Leu Leu Gly Asn His
            115                 120                 125

Asn Glu Trp Tyr Ile Thr Pro Gln Gly Gln Val Ala Leu Gly Tyr Phe
130                 135                 140

Asn Gln Ser Asn Ile Lys Gln Thr Leu Gly Ser His Trp Leu Lys Gly
145                 150                 155                 160

Glu Gln Ser Ser Ile Phe Thr Val Gln Gly Arg Ile Gly Ser Asn Phe
                165                 170                 175

Gly Tyr Arg Phe Asn Gln Phe Thr Glu Asp Lys Gly Trp Ala Ser Glu
            180                 185                 190

Leu Tyr Leu Gly Leu Trp Tyr Ile Gly Asp Tyr Ile Ser Gly Gly Asn
            195                 200                 205

Leu Thr Leu Val Ser Asp Leu Gly Ser Val Asn Thr Leu Arg Thr Leu
210                 215                 220

Ser Ser Thr Gly Arg Phe Ala Phe Asn Ile Gly Thr Asn Phe Val Val
225                 230                 235                 240

Lys Asp Asn His Arg Phe Tyr Phe Asp Phe Glu Arg Ser Phe Gly Gly
                245                 250                 255

Lys Ile Ile Thr Asp Tyr Gln Phe Asn Ile Gly Tyr Arg Tyr Asn Phe
            260                 265                 270

Gly Glu Asn Arg Lys Tyr Val Ser Leu Leu Ala Gly Ser Met Lys Asp
            275                 280                 285

Thr Ile Lys Lys Asp Asp Lys Lys Glu Asn Lys Glu Glu Thr Glu Glu
290                 295                 300

Ile Glu
305
```

(2) INFORMATION FOR SEQ ID NO: 14:

(i) SEQUENCE CHARACTERISTICS:
        (A) LENGTH: 855 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..855

(xi) SEQUENCE DESCRIPTION: SEQ ID NO: 14:

```
GAA ACC ACC ATG TGG ATT CGT ACT GTT GGT GGA CAT AAT GAG CAT AAT        48
Glu Thr Thr Met Trp Ile Arg Thr Val Gly Gly His Asn Glu His Asn
            310                 315                 320

TTA GCT GAT AGA CAA TTA AAA ACC ACA GCT AAC AGG ATG GTT TAT CAG        96
Leu Ala Asp Arg Gln Leu Lys Thr Thr Ala Asn Arg Met Val Tyr Gln
        325                 330                 335

ATT GGT GGA GAT ATT TTG AAG ACA AAC TTC ACT GAT CAT GAT GGC TTG       144
Ile Gly Gly Asp Ile Leu Lys Thr Asn Phe Thr Asp His Asp Gly Leu
    340                 345                 350

CAT GTG GGT ATT ATG GGA GCT TAT GGA TAT CAG GAT AGC AAA ACT CAT       192
His Val Gly Ile Met Gly Ala Tyr Gly Tyr Gln Asp Ser Lys Thr His
355                 360                 365                 370

AAT AAG TAT ACT AGT TAT AGT TCA CGA GGA ACT GTG AGC GGT TAT ACT       240
Asn Lys Tyr Thr Ser Tyr Ser Ser Arg Gly Thr Val Ser Gly Tyr Thr
                375                 380                 385

GCC GGT TTG TAC AGT TCT TGG TTT CAG GAT GAA AAA GAA CGA ACA GGT       288
Ala Gly Leu Tyr Ser Ser Trp Phe Gln Asp Glu Lys Glu Arg Thr Gly
            390                 395                 400

CTA TAT ATG GAT GCT TGG TTG CAG TAC AGT TGG TTT AAT AAT ACA GTC       336
Leu Tyr Met Asp Ala Trp Leu Gln Tyr Ser Trp Phe Asn Asn Thr Val
        405                 410                 415

AAA GGA GAT GGG TTA ACT GGT GAG AAA TAT TCC AGC AAA GGA ATA ACA       384
Lys Gly Asp Gly Leu Thr Gly Glu Lys Tyr Ser Ser Lys Gly Ile Thr
    420                 425                 430

GGA GCT TTG GAA GCT GGC TAT ATC TAC CCA ACC ATA CGC TGG ACT GCT       432
Gly Ala Leu Glu Ala Gly Tyr Ile Tyr Pro Thr Ile Arg Trp Thr Ala
435                 440                 445                 450

CAT AAT AAT ATT GAC AAC GCA TTG TAT CTC AAT CCA CAA GTC CAG ATA       480
His Asn Asn Ile Asp Asn Ala Leu Tyr Leu Asn Pro Gln Val Gln Ile
                455                 460                 465

ACT AGG CAT GGG GTA AAA GCA AAC GAC TAT ATT GAA CAC AAT GGC ACT       528
Thr Arg His Gly Val Lys Ala Asn Asp Tyr Ile Glu His Asn Gly Thr
            470                 475                 480

ATG GTC ACA TCC TCT GGG GGC AAT AAT ATT CAA GCA AAA TTG GGA TTG       576
Met Val Thr Ser Ser Gly Gly Asn Asn Ile Gln Ala Lys Leu Gly Leu
        485                 490                 495

CGT ACA TCC TTA ATT AGT CAG AGT TGT ATC GAT AAG GAG ACT CTT CGT       624
Arg Thr Ser Leu Ile Ser Gln Ser Cys Ile Asp Lys Glu Thr Leu Arg
    500                 505                 510

AAG TTC GAA CCA TTT TTG GAA GTG AAT TGG AAA TGG AGC TCA AAG CAA       672
Lys Phe Glu Pro Phe Leu Glu Val Asn Trp Lys Trp Ser Ser Lys Gln
515                 520                 525                 530

TAT GGT GTA ATT ATG AAT GGC ATG TCA AAT CAC CAG ATA GGC AAC CGT       720
Tyr Gly Val Ile Met Asn Gly Met Ser Asn His Gln Ile Gly Asn Arg
                535                 540                 545

AAT GTG ATT GAA CTC AAA ACT GGT GTG GGG GGG CGT CTT GCA GAT AAC       768
Asn Val Ile Glu Leu Lys Thr Gly Val Gly Gly Arg Leu Ala Asp Asn
            550                 555                 560

CTA AGC ATC TGG GGA AAC GTA TCT CAG CAA TTG GGT AAT AAC AGT TAC       816
Leu Ser Ile Trp Gly Asn Val Ser Gln Gln Leu Gly Asn Asn Ser Tyr
        565                 570                 575

AGA GAC ACC CAA GGT ATT TTG GGT GTG AAA TAT ACC TTC                   855
Arg Asp Thr Gln Gly Ile Leu Gly Val Lys Tyr Thr Phe
    580                 585                 590

(2) INFORMATION FOR SEQ ID NO: 15:

(i) SEQUENCE CHARACTERISTICS:
        (A) LENGTH: 285 amino acids
        (B) TYPE: amino acid
        (D) TOPOLOGY: linear
```

(ii) MOLECULE TYPE: protein (xi) SEQUENCE DESCRIPTION: SEQ ID NO: 15:

```
Glu Thr Thr Met Trp Ile Arg Thr Val Gly Gly His Asn Glu His Asn
 1               5                  10                  15

Leu Ala Asp Arg Gln Leu Lys Thr Thr Ala Asn Arg Met Val Tyr Gln
            20                  25                  30

Ile Gly Gly Asp Ile Leu Lys Thr Asn Phe Thr Asp His Asp Gly Leu
        35                  40                  45

His Val Gly Ile Met Gly Ala Tyr Gly Tyr Gln Asp Ser Lys Thr His
    50                  55                  60

Asn Lys Tyr Thr Ser Tyr Ser Ser Arg Gly Thr Val Ser Gly Tyr Thr
 65                 70                  75                  80

Ala Gly Leu Tyr Ser Ser Trp Phe Gln Asp Glu Lys Glu Arg Thr Gly
                85                  90                  95

Leu Tyr Met Asp Ala Trp Leu Gln Tyr Ser Trp Phe Asn Asn Thr Val
            100                 105                 110

Lys Gly Asp Gly Leu Thr Gly Glu Lys Tyr Ser Ser Lys Gly Ile Thr
        115                 120                 125

Gly Ala Leu Glu Ala Gly Tyr Ile Tyr Pro Thr Ile Arg Trp Thr Ala
130                 135                 140

His Asn Asn Ile Asp Asn Ala Leu Tyr Leu Asn Pro Gln Val Gln Ile
145                 150                 155                 160

Thr Arg His Gly Val Lys Ala Asn Asp Tyr Ile Glu His Asn Gly Thr
                165                 170                 175

Met Val Thr Ser Ser Gly Gly Asn Asn Ile Gln Ala Lys Leu Gly Leu
            180                 185                 190

Arg Thr Ser Leu Ile Ser Gln Ser Cys Ile Asp Lys Glu Thr Leu Arg
        195                 200                 205

Lys Phe Glu Pro Phe Leu Glu Val Asn Trp Lys Trp Ser Ser Lys Gln
    210                 215                 220

Tyr Gly Val Ile Met Asn Gly Met Ser Asn His Gln Ile Gly Asn Arg
225                 230                 235                 240

Asn Val Ile Glu Leu Lys Thr Gly Val Gly Gly Arg Leu Ala Asp Asn
                245                 250                 255

Leu Ser Ile Trp Gly Asn Val Ser Gln Gln Leu Gly Asn Asn Ser Tyr
            260                 265                 270

Arg Asp Thr Gln Gly Ile Leu Gly Val Lys Tyr Thr Phe
        275                 280                 285
```

(2) INFORMATION FOR SEQ ID NO: 16:

(i) SEQUENCE CHARACTERISTICS:
        (A) LENGTH: 822 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..822

(xi) SEQUENCE DESCRIPTION: SEQ ID NO: 16:

```
CTG GGC GAG TTG CGC CTG AAT CCG GAC GCC GGC GGC GCC TGG GGC CGC      48
Leu Gly Glu Leu Arg Leu Asn Pro Asp Ala Gly Gly Ala Trp Gly Arg
                290                 295                 300

GGC TTC GCG CAA CGC CAG CAG CTG GAC AAC CGC GCC GGG CGG CGC TTC      96
```

-continued

```
Gly Phe Ala Gln Arg Gln Gln Leu Asp Asn Arg Ala Gly Arg Arg Phe
            305                 310                 315

GAC CAG AAG GTG GCC GGC TTC GAG CTG GGC GCC GAC CAC GCG GTG GCG    144
Asp Gln Lys Val Ala Gly Phe Glu Leu Gly Ala Asp His Ala Val Ala
            320                 325                 330

GTG GCC GGC GGA CGC TGG CAC CTG GGC GGG CTG GCC GGC TAT ACG CGC    192
Val Ala Gly Gly Arg Trp His Leu Gly Gly Leu Ala Gly Tyr Thr Arg
            335                 340                 345

GGC GAC CGC GGC TTC ACC GGC GAC GGC GGC CAC ACC GAC AGC GTG        240
Gly Asp Arg Gly Phe Thr Gly Asp Gly Gly His Thr Asp Ser Val
350                 355                 360                 365

CAT GTC GGG GGC TAT GCC ACA TAT ATC GCC GAC AGC GGT TTC TAC CTG    288
His Val Gly Gly Tyr Ala Thr Tyr Ile Ala Asp Ser Gly Phe Tyr Leu
                370                 375                 380

GAC GCG ACG CTG CGC GCC AGC CGC CTG GAG AAT GAC TTC AAG GTG GCG    336
Asp Ala Thr Leu Arg Ala Ser Arg Leu Glu Asn Asp Phe Lys Val Ala
            385                 390                 395

GGC AGC GAC GGG TAC GCG GTC AAG GGC AAG TAC CGC ACC CAT GGG GTG    384
Gly Ser Asp Gly Tyr Ala Val Lys Gly Lys Tyr Arg Thr His Gly Val
            400                 405                 410

GGC GCC TCG CTC GAG GCG GGC CGG CGC TTT ACC CAT GCC GAC GGC TGG    432
Gly Ala Ser Leu Glu Ala Gly Arg Arg Phe Thr His Ala Asp Gly Trp
            415                 420                 425

TTC CTC GAG CCG CAG GCC GAG CTG GCG GTA TTC CGG GCC GGC GGC GGT    480
Phe Leu Glu Pro Gln Ala Glu Leu Ala Val Phe Arg Ala Gly Gly Gly
430                 435                 440                 445

GCG TAC CGC GCG GCC AAC GGC CTG CGG GTG CGC GAC GAA GGC GGC AGC    528
Ala Tyr Arg Ala Ala Asn Gly Leu Arg Val Arg Asp Glu Gly Gly Ser
                450                 455                 460

TCG GTG CTG GGT CGC CTG GGC CTG GAG GTC GGC AAG CGC ATC GAA CTG    576
Ser Val Leu Gly Arg Leu Gly Leu Glu Val Gly Lys Arg Ile Glu Leu
            465                 470                 475

GCA GGC GGC AGG CAG GTG CAG CCA TAC ATC AAG GCC AGC GTG CTG CAG    624
Ala Gly Gly Arg Gln Val Gln Pro Tyr Ile Lys Ala Ser Val Leu Gln
            480                 485                 490

GAG TTC GAC GGC GCG GGT ACG GTA CAC ACC AAC GGC ATC GCG CAC CGC    672
Glu Phe Asp Gly Ala Gly Thr Val His Thr Asn Gly Ile Ala His Arg
495                 500                 505

ACC GAA CTG CGC GGC ACG CGC GCC GAA CTG GGC CTG GGC ATG GCC GCC    720
Thr Glu Leu Arg Gly Thr Arg Ala Glu Leu Gly Leu Gly Met Ala Ala
510                 515                 520                 525

GCG CTG GGC CGC GGC CAC AGC CTG TAT GCC TCG TAC GAG TAC TCC AAG    768
Ala Leu Gly Arg Gly His Ser Leu Tyr Ala Ser Tyr Glu Tyr Ser Lys
                530                 535                 540

GGC CCG AAG CTG GCC ATG CCG TGG ACC TTC CAC GCG GGC TAC CGG TAC    816
Gly Pro Lys Leu Ala Met Pro Trp Thr Phe His Ala Gly Tyr Arg Tyr
            545                 550                 555

AGC TGG                                                            822
Ser Trp
```

(2) INFORMATION FOR SEQ ID NO: 17:

(i) SEQUENCE CHARACTERISTICS:
       (A) LENGTH: 274 amino acids
       (B) TYPE: amino acid
       (D) TOPOLOGY: linear (ii) MOLECULE TYPE: protein (xi) SEQUENCE DESCRIPTION: SEQ ID NO: 17:

Leu Gly Glu Leu Arg Leu Asn Pro Asp Ala Gly Gly Ala Trp Gly Arg

-continued

```
  1               5                10               15
Gly Phe Ala Gln Arg Gln Gln Leu Asp Asn Arg Ala Gly Arg Arg Phe
             20                  25                  30

Asp Gln Lys Val Ala Gly Phe Glu Leu Gly Ala Asp His Ala Val Ala
             35                  40                  45

Val Ala Gly Gly Arg Trp His Leu Gly Gly Leu Ala Gly Tyr Thr Arg
             50                  55                  60

Gly Asp Arg Gly Phe Thr Gly Asp Gly Gly His Thr Asp Ser Val
 65              70                  75                  80

His Val Gly Gly Tyr Ala Thr Tyr Ile Ala Asp Ser Gly Phe Tyr Leu
             85                  90                  95

Asp Ala Thr Leu Arg Ala Ser Arg Leu Glu Asn Asp Phe Lys Val Ala
            100                 105                 110

Gly Ser Asp Gly Tyr Ala Val Lys Gly Lys Tyr Arg Thr His Gly Val
            115                 120                 125

Gly Ala Ser Leu Glu Ala Gly Arg Arg Phe Thr His Ala Asp Gly Trp
            130                 135                 140

Phe Leu Glu Pro Gln Ala Glu Leu Ala Val Phe Arg Ala Gly Gly Gly
145                 150                 155                 160

Ala Tyr Arg Ala Ala Asn Gly Leu Arg Val Arg Asp Glu Gly Gly Ser
            165                 170                 175

Ser Val Leu Gly Arg Leu Gly Leu Glu Val Gly Lys Arg Ile Glu Leu
            180                 185                 190

Ala Gly Gly Arg Gln Val Gln Pro Tyr Ile Lys Ala Ser Val Leu Gln
            195                 200                 205

Glu Phe Asp Gly Ala Gly Thr Val His Thr Asn Gly Ile Ala His Arg
210                 215                 220

Thr Glu Leu Arg Gly Thr Arg Ala Glu Leu Gly Leu Gly Met Ala Ala
225                 230                 235                 240

Ala Leu Gly Arg Gly His Ser Leu Tyr Ala Ser Tyr Glu Tyr Ser Lys
            245                 250                 255

Gly Pro Lys Leu Ala Met Pro Trp Thr Phe His Ala Gly Tyr Arg Tyr
            260                 265                 270

Ser Trp
```

(2) INFORMATION FOR SEQ ID NO: 18:

(i) SEQUENCE CHARACTERISTICS:
        (A) LENGTH: 822 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..822

(xi) SEQUENCE DESCRIPTION: SEQ ID NO: 18:

```
CTG GGC GAG TTG CGC CTG AAT CCG GAC GCC GGC GGC GCT TGG GGC CGC      48
Leu Gly Glu Leu Arg Leu Asn Pro Asp Ala Gly Gly Ala Trp Gly Arg
275                 280                 285                 290

GGC TTC GCG CAA CGC CAG CAA CTG GAC AAC CGC GCC GGG CGG CGC TTC      96
Gly Phe Ala Gln Arg Gln Gln Leu Asp Asn Arg Ala Gly Arg Arg Phe
                295                 300                 305

GAC CAG AAG GTG GCC GGC TTC GAG CTG GGC GCC GAC CAC GCG GTG GCG     144
Asp Gln Lys Val Ala Gly Phe Glu Leu Gly Ala Asp His Ala Val Ala
            310                 315                 320
```

```
GTG GCC GGC GGG CGC TGG CAC CTG GGC GGG CTG GCC GGC TAT ACG CGC      192
Val Ala Gly Gly Arg Trp His Leu Gly Gly Leu Ala Gly Tyr Thr Arg
    325                 330                 335

GGC GAC CGC GGC TTT ACC GGC GAC GGC GGC CAC ACC GAC AGC GTG          240
Gly Asp Arg Gly Phe Thr Gly Asp Gly Gly His Thr Asp Ser Val
340                 345                 350

CAT GTC GGG GGC TAT GCC ACC TAT ATC GCC AAC AGC GGT TTC TAC CTG      288
His Val Gly Gly Tyr Ala Thr Tyr Ile Ala Asn Ser Gly Phe Tyr Leu
355                 360                 365                 370

GAC GCG ACG CTG CGC GCC AGC CGC CTC GAA AAT GAC TTC AAG GTG GCG      336
Asp Ala Thr Leu Arg Ala Ser Arg Leu Glu Asn Asp Phe Lys Val Ala
                375                 380                 385

GGC AGC GAT GGG TAC GCG GTC AAG GGC AAG TAC CGC ACC CAT GGG GTA      384
Gly Ser Asp Gly Tyr Ala Val Lys Gly Lys Tyr Arg Thr His Gly Val
            390                 395                 400

GGC GTC TCG CTC GAG GCG GGC CGG CGC TTC GCC CAT GCC GAC GGC TGG      432
Gly Val Ser Leu Glu Ala Gly Arg Arg Phe Ala His Ala Asp Gly Trp
            405                 410                 415

TTC CTC GAG CCG CAG GCC GAG CTG GCG GTG TTC CGG GTC GGC GGC GGT      480
Phe Leu Glu Pro Gln Ala Glu Leu Ala Val Phe Arg Val Gly Gly Gly
420                 425                 430

GCG TAC CGC GCG GCC AAT GGC CTG CGG GTG CGC GAC GAA GGC GGC AGC      528
Ala Tyr Arg Ala Ala Asn Gly Leu Arg Val Arg Asp Glu Gly Gly Ser
435                 440                 445                 450

TCG GTG CTG GGT CGC CTG GGC CTG GAG GTC GGC AAG CGC ATC GAA CTG      576
Ser Val Leu Gly Arg Leu Gly Leu Glu Val Gly Lys Arg Ile Glu Leu
                455                 460                 465

GCA GGC GGC AGG CAG GTG CAG CCA TAC ATC AAG GCC AGC GTG TTG CAG      624
Ala Gly Gly Arg Gln Val Gln Pro Tyr Ile Lys Ala Ser Val Leu Gln
            470                 475                 480

GAG TTC GAC GGC GCG GGT ACG GTA CGC ACC AAC GGC ATC GCG CAT CGC      672
Glu Phe Asp Gly Ala Gly Thr Val Arg Thr Asn Gly Ile Ala His Arg
            485                 490                 495

ACC GAA CTG CGC GGC ACG CGC GCC GAA CTG GGC CTG GGC ATG GCC GCC      720
Thr Glu Leu Arg Gly Thr Arg Ala Glu Leu Gly Leu Gly Met Ala Ala
500                 505                 510

GCG CTG GGC CGC GGC CAC AGC CTG TAT GCC TCG TAC GAG TAC TCC AAG      768
Ala Leu Gly Arg Gly His Ser Leu Tyr Ala Ser Tyr Glu Tyr Ser Lys
515                 520                 525                 530

GGC CCG AAG CTG GCC ATG CCG TGG ACC TTC CAC GCG GGC TAC CGG TAC      816
Gly Pro Lys Leu Ala Met Pro Trp Thr Phe His Ala Gly Tyr Arg Tyr
            535                 540                 545

AGC TGG                                                               822
Ser Trp (2) INFORMATION FOR SEQ ID NO: 19:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO: 19:

Leu Gly Glu Leu Arg Leu Asn Pro Asp Ala Gly Gly Ala Trp Gly Arg
1               5                   10                  15

Gly Phe Ala Gln Arg Gln Gln Leu Asp Asn Arg Ala Gly Arg Arg Phe
            20                  25                  30

Asp Gln Lys Val Ala Gly Phe Glu Leu Gly Ala Asp His Ala Val Ala
        35                  40                  45
```

```
Val Ala Gly Gly Arg Trp His Leu Gly Gly Leu Ala Gly Tyr Thr Arg
 50                  55                  60

Gly Asp Arg Gly Phe Thr Gly Asp Gly Gly His Thr Asp Ser Val
 65                  70                  75                  80

His Val Gly Gly Tyr Ala Thr Tyr Ile Ala Asn Ser Gly Phe Tyr Leu
                 85                  90                  95

Asp Ala Thr Leu Arg Ala Ser Arg Leu Glu Asn Asp Phe Lys Val Ala
                100                 105                 110

Gly Ser Asp Gly Tyr Ala Val Lys Gly Lys Tyr Arg Thr His Gly Val
            115                 120                 125

Gly Val Ser Leu Glu Ala Gly Arg Arg Phe Ala His Ala Asp Gly Trp
            130                 135                 140

Phe Leu Glu Pro Gln Ala Glu Leu Ala Val Phe Arg Val Gly Gly Gly
145                 150                 155                 160

Ala Tyr Arg Ala Ala Asn Gly Leu Arg Val Arg Asp Glu Gly Gly Ser
                165                 170                 175

Ser Val Leu Gly Arg Leu Gly Leu Glu Val Gly Lys Arg Ile Glu Leu
            180                 185                 190

Ala Gly Gly Arg Gln Val Gln Pro Tyr Ile Lys Ala Ser Val Leu Gln
            195                 200                 205

Glu Phe Asp Gly Ala Gly Thr Val Arg Thr Asn Gly Ile Ala His Arg
    210                 215                 220

Thr Glu Leu Arg Gly Thr Arg Ala Glu Leu Gly Leu Gly Met Ala Ala
225                 230                 235                 240

Ala Leu Gly Arg Gly His Ser Leu Tyr Ala Ser Tyr Glu Tyr Ser Lys
                245                 250                 255

Gly Pro Lys Leu Ala Met Pro Trp Thr Phe His Ala Gly Tyr Arg Tyr
            260                 265                 270

Ser Trp (2) INFORMATION FOR SEQ ID NO: 20:

(i) SEQUENCE CHARACTERISTICS:
        (A) LENGTH: 852 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..852

(xi) SEQUENCE DESCRIPTION: SEQ ID NO: 20:

AAG TTT GGT GCG TGG ATA AGC CCG TTT GTC GGT AAT GCA ACG CAG AAG    48
Lys Phe Gly Ala Trp Ile Ser Pro Phe Val Gly Asn Ala Thr Gln Lys
275                 280                 285                 290

ATG TGT AAC AGT ATA AGT GGT TAT AAG TCT GAT ACA ACT GGT GGC ACT    96
Met Cys Asn Ser Ile Ser Gly Tyr Lys Ser Asp Thr Thr Gly Gly Thr
                295                 300                 305

ATA GGT TTT GAC GGC TTC GTT AGC GAT GAT CTA GCA CTC GGA CTT GCA   144
Ile Gly Phe Asp Gly Phe Val Ser Asp Asp Leu Ala Leu Gly Leu Ala
            310                 315                 320

TAT ACA AGA GCC GAT ACT GAC ATT AAG CTA AAA AAT AAT AAA ACG GGC   192
Tyr Thr Arg Ala Asp Thr Asp Ile Lys Leu Lys Asn Asn Lys Thr Gly
            325                 330                 335

GAT AAG AAT AAG GTA GAG AGC AAC ATC TAT TCT TTA TAC GGT TTA TAT   240
Asp Lys Asn Lys Val Glu Ser Asn Ile Tyr Ser Leu Tyr Gly Leu Tyr
340                 345                 350
```

-continued

```
AAT GTA CCT TAT GAA AAT CTC TTC GTT GAA GCT ATA GCA TCT TAC TCA      288
Asn Val Pro Tyr Glu Asn Leu Phe Val Glu Ala Ile Ala Ser Tyr Ser
355             360                 365                 370

GAT AAT AAG ATA AGA AGC AAA TCA AGA CGT GTT ATT GCA ACG ACA CTA      336
Asp Asn Lys Ile Arg Ser Lys Ser Arg Arg Val Ile Ala Thr Thr Leu
            375                 380                 385

GAG ACT GTC GGT TAT CAA ACT GCA AAC GGT AAG TAT AAA TCC GAA AGC      384
Glu Thr Val Gly Tyr Gln Thr Ala Asn Gly Lys Tyr Lys Ser Glu Ser
                390                 395                 400

TAT ACA GGT CAG TTA ATG GCT GGT TAT ACC TAT ATG ATG CCT GAG AAC      432
Tyr Thr Gly Gln Leu Met Ala Gly Tyr Thr Tyr Met Met Pro Glu Asn
            405                 410                 415

ATT AAC TTA ACA CCG CTA GCT GGG CTT AGA TAT TCG ACT ATC AAA GAT      480
Ile Asn Leu Thr Pro Leu Ala Gly Leu Arg Tyr Ser Thr Ile Lys Asp
420                 425                 430

AAG GGC TAT AAG GAA ACC GGT ACT ACT TAC CAA AAT CTT ACC GTT AAA      528
Lys Gly Tyr Lys Glu Thr Gly Thr Thr Tyr Gln Asn Leu Thr Val Lys
435                 440                 445                 450

GGC AAG AAC TAT AAT ACT TTC GAC GGT TTA CTC GGT GCT AAA GTA TCA      576
Gly Lys Asn Tyr Asn Thr Phe Asp Gly Leu Leu Gly Ala Lys Val Ser
                455                 460                 465

AGT AAT ATC AAT GTC AAT GAA ATA GTG CTA ACA CCT GAG CTT TAC GCA      624
Ser Asn Ile Asn Val Asn Glu Ile Val Leu Thr Pro Glu Leu Tyr Ala
            470                 475                 480

ATG GTC GAT TAT GCA TTC AAG AAT AAA GTT TCG GCG ATT GAT GCA AGG      672
Met Val Asp Tyr Ala Phe Lys Asn Lys Val Ser Ala Ile Asp Ala Arg
                485                 490                 495

TTA CAA GGT ATG ACT GCT CCT CTT CCA ACC AAC AGC TTT AAG CAA AGC      720
Leu Gln Gly Met Thr Ala Pro Leu Pro Thr Asn Ser Phe Lys Gln Ser
500                 505                 510

AAA ACA AGT TTT GAT GTC GGT GTC GGT GTT ACT GCT AAG CAT AAA ATG      768
Lys Thr Ser Phe Asp Val Gly Val Gly Val Thr Ala Lys His Lys Met
515                 520                 525                 530

ATG GAA TAC AGG ATT AAC TAC GAT ACC AAT ATC GGA AGT AAG TAT TTC      816
Met Glu Tyr Arg Ile Asn Tyr Asp Thr Asn Ile Gly Ser Lys Tyr Phe
                535                 540                 545

GCT CAG CAA GGT AGT GTA AAA GTT CGT GTT AAT TTT                      852
Ala Gln Gln Gly Ser Val Lys Val Arg Val Asn Phe
            550                 555
```

(2) INFORMATION FOR SEQ ID NO: 21:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO: 21:

```
Lys Phe Gly Ala Trp Ile Ser Pro Phe Val Gly Asn Ala Thr Gln Lys
1               5                   10                  15

Met Cys Asn Ser Ile Ser Gly Tyr Lys Ser Asp Thr Thr Gly Gly Thr
                20                  25                  30

Ile Gly Phe Asp Gly Phe Val Ser Asp Leu Ala Leu Gly Leu Ala
            35                  40                  45

Tyr Thr Arg Ala Asp Thr Asp Ile Lys Leu Lys Asn Asn Lys Thr Gly
        50                  55                  60

Asp Lys Asn Lys Val Glu Ser Asn Ile Tyr Ser Leu Tyr Gly Leu Tyr
65                  70                  75                  80
```

```
Asn Val Pro Tyr Glu Asn Leu Phe Val Glu Ala Ile Ala Ser Tyr Ser
                85                  90                  95

Asp Asn Lys Ile Arg Ser Lys Ser Arg Arg Val Ile Ala Thr Thr Leu
            100                 105                 110

Glu Thr Val Gly Tyr Gln Thr Ala Asn Gly Lys Tyr Lys Ser Glu Ser
            115                 120                 125

Tyr Thr Gly Gln Leu Met Ala Gly Tyr Thr Tyr Met Met Pro Glu Asn
            130                 135                 140

Ile Asn Leu Thr Pro Leu Ala Gly Leu Arg Tyr Ser Thr Ile Lys Asp
145                 150                 155                 160

Lys Gly Tyr Lys Glu Thr Gly Thr Thr Tyr Gln Asn Leu Thr Val Lys
                165                 170                 175

Gly Lys Asn Tyr Asn Thr Phe Asp Gly Leu Leu Gly Ala Lys Val Ser
            180                 185                 190

Ser Asn Ile Asn Val Asn Glu Ile Val Leu Thr Pro Glu Leu Tyr Ala
            195                 200                 205

Met Val Asp Tyr Ala Phe Lys Asn Lys Val Ser Ala Ile Asp Ala Arg
210                 215                 220

Leu Gln Gly Met Thr Ala Pro Leu Pro Thr Asn Ser Phe Lys Gln Ser
225                 230                 235                 240

Lys Thr Ser Phe Asp Val Gly Val Gly Val Thr Ala Lys His Lys Met
                245                 250                 255

Met Glu Tyr Arg Ile Asn Tyr Asp Thr Asn Ile Gly Ser Lys Tyr Phe
            260                 265                 270

Ala Gln Gln Gly Ser Val Lys Val Arg Val Asn Phe
            275                 280

(2) INFORMATION FOR SEQ ID NO: 22:

(i) SEQUENCE CHARACTERISTICS:
          (A) LENGTH: 855 base pairs
          (B) TYPE: nucleic acid
          (C) STRANDEDNESS: both
          (D) TOPOLOGY: linear (ix) FEATURE:
          (A) NAME/KEY: CDS
          (B) LOCATION:1..855

(xi) SEQUENCE DESCRIPTION: SEQ ID NO: 22:

TCT TAT GGT GTA TGG GCT AAA CCT TTC TAT AAC ATT GCA GAA CAA GAC      48
Ser Tyr Gly Val Trp Ala Lys Pro Phe Tyr Asn Ile Ala Glu Gln Asp
285                 290                 295                 300

AAA AAA GGT GGT ATA GCT GGT TAT AAA GCA AAA ACT ACT GGG GTT GTA      96
Lys Lys Gly Gly Ile Ala Gly Tyr Lys Ala Lys Thr Thr Gly Val Val
            305                 310                 315

GTT GGT TTA GAT ACT CTC GCT AGC GAT AAC CTA ATG ATT GGG GCA GCT     144
Val Gly Leu Asp Thr Leu Ala Ser Asp Asn Leu Met Ile Gly Ala Ala
            320                 325                 330

ATT GGG ATC ACT AAA ACT GAT ATA AAA CAC CAA GAT TAT AAG AAA GGT     192
Ile Gly Ile Thr Lys Thr Asp Ile Lys His Gln Asp Tyr Lys Lys Gly
            335                 340                 345

GAT AAA ACT GAT ATT AAT GGT TTA TCA TTC TCT CTA TAT GGT TCC CAA     240
Asp Lys Thr Asp Ile Asn Gly Leu Ser Phe Ser Leu Tyr Gly Ser Gln
350                 355                 360

CAG CTT GTT AAG AAT TTC TTT GCT CAA GGT AAT TCA ATC TTT ACC TTA     288
Gln Leu Val Lys Asn Phe Phe Ala Gln Gly Asn Ser Ile Phe Thr Leu
365                 370                 375                 380
```

```
AAC AAA GTC AAA AGT AAA AGT CAG CGT TAC TTC TTC GAG TCT AAT GGT         336
Asn Lys Val Lys Ser Lys Ser Gln Arg Tyr Phe Phe Glu Ser Asn Gly
            385                 390                 395

AAG ATG AGC AAG CAA ATT GCT GCT GGT AAT TAC GAT AAC ATG ACA TTT         384
Lys Met Ser Lys Gln Ile Ala Ala Gly Asn Tyr Asp Asn Met Thr Phe
                400                 405                 410

GGT GGT AAT TTA ATA TTT GGT TAT GAT TAT AAT GCA ATG CCA AAT GTA         432
Gly Gly Asn Leu Ile Phe Gly Tyr Asp Tyr Asn Ala Met Pro Asn Val
                415                 420                 425

TTA GTA ACT CCA ATG GCA GGA CTT AGC TAC TTA AAA TCT TCT AAT GAA         480
Leu Val Thr Pro Met Ala Gly Leu Ser Tyr Leu Lys Ser Ser Asn Glu
430                 435                 440

AAT TAT AAA GAA ACC GGT ACA ACA GTT GCA AAT AAG CGC ATT AAT AGC         528
Asn Tyr Lys Glu Thr Gly Thr Thr Val Ala Asn Lys Arg Ile Asn Ser
445                 450                 455                 460

AAA TTT AGT GAT AGA GTC GAT TTA ATA GTA GGG GCT AAA GTA GCT GGT         576
Lys Phe Ser Asp Arg Val Asp Leu Ile Val Gly Ala Lys Val Ala Gly
                465                 470                 475

AGT ACT GTG AAT ATA ACT GAT ATT GTG ATA TAT CCG GAA ATT CAT TCT         624
Ser Thr Val Asn Ile Thr Asp Ile Val Ile Tyr Pro Glu Ile His Ser
                480                 485                 490

TTT GTG GTG CAC AAA GTA AAT GGT AAA TTA TCT AAC TCT CAG TCT ATG         672
Phe Val Val His Lys Val Asn Gly Lys Leu Ser Asn Ser Gln Ser Met
                495                 500                 505

TTA GAT GGA CAA ACT GCT CCA TTT ATC AGT CAA CCT GAT AGA ACT GCT         720
Leu Asp Gly Gln Thr Ala Pro Phe Ile Ser Gln Pro Asp Arg Thr Ala
510                 515                 520

AAA ACG TCT TAT AAT ATA GGC TTA AGT GCA AAC ATA AAA TCT GAT GCT         768
Lys Thr Ser Tyr Asn Ile Gly Leu Ser Ala Asn Ile Lys Ser Asp Ala
525                 530                 535                 540

AAG ATG GAG TAT GGT ATC GGT TAT GAT TTT AAT TCT GCA AGT AAA TAT         816
Lys Met Glu Tyr Gly Ile Gly Tyr Asp Phe Asn Ser Ala Ser Lys Tyr
                545                 550                 555

ACT GCA CAT CAA GGT ACT TTA AAA GTA CGT GTA AAC TTC                     855
Thr Ala His Gln Gly Thr Leu Lys Val Arg Val Asn Phe
                560                 565

(2) INFORMATION FOR SEQ ID NO: 23:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO: 23:

Ser Tyr Gly Val Trp Ala Lys Pro Phe Tyr Asn Ile Ala Glu Gln Asp
1               5                   10                  15

Lys Lys Gly Gly Ile Ala Gly Tyr Lys Ala Lys Thr Thr Gly Val Val
                20                  25                  30

Val Gly Leu Asp Thr Leu Ala Ser Asp Asn Leu Met Ile Gly Ala Ala
            35                  40                  45

Ile Gly Ile Thr Lys Thr Asp Ile Lys His Gln Asp Tyr Lys Lys Gly
        50                  55                  60

Asp Lys Thr Asp Ile Asn Gly Leu Ser Phe Ser Leu Tyr Gly Ser Gln
65                  70                  75                  80

Gln Leu Val Lys Asn Phe Phe Ala Gln Gly Asn Ser Ile Phe Thr Leu
                85                  90                  95

Asn Lys Val Lys Ser Lys Ser Gln Arg Tyr Phe Phe Glu Ser Asn Gly
```

```
              100                 105                 110
Lys Met Ser Lys Gln Ile Ala Ala Gly Asn Tyr Asp Asn Met Thr Phe
            115                 120                 125
Gly Gly Asn Leu Ile Phe Gly Tyr Asp Tyr Asn Ala Met Pro Asn Val
        130                 135                 140
Leu Val Thr Pro Met Ala Gly Leu Ser Tyr Leu Lys Ser Ser Asn Glu
145                 150                 155                 160
Asn Tyr Lys Glu Thr Gly Thr Thr Val Ala Asn Lys Arg Ile Asn Ser
                165                 170                 175
Lys Phe Ser Asp Arg Val Asp Leu Ile Val Gly Ala Lys Val Ala Gly
            180                 185                 190
Ser Thr Val Asn Ile Thr Asp Ile Val Ile Tyr Pro Glu Ile His Ser
                195                 200                 205
Phe Val Val His Lys Val Asn Gly Lys Leu Ser Asn Ser Gln Ser Met
        210                 215                 220
Leu Asp Gly Gln Thr Ala Pro Phe Ile Ser Gln Pro Asp Arg Thr Ala
225                 230                 235                 240
Lys Thr Ser Tyr Asn Ile Gly Leu Ser Ala Asn Ile Lys Ser Asp Ala
                245                 250                 255
Lys Met Glu Tyr Gly Ile Gly Tyr Asp Phe Asn Ser Ala Ser Lys Tyr
            260                 265                 270
Thr Ala His Gln Gly Thr Leu Lys Val Arg Val Asn Phe
            275                 280                 285

(2) INFORMATION FOR SEQ ID NO: 24:

(i) SEQUENCE CHARACTERISTICS:
        (A) LENGTH: 855 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..855

(xi) SEQUENCE DESCRIPTION: SEQ ID NO: 24:

GCT TAC GGT ATA TGG GCA AAA CCT TTC TAT ACT GAT GCA CAT CAA AGT        48
Ala Tyr Gly Ile Trp Ala Lys Pro Phe Tyr Thr Asp Ala His Gln Ser
            290                 295                 300

AAG AAA GGT GGT TTA GCT GGT TAT AAA GCT AAA ACC ACC GGT GTC GTA        96
Lys Lys Gly Gly Leu Ala Gly Tyr Lys Ala Lys Thr Thr Gly Val Val
        305                 310                 315

ATC GGT TTA GAT ACG CTA GCT AAC GAT AAT TTA ATG ATC GGT GCT GCT       144
Ile Gly Leu Asp Thr Leu Ala Asn Asp Asn Leu Met Ile Gly Ala Ala
    320                 325                 330

ATC GGT ATC ACT AAA ACT GAT ATA AAA CAT CAA GAT TAT AAG AAA GGT       192
Ile Gly Ile Thr Lys Thr Asp Ile Lys His Gln Asp Tyr Lys Lys Gly
335                 340                 345

GAT AAA ACC GAC GTT AAC GGT TTC TCA TTC TCT CTA TAT GGT GCC CAG       240
Asp Lys Thr Asp Val Asn Gly Phe Ser Phe Ser Leu Tyr Gly Ala Gln
350                 355                 360                 365

CAG CTT GTT AAG AAC TTC TTT GCT CAA GGT AGT GCA ATA TTT AGC TTA       288
Gln Leu Val Lys Asn Phe Phe Ala Gln Gly Ser Ala Ile Phe Ser Leu
                370                 375                 380

AAC CAA GTG AAG AAC AAA AGT CAG CGT TAC TTC TTC GAT GCT AAC GGT       336
Asn Gln Val Lys Asn Lys Ser Gln Arg Tyr Phe Phe Asp Ala Asn Gly
            385                 390                 395

AAT ATG AGC AAG CAA ATT GCT GCC GGT CAT TAC GAT AAC ATG ACA TTT       384
```

```
Asn Met Ser Lys Gln Ile Ala Ala Gly His Tyr Asp Asn Met Thr Phe
            400                 405                 410
GGT GGT AAC TTA ACA GTC GGT TAT GAT TAC AAT GCA ATG CAA GGT GTG        432
Gly Gly Asn Leu Thr Val Gly Tyr Asp Tyr Asn Ala Met Gln Gly Val
        415                 420                 425
TTA GTA ACT CCA ATG GCA GGA CTT AGC TAC TTA AAG TCT TCT GAC GAA        480
Leu Val Thr Pro Met Ala Gly Leu Ser Tyr Leu Lys Ser Ser Asp Glu
430                 435                 440                 445
AAC TAC AAA GAA ACC GGT ACA ACA GTT GCA AAC AAG CAA GTT AAC AGC        528
Asn Tyr Lys Glu Thr Gly Thr Thr Val Ala Asn Lys Gln Val Asn Ser
                450                 455                 460
AAA TTT AGC GAT AGA ACC GAT TTA ATA GTA GGT GCT AAA GTA GCC GGC        576
Lys Phe Ser Asp Arg Thr Asp Leu Ile Val Gly Ala Lys Val Ala Gly
                    465                 470                 475
AGT ACT ATG AAC ATA ACT GAT CTT GCG GTA TAT CCA GAA GTT CAC GCT        624
Ser Thr Met Asn Ile Thr Asp Leu Ala Val Tyr Pro Glu Val His Ala
                480                 485                 490
TTT GTG GTT CAC AAA GTA ACC GGT AGA TTA TCT AAA ACT CAG TCT GTA        672
Phe Val Val His Lys Val Thr Gly Arg Leu Ser Lys Thr Gln Ser Val
        495                 500                 505
TTA GAC GGA CAA GTT ACT CCG TGT ATC AAC CAG CCT GAC AGA ACC ACT        720
Leu Asp Gly Gln Val Thr Pro Cys Ile Asn Gln Pro Asp Arg Thr Thr
510                 515                 520                 525
AAA ACA TCT TAT AAT TTA GGT TTA AGT GCA AGC ATA AGA TCT GAT GCT        768
Lys Thr Ser Tyr Asn Leu Gly Leu Ser Ala Ser Ile Arg Ser Asp Ala
                530                 535                 540
AAG ATG GAG TAC GGA ATC GGT TAC GAT GCT CAG ATT TCA AGT AAA TAT        816
Lys Met Glu Tyr Gly Ile Gly Tyr Asp Ala Gln Ile Ser Ser Lys Tyr
                545                 550                 555
ACT GCA CAT CAA GGT ACT CTA AAA GTC CGT GTA AAC TTC                    855
Thr Ala His Gln Gly Thr Leu Lys Val Arg Val Asn Phe
                560                 565                 570

(2) INFORMATION FOR SEQ ID NO: 25:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO: 25:

Ala Tyr Gly Ile Trp Ala Lys Pro Phe Tyr Thr Asp Ala His Gln Ser
1               5                   10                  15
Lys Lys Gly Gly Leu Ala Gly Tyr Lys Ala Lys Thr Thr Gly Val Val
                20                  25                  30
Ile Gly Leu Asp Thr Leu Ala Asn Asp Asn Leu Met Ile Gly Ala Ala
            35                  40                  45
Ile Gly Ile Thr Lys Thr Asp Ile Lys His Gln Asp Tyr Lys Lys Gly
        50                  55                  60
Asp Lys Thr Asp Val Asn Gly Phe Ser Phe Ser Leu Tyr Gly Ala Gln
65                  70                  75                  80
Gln Leu Val Lys Asn Phe Phe Ala Gln Gly Ser Ala Ile Phe Ser Leu
                85                  90                  95
Asn Gln Val Lys Asn Lys Ser Gln Arg Tyr Phe Phe Asp Ala Asn Gly
            100                 105                 110
Asn Met Ser Lys Gln Ile Ala Ala Gly His Tyr Asp Asn Met Thr Phe
        115                 120                 125
```

-continued

```
Gly Gly Asn Leu Thr Val Gly Tyr Asp Tyr Asn Ala Met Gln Gly Val
        130                 135                 140

Leu Val Thr Pro Met Ala Gly Leu Ser Tyr Leu Lys Ser Ser Asp Glu
145                 150                 155                 160

Asn Tyr Lys Glu Thr Gly Thr Thr Val Ala Asn Lys Gln Val Asn Ser
                165                 170                 175

Lys Phe Ser Asp Arg Thr Asp Leu Ile Val Gly Ala Lys Val Ala Gly
                180                 185                 190

Ser Thr Met Asn Ile Thr Asp Leu Ala Val Tyr Pro Glu Val His Ala
                195                 200                 205

Phe Val Val His Lys Val Thr Gly Arg Leu Ser Lys Thr Gln Ser Val
        210                 215                 220

Leu Asp Gly Gln Val Thr Pro Cys Ile Asn Gln Pro Asp Arg Thr Thr
225                 230                 235                 240

Lys Thr Ser Tyr Asn Leu Gly Leu Ser Ala Ser Ile Arg Ser Asp Ala
                245                 250                 255

Lys Met Glu Tyr Gly Ile Gly Tyr Asp Ala Gln Ile Ser Ser Lys Tyr
                260                 265                 270

Thr Ala His Gln Gly Thr Leu Lys Val Arg Val Asn Phe
        275                 280                 285
```

(2) INFORMATION FOR SEQ ID NO: 26:

(i) SEQUENCE CHARACTERISTICS:
        (A) LENGTH: 855 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..855

(xi) SEQUENCE DESCRIPTION: SEQ ID NO: 26:

```
TCT TAT GGT GTA TGG GCT AAA CCT TTC TAT AAC ATC GCA GAA CAA GAT      48
Ser Tyr Gly Val Trp Ala Lys Pro Phe Tyr Asn Ile Ala Glu Gln Asp
            290                 295                 300

AAA AAA GGT GGT CTA GCT GGT TAT AAA GCA AAA ACT GCT GGT GTT GTA      96
Lys Lys Gly Gly Leu Ala Gly Tyr Lys Ala Lys Thr Ala Gly Val Val
            305                 310                 315

GTT GGT TTA GAT ACT CTC GCT AAT GAT AAC CTA ATG ATT GGT GCA GCT     144
Val Gly Leu Asp Thr Leu Ala Asn Asp Asn Leu Met Ile Gly Ala Ala
            320                 325                 330

ATT GGT ATC ACT AAA ACT GAC ATA AAA CAC CAA GAT TAT AAA AAA GGT     192
Ile Gly Ile Thr Lys Thr Asp Ile Lys His Gln Asp Tyr Lys Lys Gly
            335                 340                 345

GAT AAA ACT GAT ATT AAG GGT TTA TCC TTC TCT CTA TAT GGT GCC CAG     240
Asp Lys Thr Asp Ile Lys Gly Leu Ser Phe Ser Leu Tyr Gly Ala Gln
350                 355                 360                 365

CAG CTT GTT AAG AAT TTC TTT GCT CAA GGT AGT GCA ATA TTT ACC TTA     288
Gln Leu Val Lys Asn Phe Phe Ala Gln Gly Ser Ala Ile Phe Thr Leu
                370                 375                 380

AAC AAA GTC AAA AGT AAA AGT CAG CGT TAC TTC TTC GAT GCT AAT GGT     336
Asn Lys Val Lys Ser Lys Ser Gln Arg Tyr Phe Phe Asp Ala Asn Gly
                385                 390                 395

AAG ATG AAC AAG CAA ATT GCT GCC GGT AAT TAT GAT AAC ATA ACA TTC     384
Lys Met Asn Lys Gln Ile Ala Ala Gly Asn Tyr Asp Asn Ile Thr Phe
            400                 405                 410

GGT GGT AAT TTA ATG TTT GGT TAT GAT TAT AAT GCA CTG CAA GGT GTA     432
Gly Gly Asn Leu Met Phe Gly Tyr Asp Tyr Asn Ala Leu Gln Gly Val
```

-continued

```
               415                 420                 425
TTA GTG ACT CCA ATG GCA GGG CTT AGC TAC TTA AAA TCT TCT AAT GAA       480
Leu Val Thr Pro Met Ala Gly Leu Ser Tyr Leu Lys Ser Ser Asn Glu
430                 435                 440                 445

AAC TAT AAA GAA ACT GGT ACA GTT GCA AAT AAG CGC ATT CAC AGC           528
Asn Tyr Lys Glu Thr Gly Thr Thr Val Ala Asn Lys Arg Ile His Ser
                450                 455                 460

AAA TTT AGT GAT AGA ATC GAT TTA ATA GTA GGT GCT AAA GTA ACT GGT       576
Lys Phe Ser Asp Arg Ile Asp Leu Ile Val Gly Ala Lys Val Thr Gly
                    465                 470                 475

AGT GCT ATG AAT ATA AAT GAT ATT GTG ATA TAT CCA GAA ATT CAT TCT       624
Ser Ala Met Asn Ile Asn Asp Ile Val Ile Tyr Pro Glu Ile His Ser
                480                 485                 490

TTT GTA GTG CAC AAA GTA AAT GGT AAG CTA TCT AAG GCT CAG TCT ATG       672
Phe Val Val His Lys Val Asn Gly Lys Leu Ser Lys Ala Gln Ser Met
                    495                 500                 505

TTA GAT GGA CAA ACT GCT CCA TTT ATC AGT CAG CCT GAT AGA ACT GCT       720
Leu Asp Gly Gln Thr Ala Pro Phe Ile Ser Gln Pro Asp Arg Thr Ala
510                 515                 520                 525

AAA ACA TCT TAT AAT ATA GGC TTA AGT GCA AAT ATA AGA TCT GAT GCT       768
Lys Thr Ser Tyr Asn Ile Gly Leu Ser Ala Asn Ile Arg Ser Asp Ala
                530                 535                 540

AAG ATG GAG TAT GGT ATC GGT TAT GAT TTT AAT GCT GCA AGT AAA TAT       816
Lys Met Glu Tyr Gly Ile Gly Tyr Asp Phe Asn Ala Ala Ser Lys Tyr
                    545                 550                 555

ACT GCA CAT CAA GGT ACT TTA AAA GTA CGT ATA AAT TTC                   855
Thr Ala His Gln Gly Thr Leu Lys Val Arg Ile Asn Phe
560                 565                 570

(2) INFORMATION FOR SEQ ID NO: 27:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO: 27:

Ser Tyr Gly Val Trp Ala Lys Pro Phe Tyr Asn Ile Ala Glu Gln Asp
1               5                   10                  15

Lys Lys Gly Gly Leu Ala Gly Tyr Lys Ala Lys Thr Ala Gly Val Val
                20                  25                  30

Val Gly Leu Asp Thr Leu Ala Asn Asp Asn Leu Met Ile Gly Ala Ala
            35                  40                  45

Ile Gly Ile Thr Lys Thr Asp Ile Lys His Gln Asp Tyr Lys Lys Gly
        50                  55                  60

Asp Lys Thr Asp Ile Lys Gly Leu Ser Phe Ser Leu Tyr Gly Ala Gln
65                  70                  75                  80

Gln Leu Val Lys Asn Phe Ala Gln Gly Ser Ala Ile Phe Thr Leu
                85                  90                  95

Asn Lys Val Lys Ser Lys Ser Gln Arg Tyr Phe Phe Asp Ala Asn Gly
                100                 105                 110

Lys Met Asn Lys Gln Ile Ala Ala Gly Asn Tyr Asp Asn Ile Thr Phe
                115                 120                 125

Gly Gly Asn Leu Met Phe Gly Tyr Asp Tyr Asn Ala Leu Gln Gly Val
            130                 135                 140

Leu Val Thr Pro Met Ala Gly Leu Ser Tyr Leu Lys Ser Ser Asn Glu
145                 150                 155                 160
```

```
Asn Tyr Lys Glu Thr Gly Thr Thr Val Ala Asn Lys Arg Ile His Ser
            165                 170                 175

Lys Phe Ser Asp Arg Ile Asp Leu Ile Val Gly Ala Lys Val Thr Gly
            180                 185                 190

Ser Ala Met Asn Ile Asn Asp Ile Val Ile Tyr Pro Glu Ile His Ser
            195                 200                 205

Phe Val Val His Lys Val Asn Gly Lys Leu Ser Lys Ala Gln Ser Met
            210                 215                 220

Leu Asp Gly Gln Thr Ala Pro Phe Ile Ser Gln Pro Asp Arg Thr Ala
225                 230                 235                 240

Lys Thr Ser Tyr Asn Ile Gly Leu Ser Ala Asn Ile Arg Ser Asp Ala
            245                 250                 255

Lys Met Glu Tyr Gly Ile Gly Tyr Asp Phe Asn Ala Ala Ser Lys Tyr
            260                 265                 270

Thr Ala His Gln Gly Thr Leu Lys Val Arg Ile Asn Phe
            275                 280                 285

(2) INFORMATION FOR SEQ ID NO: 28:

(i) SEQUENCE CHARACTERISTICS:
        (A) LENGTH: 795 base pairs
        (B) TYPE: nucleic acid
        (C) STRANDEDNESS: both
        (D) TOPOLOGY: linear (ix) FEATURE:
         (A) NAME/KEY: CDS
         (B) LOCATION:1..795

(xi) SEQUENCE DESCRIPTION: SEQ ID NO: 28:

CAG GGG GAT GCC GGT GTC TGG GCA CGC ATA ATG AAT GGT ACC GGT TCG      48
Gln Gly Asp Ala Gly Val Trp Ala Arg Ile Met Asn Gly Thr Gly Ser
            290                 295                 300

GCA GAT GGT GAC TAC AGC GAT AAC TAC ACT CAC GTT CAG ATT GGT GTC      96
Ala Asp Gly Asp Tyr Ser Asp Asn Tyr Thr His Val Gln Ile Gly Val
            305                 310                 315

GAC AGA AAG CAT GAG CTG GAC GGT GTG GAT TTA TTT ACG GGG GCA TTG     144
Asp Arg Lys His Glu Leu Asp Gly Val Asp Leu Phe Thr Gly Ala Leu
            320                 325                 330

CTG ACC TAT ACG GAC AGC AAT GCA AGC AGC CAC GCA TTC AGT GGA AAA     192
Leu Thr Tyr Thr Asp Ser Asn Ala Ser Ser His Ala Phe Ser Gly Lys
            335                 340                 345

AAC AAA TCC GTG GGT GGC GGT CTG TAT GCC TCT GCA CTC TTT AAT TCC     240
Asn Lys Ser Val Gly Gly Gly Leu Tyr Ala Ser Ala Leu Phe Asn Ser
350                 355                 360                 365

GGA GCT TAT TTT GAC CTG ATT GGT AAA TAT CTC CAT CAT GAT AAT CAG     288
Gly Ala Tyr Phe Asp Leu Ile Gly Lys Tyr Leu His His Asp Asn Gln
            370                 375                 380

CAC ACG GCG AAT TTT GCC TCA CTG GGA ACA AAA GAC TAC AGC TCT CAT     336
His Thr Ala Asn Phe Ala Ser Leu Gly Thr Lys Asp Tyr Ser Ser His
            385                 390                 395

TCC TGG TAT GCC GGT GCT GAA GTT GGT TAT CGT TAC CAC CTG ACG AAA     384
Ser Trp Tyr Ala Gly Ala Glu Val Gly Tyr Arg Tyr His Leu Thr Lys
            400                 405                 410

GAG TCC TGG GTG GAG CCA CAG ATA GAG CTG GTT TAC GGT TCT GTA TCA     432
Glu Ser Trp Val Glu Pro Gln Ile Glu Leu Val Tyr Gly Ser Val Ser
            415                 420                 425

GGA AAA GCT TTT AGC TGG GAA GCC CGG GGA ATG GCT CTG AGC ATG AAA     480
Gly Lys Ala Phe Ser Trp Glu Ala Arg Gly Met Ala Leu Ser Met Lys
430                 435                 440                 445
```

```
GAC AAG GAT TAT AAC CCA CTG ATT GGC CGT ACT GGT GTT GAC GTG GGA      528
Asp Lys Asp Tyr Asn Pro Leu Ile Gly Arg Thr Gly Val Asp Val Gly
            450                 455                 460

AGA GCC TTC TCC GGA GAC GAC TGG AAA ATC ACA GCT CGA GCC GGG CTG      576
Arg Ala Phe Ser Gly Asp Asp Trp Lys Ile Thr Ala Arg Ala Gly Leu
            465                 470                 475

GGT TAT CAG TTC GAC CTG CTG GCG AAC GGA GAA ACG GTT CTG CAG GAT      624
Gly Tyr Gln Phe Asp Leu Leu Ala Asn Gly Glu Thr Val Leu Gln Asp
            480                 485                 490

GCT TCC GGA GAG AAA CGT TTC GAA GGT GAA AAA GAT AGC AGG ATG CTG      672
Ala Ser Gly Glu Lys Arg Phe Glu Gly Glu Lys Asp Ser Arg Met Leu
    495                 500                 505

ATG ACG GTA GGG ATG AAT GCG GAA ATT AAG GAT AAT ATG CGT TTG GGA      720
Met Thr Val Gly Met Asn Ala Glu Ile Lys Asp Asn Met Arg Leu Gly
510                 515                 520                 525

CTG GAG CTG GAG AAA TCA GCG TTC GGG AAA TAT AAT GTG GAT AAT GCG      768
Leu Glu Leu Glu Lys Ser Ala Phe Gly Lys Tyr Asn Val Asp Asn Ala
                530                 535                 540

ATA AAC GCC AAC TTC CGT TAT GTT TTC                                  795
Ile Asn Ala Asn Phe Arg Tyr Val Phe
            545                 550

(2) INFORMATION FOR SEQ ID NO: 29:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO: 29:

Gln Gly Asp Ala Gly Val Trp Ala Arg Ile Met Asn Gly Thr Gly Ser
  1               5                  10                  15

Ala Asp Gly Asp Tyr Ser Asp Asn Tyr Thr His Val Gln Ile Gly Val
                20                  25                  30

Asp Arg Lys His Glu Leu Asp Gly Val Asp Leu Phe Thr Gly Ala Leu
            35                  40                  45

Leu Thr Tyr Thr Asp Ser Asn Ala Ser Ser His Ala Phe Ser Gly Lys
        50                  55                  60

Asn Lys Ser Val Gly Gly Leu Tyr Ala Ser Ala Leu Phe Asn Ser
 65                 70                  75                  80

Gly Ala Tyr Phe Asp Leu Ile Gly Lys Tyr Leu His His Asp Asn Gln
                85                  90                  95

His Thr Ala Asn Phe Ala Ser Leu Gly Thr Lys Asp Tyr Ser Ser His
            100                 105                 110

Ser Trp Tyr Ala Gly Ala Glu Val Gly Tyr Arg Tyr His Leu Thr Lys
        115                 120                 125

Glu Ser Trp Val Glu Pro Gln Ile Glu Leu Val Tyr Gly Ser Val Ser
    130                 135                 140

Gly Lys Ala Phe Ser Trp Glu Ala Arg Gly Met Ala Leu Ser Met Lys
145                 150                 155                 160

Asp Lys Asp Tyr Asn Pro Leu Ile Gly Arg Thr Gly Val Asp Val Gly
                165                 170                 175

Arg Ala Phe Ser Gly Asp Asp Trp Lys Ile Thr Ala Arg Ala Gly Leu
            180                 185                 190

Gly Tyr Gln Phe Asp Leu Leu Ala Asn Gly Glu Thr Val Leu Gln Asp
        195                 200                 205
```

```
Ala Ser Gly Glu Lys Arg Phe Glu Gly Glu Lys Asp Ser Arg Met Leu
    210                 215                 220
Met Thr Val Gly Met Asn Ala Glu Ile Lys Asp Asn Met Arg Leu Gly
225                 230                 235                 240
Leu Glu Leu Glu Lys Ser Ala Phe Gly Lys Tyr Asn Val Asp Asn Ala
                245                 250                 255
Ile Asn Ala Asn Phe Arg Tyr Val Phe
            260                 265
```

(2) INFORMATION FOR SEQ ID NO: 30:

(i) SEQUENCE CHARACTERISTICS:
        (A) LENGTH: 957 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..957

(xi) SEQUENCE DESCRIPTION: SEQ ID NO: 30:

```
ACC CGT CAA CTG TCC GGC CAG ATC CAC GCG GAT ATG GCG TCC GCC CAG       48
Thr Arg Gln Leu Ser Gly Gln Ile His Ala Asp Met Ala Ser Ala Gln
                270                 275                 280

ATT AAC GAA AGC CGT TAT CTG CGC GAT ACC GCC ACC GAG CGG TTG CGC       96
Ile Asn Glu Ser Arg Tyr Leu Arg Asp Thr Ala Thr Glu Arg Leu Arg
            285                 290                 295

CAG GCC GAT GGC CGC CGC ACC GCT TCC GAT ATC AAA GCG GAT GAT AAT      144
Gln Ala Asp Gly Arg Arg Thr Ala Ser Asp Ile Lys Ala Asp Asp Asn
        300                 305                 310

GGC GCC TGG GCG AAA TTG CTG GGC AAC TGG GGG CAT GCT TCC GGC AAC      192
Gly Ala Trp Ala Lys Leu Leu Gly Asn Trp Gly His Ala Ser Gly Asn
    315                 320                 325

GAC AAC GCT ACC GGT TAC CAG ACA TCC ACC TAT GGC GTG CTG TTG GGT      240
Asp Asn Ala Thr Gly Tyr Gln Thr Ser Thr Tyr Gly Val Leu Leu Gly
330                 335                 340                 345

CTG GAC AGC GAA CTG TTT GAC GAC GGC CGG CTG GGC GTG ATG ACC GGG      288
Leu Asp Ser Glu Leu Phe Asp Asp Gly Arg Leu Gly Val Met Thr Gly
                350                 355                 360

TAT ACC CGC ACG TCG CTG GTA GGC GGT CTA CAG TCA GTA GTC CAC AGC      336
Tyr Thr Arg Thr Ser Leu Val Gly Gly Leu Gln Ser Val Val His Ser
            365                 370                 375

GAC ACT ACA CAT CTG GGG CTG TAC GGC GAC AAA CGC TTC GGC GCG TTG      384
Asp Thr Thr His Leu Gly Leu Tyr Gly Asp Lys Arg Phe Gly Ala Leu
        380                 385                 390

GCG CTG CCA GCG GGC GGC ACC TAT ACC TGG CAT CGC ATC GAC ACG TCG      432
Ala Leu Pro Ala Gly Gly Thr Tyr Thr Trp His Arg Ile Asp Thr Ser
    395                 400                 405

CGC TCG GTA AAC TAC GGC GCG CAG GCG GAT CGC GAA AAG GCC CGC TAT      480
Arg Ser Val Asn Tyr Gly Ala Gln Ala Asp Arg Glu Lys Ala Arg Tyr
410                 415                 420                 425

AAC GCG CGC ACC GGT CAG CTG TTT ATC GAA AGC GGC TAC GAT TGG AGC      528
Asn Ala Arg Thr Gly Gln Leu Phe Ile Glu Ser Gly Tyr Asp Trp Ser
                430                 435                 440

AAC GAC GTG GTC AAT CTT GAG CCG TTC GCC AAC CTG GCG TAC ACC CAC      576
Asn Asp Val Val Asn Leu Glu Pro Phe Ala Asn Leu Ala Tyr Thr His
            445                 450                 455

TAT CGC AAC GAG GGG ATC AAC GAG CAA GGC GGG GCG GCG GCG CTG CGC      624
Tyr Arg Asn Glu Gly Ile Asn Glu Gln Gly Gly Ala Ala Ala Leu Arg
        460                 465                 470
```

```
GGC GAT AAG CAA AGT CAG TCC GCC ACC GCT TCG ACG CTG GGC CTG CGC      672
Gly Asp Lys Gln Ser Gln Ser Ala Thr Ala Ser Thr Leu Gly Leu Arg
    475                 480                 485

GCC GAT ACG CAA TGG CAG ACC GAC AGC GTG GCG ATC GCC CTG CCG GGC      720
Ala Asp Thr Gln Trp Gln Thr Asp Ser Val Ala Ile Ala Leu Pro Gly
490                 495                 500                 505

GAG CTG GGT TGG CAA CAT CAG TAC GGC AAG CTG GAG CGT AAA ACA CAG      768
Glu Leu Gly Trp Gln His Gln Tyr Gly Lys Leu Glu Arg Lys Thr Gln
                510                 515                 520

CTG ATG TTC AAA CGC AGC GAT GTC GCG TTC GAC GTG AAC AGC GTC CCT      816
Leu Met Phe Lys Arg Ser Asp Val Ala Phe Asp Val Asn Ser Val Pro
            525                 530                 535

GTT TCT CGC GAT GGG GCC ATT CTG AAA GCG GGC GTC GAT GTA TCG ATT      864
Val Ser Arg Asp Gly Ala Ile Leu Lys Ala Gly Val Asp Val Ser Ile
        540                 545                 550

AAC AAA AAC GTC GTC CTG TCC CTT GGG TAC GGC GGG CAG CTG TCG TCC      912
Asn Lys Asn Val Val Leu Ser Leu Gly Tyr Gly Gly Gln Leu Ser Ser
    555                 560                 565

AAC CAC CAG GAC AAC AGC GTC AAC GCC GGC CTG ACC TGG CGG TTC          957
Asn His Gln Asp Asn Ser Val Asn Ala Gly Leu Thr Trp Arg Phe
570                 575                 580
```

(2) INFORMATION FOR SEQ ID NO: 31:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 31:

```
Thr Arg Gln Leu Ser Gly Gln Ile His Ala Asp Met Ala Ser Ala Gln
1               5                   10                  15

Ile Asn Glu Ser Arg Tyr Leu Arg Asp Thr Ala Thr Glu Arg Leu Arg
            20                  25                  30

Gln Ala Asp Gly Arg Arg Thr Ala Ser Asp Ile Lys Ala Asp Asp Asn
        35                  40                  45

Gly Ala Trp Ala Lys Leu Leu Gly Asn Trp Gly His Ala Ser Gly Asn
    50                  55                  60

Asp Asn Ala Thr Gly Tyr Gln Thr Ser Thr Tyr Gly Val Leu Leu Gly
65                  70                  75                  80

Leu Asp Ser Glu Leu Phe Asp Asp Gly Arg Leu Gly Val Met Thr Gly
                85                  90                  95

Tyr Thr Arg Thr Ser Leu Val Gly Gly Leu Gln Ser Val Val His Ser
            100                 105                 110

Asp Thr Thr His Leu Gly Leu Tyr Gly Asp Lys Arg Phe Gly Ala Leu
        115                 120                 125

Ala Leu Pro Ala Gly Gly Thr Tyr Thr Trp His Arg Ile Asp Thr Ser
    130                 135                 140

Arg Ser Val Asn Tyr Gly Ala Gln Ala Asp Arg Glu Lys Ala Arg Tyr
145                 150                 155                 160

Asn Ala Arg Thr Gly Gln Leu Phe Ile Glu Ser Gly Tyr Asp Trp Ser
                165                 170                 175

Asn Asp Val Val Asn Leu Glu Pro Phe Ala Asn Leu Ala Tyr Thr His
            180                 185                 190

Tyr Arg Asn Glu Gly Ile Asn Glu Gln Gly Gly Ala Ala Ala Leu Arg
        195                 200                 205
```

```
Gly Asp Lys Gln Ser Gln Ser Ala Thr Ala Ser Thr Leu Gly Leu Arg
    210                 215                 220

Ala Asp Thr Gln Trp Gln Thr Asp Ser Val Ala Ile Ala Leu Pro Gly
225                 230                 235                 240

Glu Leu Gly Trp Gln His Gln Tyr Gly Lys Leu Arg Lys Thr Gln
                245                 250                 255

Leu Met Phe Lys Arg Ser Asp Val Ala Phe Asp Val Asn Ser Val Pro
                260                 265                 270

Val Ser Arg Asp Gly Ala Ile Leu Lys Ala Gly Val Asp Val Ser Ile
            275                 280                 285

Asn Lys Asn Val Val Leu Ser Leu Gly Tyr Gly Gly Gln Leu Ser Ser
    290                 295                 300

Asn His Gln Asp Asn Ser Val Asn Ala Gly Leu Thr Trp Arg Phe
305                 310                 315
```

(2) INFORMATION FOR SEQ ID NO: 32:

(i) SEQUENCE CHARACTERISTICS:
        (A) LENGTH: 957 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..957

(xi) SEQUENCE DESCRIPTION: SEQ ID NO: 32:

```
ACC CGT CAA CTG TCC GGC CAG ATC CAC GCG GAT ATG GCT TCC GCC CAG      48
Thr Arg Gln Leu Ser Gly Gln Ile His Ala Asp Met Ala Ser Ala Gln
320                 325                 330                 335

ATC AAC GAA AGC CGT TAC CTG CGC GAT ACC GCC ACC GAG CGC TTG CGC      96
Ile Asn Glu Ser Arg Tyr Leu Arg Asp Thr Ala Thr Glu Arg Leu Arg
                340                 345                 350

CAG GCG GAA GGC CGC CGC ACC GCT ACC GAC ATT AAA GCG GAT GAC AAC     144
Gln Ala Glu Gly Arg Arg Thr Ala Thr Asp Ile Lys Ala Asp Asp Asn
            355                 360                 365

GGC GCC TGG GCG AAA CTG CTG GGT AGC TGG GGG CAT GCT TCC GGC AAC     192
Gly Ala Trp Ala Lys Leu Leu Gly Ser Trp Gly His Ala Ser Gly Asn
    370                 375                 380

GAC AAC GCC ACC GGT TAC CAG ACC TCC ACC TAT GGC GTG CTG TTA GGT     240
Asp Asn Ala Thr Gly Tyr Gln Thr Ser Thr Tyr Gly Val Leu Leu Gly
385                 390                 395

CTG GAC AGC GAA CTG TTT GGC GAC GGC CGG CTT GGC ATG ATG ACC GGG     288
Leu Asp Ser Glu Leu Phe Gly Asp Gly Arg Leu Gly Met Met Thr Gly
400                 405                 410                 415

TAT ACC CGC ACT TCG CTG GAT GGA GGT TAT CAG TCA GAT GCT CAC AGC     336
Tyr Thr Arg Thr Ser Leu Asp Gly Gly Tyr Gln Ser Asp Ala His Ser
                420                 425                 430

GAC AAC TAC CAT CTG GGG CTG TAC GGC GAC AAA CGC TTC GGC GCG TTG     384
Asp Asn Tyr His Leu Gly Leu Tyr Gly Asp Lys Arg Phe Gly Ala Leu
            435                 440                 445

GCG CTG CGA GCG GGC GGC ACC TAT ACC TGG CAT CGC ATC GAC ACC TCG     432
Ala Leu Arg Ala Gly Gly Thr Tyr Thr Trp His Arg Ile Asp Thr Ser
    450                 455                 460

CGT TCG GTG AAC TAC GGC GCG CAG TCG GAT CGC GAG AAG GCC AAG TAT     480
Arg Ser Val Asn Tyr Gly Ala Gln Ser Asp Arg Glu Lys Ala Lys Tyr
465                 470                 475

AAC GCG CGC ACC GGT CAG CTG TTC ATC GAA AGC GGC TAC GAT TGG ACG     528
Asn Ala Arg Thr Gly Gln Leu Phe Ile Glu Ser Gly Tyr Asp Trp Thr
```

```
                480                 485                 490                 495
AGC GAT GCG GTC AAC CTT GAG CCG TTC GCC AAC CTG GCG TAT ACC CAT                576
Ser Asp Ala Val Asn Leu Glu Pro Phe Ala Asn Leu Ala Tyr Thr His
                500                 505                 510

TAC CGT AAC GAG GAG ATC AAC GAG CAA GGC GGG GCA GCG GCG CTG CGC                624
Tyr Arg Asn Glu Glu Ile Asn Glu Gln Gly Gly Ala Ala Ala Leu Arg
                515                 520                 525

GGC GAC AAA CAA AGT CAG TCC GCC ACC GCC TCG ACG TTG GGT CTG CGC                672
Gly Asp Lys Gln Ser Gln Ser Ala Thr Ala Ser Thr Leu Gly Leu Arg
            530                 535                 540

GCC GAC ACC GAG TGG CAA ACC GAC AGC GTG GCG ATC GCG CTG CGC GGC                720
Ala Asp Thr Glu Trp Gln Thr Asp Ser Val Ala Ile Ala Leu Arg Gly
            545                 550                 555

GAG CTG GGT TGG CAG CAT CAG TAC GGC AAG CTG GAG CGT AAA ACG CAG                768
Glu Leu Gly Trp Gln His Gln Tyr Gly Lys Leu Glu Arg Lys Thr Gln
560                 565                 570                 575

CTG ATG TTC AAA CGC ACT GAT GCG GCG TTC GAC GTG AAC AGC GTG CCT                816
Leu Met Phe Lys Arg Thr Asp Ala Ala Phe Asp Val Asn Ser Val Pro
                580                 585                 590

GTT TCT CGC GAT GGC GCG ATT CTG AAA GCG GGC GTC GAT GTA TCG ATT                864
Val Ser Arg Asp Gly Ala Ile Leu Lys Ala Gly Val Asp Val Ser Ile
                595                 600                 605

AAC AAA AAC GCC GTC CTG TCC CTT GGC TAC GGC GGG CAG CTG TCG TCC                912
Asn Lys Asn Ala Val Leu Ser Leu Gly Tyr Gly Gly Gln Leu Ser Ser
                610                 615                 620

AAC CAC CAG GAC AAC AGC GTC AAC GCC GGT CTG ACC TGG CGC TTC                    957
Asn His Gln Asp Asn Ser Val Asn Ala Gly Leu Thr Trp Arg Phe
625                 630                 635

(2) INFORMATION FOR SEQ ID NO: 33:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 33:

Thr Arg Gln Leu Ser Gly Gln Ile His Ala Asp Met Ala Ser Ala Gln
 1               5                  10                  15

Ile Asn Glu Ser Arg Tyr Leu Arg Asp Thr Ala Thr Glu Arg Leu Arg
                20                  25                  30

Gln Ala Glu Gly Arg Arg Thr Ala Thr Asp Ile Lys Ala Asp Asp Asn
            35                  40                  45

Gly Ala Trp Ala Lys Leu Leu Gly Ser Trp Gly His Ala Ser Gly Asn
     50                  55                  60

Asp Asn Ala Thr Gly Tyr Gln Thr Ser Thr Tyr Gly Val Leu Leu Gly
65                  70                  75                  80

Leu Asp Ser Glu Leu Phe Gly Asp Gly Arg Leu Gly Met Met Thr Gly
                85                  90                  95

Tyr Thr Arg Thr Ser Leu Asp Gly Gly Tyr Gln Ser Asp Ala His Ser
            100                 105                 110

Asp Asn Tyr His Leu Gly Leu Tyr Gly Asp Lys Arg Phe Gly Ala Leu
        115                 120                 125

Ala Leu Arg Ala Gly Gly Thr Tyr Thr Trp His Arg Ile Asp Thr Ser
    130                 135                 140

Arg Ser Val Asn Tyr Gly Ala Gln Ser Asp Arg Glu Lys Ala Lys Tyr
145                 150                 155                 160
```

```
Asn Ala Arg Thr Gly Gln Leu Phe Ile Glu Ser Gly Tyr Asp Trp Thr
            165                 170                 175

Ser Asp Ala Val Asn Leu Glu Pro Phe Ala Asn Leu Ala Tyr Thr His
            180                 185                 190

Tyr Arg Asn Glu Glu Ile Asn Glu Gln Gly Gly Ala Ala Ala Leu Arg
            195                 200                 205

Gly Asp Lys Gln Ser Gln Ser Ala Thr Ala Ser Thr Leu Gly Leu Arg
            210                 215                 220

Ala Asp Thr Glu Trp Gln Thr Asp Ser Val Ala Ile Ala Leu Arg Gly
225                 230                 235                 240

Glu Leu Gly Trp Gln His Gln Tyr Gly Lys Leu Glu Arg Lys Thr Gln
            245                 250                 255

Leu Met Phe Lys Arg Thr Asp Ala Ala Phe Asp Val Asn Ser Val Pro
            260                 265                 270

Val Ser Arg Asp Gly Ala Ile Leu Lys Ala Gly Val Asp Val Ser Ile
            275                 280                 285

Asn Lys Asn Ala Val Leu Ser Leu Gly Tyr Gly Gly Gln Leu Ser Ser
            290                 295                 300

Asn His Gln Asp Asn Ser Val Asn Ala Gly Leu Thr Trp Arg Phe
305                 310                 315
```

(2) INFORMATION FOR SEQ ID NO: 34:

(i) SEQUENCE CHARACTERISTICS:
        (A) LENGTH: 960 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..960

(xi) SEQUENCE DESCRIPTION: SEQ ID NO: 34:

```
TTC CGT CAG CTG TCG GGG CAA ATC CAT GCG GAC ATC GCG TCG GCG CTG      48
Phe Arg Gln Leu Ser Gly Gln Ile His Ala Asp Ile Ala Ser Ala Leu
320                 325                 330                 335

GTG AAC GAC AGC CGC TAC CTG CGT GAG GCG CTG AAC GGG CGT CTG CGT      96
Val Asn Asp Ser Arg Tyr Leu Arg Glu Ala Leu Asn Gly Arg Leu Arg
            340                 345                 350

CAG GCG GAA GGG CTG GCG AGC TCG TCG GCC ATC AAG GCG GAC GAG GAC     144
Gln Ala Glu Gly Leu Ala Ser Ser Ser Ala Ile Lys Ala Asp Glu Asp
            355                 360                 365

GGC GCC TGG GCG CAG CTG CTG GGA GCG TGG GAC CAT GCG TCG GGC GAC     192
Gly Ala Trp Ala Gln Leu Leu Gly Ala Trp Asp His Ala Ser Gly Asp
            370                 375                 380

GCC AAC GCC ACC GGC TAT CAG GCC TCG ACC TAC GGG GTG CTG GTG GGG     240
Ala Asn Ala Thr Gly Tyr Gln Ala Ser Thr Tyr Gly Val Leu Val Gly
385                 390                 395

CTG GAC TCG GCG GCG GCG GCC GAC TGG CGG CTG GGG GTG GCG ACC GGC     288
Leu Asp Ser Ala Ala Ala Ala Asp Trp Arg Leu Gly Val Ala Thr Gly
400                 405                 410                 415

TAC ACC CGC ACC TCG CTG CAC GGC GGG TAT GGG TCG AAG GCG GAC AGC     336
Tyr Thr Arg Thr Ser Leu His Gly Gly Tyr Gly Ser Lys Ala Asp Ser
            420                 425                 430

GAC AAC TAC CAC CTG GCG GCG TAC GGC GAC AAG CAG TTC GGG GCG CTG     384
Asp Asn Tyr His Leu Ala Ala Tyr Gly Asp Lys Gln Phe Gly Ala Leu
            435                 440                 445

GCG CTG CGG GGC GGG GCG GGC TAC ACC TGG CAC CGC ATC GAC ACC AAG     432
```

```
Ala Leu Arg Gly Gly Ala Gly Tyr Thr Trp His Arg Ile Asp Thr Lys
        450                 455                 460

CGG TCG GTG AAC TAC GGG ATG CAG TCG GAC CGC GAC ACG GCG AAG TAC      480
Arg Ser Val Asn Tyr Gly Met Gln Ser Asp Arg Asp Thr Ala Lys Tyr
    465                 470                 475

AGC GCG CGC ACC GAG CAG CTG TTC GCG GAA GCG GGC TAC AGC GTG AAG      528
Ser Ala Arg Thr Glu Gln Leu Phe Ala Glu Ala Gly Tyr Ser Val Lys
480                 485                 490                 495

GGC GAG TGG CTG AAC CTG GAG CCG TTC GTC AAC CTG GCG TAC GTG AAC      576
Gly Glu Trp Leu Asn Leu Glu Pro Phe Val Asn Leu Ala Tyr Val Asn
                500                 505                 510

TTT GAA AAC AAC GGC ATC GCG GAA AGC GGC GGC GCA GCG GCG CTG CGC      624
Phe Glu Asn Asn Gly Ile Ala Glu Ser Gly Gly Ala Ala Ala Leu Arg
            515                 520                 525

GGC GAC AAG CAG CAC ACC GAC GCG ACG GTG TCG ACG CTG GGA CTG CGC      672
Gly Asp Lys Gln His Thr Asp Ala Thr Val Ser Thr Leu Gly Leu Arg
        530                 535                 540

GCG GAC ACT GAG TGG CAG GTG AGC CCG GGC ACG ACG GTG GCG CTG CGC      720
Ala Asp Thr Glu Trp Gln Val Ser Pro Gly Thr Thr Val Ala Leu Arg
    545                 550                 555

AGC GAG CTG GGG TGG CAA CAC CAG TAC GGC GGG CTG GAG CGT GGC ACC      768
Ser Glu Leu Gly Trp Gln His Gln Tyr Gly Gly Leu Glu Arg Gly Thr
560                 565                 570                 575

GGG CTG CGG TTC AAC GGC GGC AAC GCG CCG TTC GTG GTG GAC AGC GTG      816
Gly Leu Arg Phe Asn Gly Gly Asn Ala Pro Phe Val Val Asp Ser Val
                580                 585                 590

CCG GTG TCG CGC GAC GGG ATG GTG CTG AAG GCG GGT GCG GAA GTG GCG      864
Pro Val Ser Arg Asp Gly Met Val Leu Lys Ala Gly Ala Glu Val Ala
            595                 600                 605

GTG AAC GAG AAC GCC TCG CTG TCG CTG GGC TAC GGC GGG CTG CTG TCG      912
Val Asn Glu Asn Ala Ser Leu Ser Leu Gly Tyr Gly Gly Leu Leu Ser
        610                 615                 620

CAG AAC CAT CAG GAC AAC AGC GTC AAC GCC GGC TTC ACC TGG CGC TTC      960
Gln Asn His Gln Asp Asn Ser Val Asn Ala Gly Phe Thr Trp Arg Phe
    625                 630                 635
```

(2) INFORMATION FOR SEQ ID NO: 35:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO: 35:

```
Phe Arg Gln Leu Ser Gly Gln Ile His Ala Asp Ile Ala Ser Ala Leu
 1               5                  10                  15

Val Asn Asp Ser Arg Tyr Leu Arg Glu Ala Leu Asn Gly Arg Leu Arg
            20                  25                  30

Gln Ala Glu Gly Leu Ala Ser Ser Ala Ile Lys Ala Asp Glu Asp
        35                  40                  45

Gly Ala Trp Ala Gln Leu Leu Gly Ala Trp Asp His Ala Ser Gly Asp
    50                  55                  60

Ala Asn Ala Thr Gly Tyr Gln Ala Ser Thr Tyr Gly Val Leu Val Gly
65                  70                  75                  80

Leu Asp Ser Ala Ala Ala Asp Trp Arg Leu Gly Val Ala Thr Gly
            85                  90                  95

Tyr Thr Arg Thr Ser Leu His Gly Gly Tyr Gly Ser Lys Ala Asp Ser
            100                 105                 110
```

```
Asp Asn Tyr His Leu Ala Ala Tyr Gly Asp Lys Gln Phe Gly Ala Leu
        115                 120                 125

Ala Leu Arg Gly Gly Ala Gly Tyr Thr Trp His Arg Ile Asp Thr Lys
130                 135                 140

Arg Ser Val Asn Tyr Gly Met Gln Ser Asp Arg Asp Thr Ala Lys Tyr
145                 150                 155                 160

Ser Ala Arg Thr Glu Gln Leu Phe Ala Glu Ala Gly Tyr Ser Val Lys
                165                 170                 175

Gly Glu Trp Leu Asn Leu Glu Pro Phe Val Asn Leu Ala Tyr Val Asn
            180                 185                 190

Phe Glu Asn Asn Gly Ile Ala Glu Ser Gly Gly Ala Ala Leu Arg
        195                 200                 205

Gly Asp Lys Gln His Thr Asp Ala Thr Val Ser Thr Leu Gly Leu Arg
    210                 215                 220

Ala Asp Thr Glu Trp Gln Val Ser Pro Gly Thr Thr Val Ala Leu Arg
225                 230                 235                 240

Ser Glu Leu Gly Trp Gln His Gln Tyr Gly Gly Leu Glu Arg Gly Thr
                245                 250                 255

Gly Leu Arg Phe Asn Gly Gly Asn Ala Pro Phe Val Val Asp Ser Val
            260                 265                 270

Pro Val Ser Arg Asp Gly Met Val Leu Lys Ala Gly Ala Glu Val Ala
        275                 280                 285

Val Asn Glu Asn Ala Ser Leu Ser Leu Gly Tyr Gly Gly Leu Leu Ser
    290                 295                 300

Gln Asn His Gln Asp Asn Ser Val Asn Ala Gly Phe Thr Trp Arg Phe
305                 310                 315                 320

(2) INFORMATION FOR SEQ ID NO: 36:

(i) SEQUENCE CHARACTERISTICS:
        (A) LENGTH: 960 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..960

(xi) SEQUENCE DESCRIPTION: SEQ ID NO: 36:

TTC CGT CAG CTG TCG GGG CAA ATC CAT GCG GAC ATC GCG TCG GCG CTG       48
Phe Arg Gln Leu Ser Gly Gln Ile His Ala Asp Ile Ala Ser Ala Leu
                325                 330                 335

GTG AAC GAC AGC CGC TAC CTG CGT GAG GCG CTG AAC GGG CGT CTG CGT       96
Val Asn Asp Ser Arg Tyr Leu Arg Glu Ala Leu Asn Gly Arg Leu Arg
            340                 345                 350

CAG GCG GAA GGG CTG GCG AGC TCG TCG GCC ATC AAG GCG GAC GAG GAC      144
Gln Ala Glu Gly Leu Ala Ser Ser Ser Ala Ile Lys Ala Asp Glu Asp
        355                 360                 365

GGC GCC TGG GCG CAG CTG CTG GGA GCG TGG GAC CAT GCG TCG GGC GAC      192
Gly Ala Trp Ala Gln Leu Leu Gly Ala Trp Asp His Ala Ser Gly Asp
    370                 375                 380

GCC AAC GCC ACC GGC TAT CAG GCC TCG ACC TAC GGG GTG CTG GTG GGG      240
Ala Asn Ala Thr Gly Tyr Gln Ala Ser Thr Tyr Gly Val Leu Val Gly
385                 390                 395                 400

CTG GAC TCG GCG GCG GCG GCC GAC TGG CGG CTG GGG GTG GCG ACC GGC      288
Leu Asp Ser Ala Ala Ala Ala Asp Trp Arg Leu Gly Val Ala Thr Gly
                405                 410                 415
```

| | | |
|---|---|---|
| TAC ACC CGC ACC TCG CTG CAC GGC GGG TAT GGG TCG AAG GCG GAC AGC<br>Tyr Thr Arg Thr Ser Leu His Gly Gly Tyr Gly Ser Lys Ala Asp Ser<br>420 425 430 | | 336 |
| GAC AAC TAC CAC CTG GCG GCG TAC GGC GAC AAG CAG TTC GGG GCG CTG<br>Asp Asn Tyr His Leu Ala Ala Tyr Gly Asp Lys Gln Phe Gly Ala Leu<br>435 440 445 | | 384 |
| GCG CTG CGG GGC GGG GCG GGC TAC ACC TGG CAC CGC ATC GAC ACC AAG<br>Ala Leu Arg Gly Gly Ala Gly Tyr Thr Trp His Arg Ile Asp Thr Lys<br>450 455 460 | | 432 |
| CGG TCG GTG AAC TAC GGG ATG CAG TCG GAC CGC GAC ACG GCG AAG TAC<br>Arg Ser Val Asn Tyr Gly Met Gln Ser Asp Arg Asp Thr Ala Lys Tyr<br>465 470 475 480 | | 480 |
| AGC GCG CGC ACC GAG CAG CTG TTC GCG GAA GCG GGC TAC AGC GTG AAG<br>Ser Ala Arg Thr Glu Gln Leu Phe Ala Glu Ala Gly Tyr Ser Val Lys<br>485 490 495 | | 528 |
| GGC GAG TGG CTG AAC CTG GAG CCG TTC GTC AAC CTG GCG TAC GTG AAC<br>Gly Glu Trp Leu Asn Leu Glu Pro Phe Val Asn Leu Ala Tyr Val Asn<br>500 505 510 | | 576 |
| TTT GAA AAC AAC GGC ATC GCG GAA AGC GGC GGC GCA GCG GCG CTG CGC<br>Phe Glu Asn Asn Gly Ile Ala Glu Ser Gly Gly Ala Ala Ala Leu Arg<br>515 520 525 | | 624 |
| GGC GAC AAG CAG CAC ACC GAC GCG ACG GTG TCG ACG CTG GGA CTG CGC<br>Gly Asp Lys Gln His Thr Asp Ala Thr Val Ser Thr Leu Gly Leu Arg<br>530 535 540 | | 672 |
| GCG GAC ACT GAG TGG CAG GTG AGC CCG GGC ACG ACG GTG GCG CTG CGC<br>Ala Asp Thr Glu Trp Gln Val Ser Pro Gly Thr Thr Val Ala Leu Arg<br>545 550 555 560 | | 720 |
| AGC GAG CTG GGG TGG CAA CAC CAG TAC GGC GGG CTG GAG CGT GGC ACC<br>Ser Glu Leu Gly Trp Gln His Gln Tyr Gly Gly Leu Glu Arg Gly Thr<br>565 570 575 | | 768 |
| GGG CTG CGG TTC AAC GGC GGC AAC GCG CCG TTC GTG GTG GAC AGC GTG<br>Gly Leu Arg Phe Asn Gly Gly Asn Ala Pro Phe Val Val Asp Ser Val<br>580 585 590 | | 816 |
| CCG GTG TCG CGC GAC GGG ATG GTG CTG AAG GCG GGT GCG GAA GTG GCG<br>Pro Val Ser Arg Asp Gly Met Val Leu Lys Ala Gly Ala Glu Val Ala<br>595 600 605 | | 864 |
| GTG AAC GAG AAC GCC TCG CTG TCG CTG GGC TAC GGC GGG CTG CTG TCG<br>Val Asn Glu Asn Ala Ser Leu Ser Leu Gly Tyr Gly Gly Leu Leu Ser<br>610 615 620 | | 912 |
| CAG AAC CAT CAG GAC AAC AGC GTC AAC GCC GGC TTC ACC TGG CGC TTC<br>Gln Asn His Gln Asp Asn Ser Val Asn Ala Gly Phe Thr Trp Arg Phe<br>625 630 635 640 | | 960 |

(2) INFORMATION FOR SEQ ID NO: 37:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO: 37:

Phe Arg Gln Leu Ser Gly Gln Ile His Ala Asp Ile Ala Ser Ala Leu
1               5                   10                  15

Val Asn Asp Ser Arg Tyr Leu Arg Glu Ala Leu Asn Gly Arg Leu Arg
                20                  25                  30

Gln Ala Glu Gly Leu Ala Ser Ser Ala Ile Lys Ala Asp Glu Asp
            35                  40                  45

Gly Ala Trp Ala Gln Leu Leu Gly Ala Trp Asp His Ala Ser Gly Asp
        50                  55                  60

```
Ala Asn Ala Thr Gly Tyr Gln Ala Ser Thr Tyr Gly Val Leu Val Gly
 65                  70                  75                  80

Leu Asp Ser Ala Ala Ala Asp Trp Arg Leu Gly Val Ala Thr Gly
                 85                  90                  95

Tyr Thr Arg Thr Ser Leu His Gly Gly Tyr Gly Ser Lys Ala Asp Ser
                100                 105                 110

Asp Asn Tyr His Leu Ala Ala Tyr Gly Asp Lys Gln Phe Gly Ala Leu
            115                 120                 125

Ala Leu Arg Gly Gly Ala Gly Tyr Thr Trp His Arg Ile Asp Thr Lys
130                 135                 140

Arg Ser Val Asn Tyr Gly Met Gln Ser Asp Arg Asp Thr Ala Lys Tyr
145                 150                 155                 160

Ser Ala Arg Thr Glu Gln Leu Phe Ala Glu Ala Gly Tyr Ser Val Lys
                165                 170                 175

Gly Glu Trp Leu Asn Leu Glu Pro Phe Val Asn Leu Ala Tyr Val Asn
                180                 185                 190

Phe Glu Asn Asn Gly Ile Ala Glu Ser Gly Gly Ala Ala Leu Arg
            195                 200                 205

Gly Asp Lys Gln His Thr Asp Ala Thr Val Ser Thr Leu Gly Leu Arg
210                 215                 220

Ala Asp Thr Glu Trp Gln Val Ser Pro Gly Thr Val Ala Leu Arg
225                 230                 235                 240

Ser Glu Leu Gly Trp Gln His Gln Tyr Gly Gly Leu Glu Arg Gly Thr
                245                 250                 255

Gly Leu Arg Phe Asn Gly Gly Asn Ala Pro Phe Val Val Asp Ser Val
                260                 265                 270

Pro Val Ser Arg Asp Gly Met Val Leu Lys Ala Gly Ala Glu Val Ala
                275                 280                 285

Val Asn Glu Asn Ala Ser Leu Ser Leu Gly Tyr Gly Gly Leu Leu Ser
                290                 295                 300

Gln Asn His Gln Asp Asn Ser Val Asn Ala Gly Phe Thr Trp Arg Phe
305                 310                 315                 320

(2) INFORMATION FOR SEQ ID NO: 38:

(i) SEQUENCE CHARACTERISTICS:
        (A) LENGTH: 798 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..798

(xi) SEQUENCE DESCRIPTION: SEQ ID NO: 38:

ATT AAT GGC GAA GCC GGT ACG TGG GTG CGT CTG CTG AAC GGT TCC GGC       48
Ile Asn Gly Glu Ala Gly Thr Trp Val Arg Leu Leu Asn Gly Ser Gly
                325                 330                 335

TCT GCT GAT GGC GGT TTC ACT GAC CAC TAT ACC CTG CTG CAG ATG GGG      96
Ser Ala Asp Gly Gly Phe Thr Asp His Tyr Thr Leu Leu Gln Met Gly
            340                 345                 350

GCT GAC CGT AAG CAC GAA CTG GGA AGT ATG GAC CTG TTT ACC GGC GTG     144
Ala Asp Arg Lys His Glu Leu Gly Ser Met Asp Leu Phe Thr Gly Val
        355                 360                 365

ATG GCC ACC TAC ACT GAC ACA GAT GCG TCA GCA GAC CTG TAC AGC GGT     192
Met Ala Thr Tyr Thr Asp Thr Asp Ala Ser Ala Asp Leu Tyr Ser Gly
370                 375                 380
```

```
AAA ACA AAA TCA TGG GGT GGT GGT TTC TAT GCC AGT GGT CTG TTC CGG       240
Lys Thr Lys Ser Trp Gly Gly Gly Phe Tyr Ala Ser Gly Leu Phe Arg
385                 390                 395                 400

TCC GGC GCT TAC TTT GAT GTG ATT GCC AAA TAT ATT CAC AAT GAA AAC       288
Ser Gly Ala Tyr Phe Asp Val Ile Ala Lys Tyr Ile His Asn Glu Asn
                405                 410                 415

AAA TAT GAC CTG AAC TTT GCC GGA GCT GGT AAA CAG AAC TTC CGC AGC       336
Lys Tyr Asp Leu Asn Phe Ala Gly Ala Gly Lys Gln Asn Phe Arg Ser
            420                 425                 430

CAT TCA CTG TAT GCA GGT GCA GAA GTC GGA TAC CGT TAT CAT CTG ACA       384
His Ser Leu Tyr Ala Gly Ala Glu Val Gly Tyr Arg Tyr His Leu Thr
        435                 440                 445

GAT ACG ACG TTT GTT GAA CCT CAG GCG GAA CTG GTC TGG GGA AGA CTG       432
Asp Thr Thr Phe Val Glu Pro Gln Ala Glu Leu Val Trp Gly Arg Leu
450                 455                 460

CAG GGC CAA ACA TTT AAC TGG AAC GAC AGT GGA ATG GAT GTC TCA ATG       480
Gln Gly Gln Thr Phe Asn Trp Asn Asp Ser Gly Met Asp Val Ser Met
465                 470                 475                 480

CGT CGT AAC AGC GTT AAT CCT CTG GTA GGC AGA ACC GGC GTT GTT TCC       528
Arg Arg Asn Ser Val Asn Pro Leu Val Gly Arg Thr Gly Val Val Ser
                485                 490                 495

GGT AAA ACC TTC AGT GGT AAG GAC TGG AGT CTG ACA GCC CGT GCC GGC       576
Gly Lys Thr Phe Ser Gly Lys Asp Trp Ser Leu Thr Ala Arg Ala Gly
            500                 505                 510

CTG CAT TAT GAG TTC GAT CTG ACG GAC AGT GCT GAC GTT CAT CTG AAG       624
Leu His Tyr Glu Phe Asp Leu Thr Asp Ser Ala Asp Val His Leu Lys
        515                 520                 525

GAT GCA GCG GGA GAA CAT CAG ATT AAT GGC AGA AAA GAC AGT CGT ATG       672
Asp Ala Ala Gly Glu His Gln Ile Asn Gly Arg Lys Asp Ser Arg Met
530                 535                 540

CTT TAC GGT GTG GGG TTA AAT GCC CGG TTT GGC GAC AAT ACG CGT TTG       720
Leu Tyr Gly Val Gly Leu Asn Ala Arg Phe Gly Asp Asn Thr Arg Leu
545                 550                 555                 560

GGG CTG GAA GTT GAA CGC TCT GCA TTT GGT AAA TAC AAC ACA GAT GAT       768
Gly Leu Glu Val Glu Arg Ser Ala Phe Gly Lys Tyr Asn Thr Asp Asp
                565                 570                 575

GCG ATA AAC GCT AAT ATT CGT TAT TCA TTC                               798
Ala Ile Asn Ala Asn Ile Arg Tyr Ser Phe
            580                 585
```

(2) INFORMATION FOR SEQ ID NO: 39:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO: 39:

```
Ile Asn Gly Glu Ala Gly Thr Trp Val Arg Leu Leu Asn Gly Ser Gly
1               5                   10                  15

Ser Ala Asp Gly Gly Phe Thr Asp His Tyr Thr Leu Leu Gln Met Gly
            20                  25                  30

Ala Asp Arg Lys His Glu Leu Gly Ser Met Asp Leu Phe Thr Gly Val
        35                  40                  45

Met Ala Thr Tyr Thr Asp Thr Asp Ala Ser Ala Asp Leu Tyr Ser Gly
    50                  55                  60

Lys Thr Lys Ser Trp Gly Gly Gly Phe Tyr Ala Ser Gly Leu Phe Arg
65                  70                  75                  80
```

```
Ser Gly Ala Tyr Phe Asp Val Ile Ala Lys Tyr Ile His Asn Glu Asn
                85                  90                  95

Lys Tyr Asp Leu Asn Phe Ala Gly Ala Gly Lys Gln Asn Phe Arg Ser
            100                 105                 110

His Ser Leu Tyr Ala Gly Ala Glu Val Gly Tyr Arg Tyr His Leu Thr
        115                 120                 125

Asp Thr Thr Phe Val Glu Pro Gln Ala Glu Leu Val Trp Gly Arg Leu
    130                 135                 140

Gln Gly Gln Thr Phe Asn Trp Asn Asp Ser Gly Met Asp Val Ser Met
145                 150                 155                 160

Arg Arg Asn Ser Val Asn Pro Leu Val Gly Arg Thr Gly Val Val Ser
                165                 170                 175

Gly Lys Thr Phe Ser Gly Lys Asp Trp Ser Leu Thr Ala Arg Ala Gly
            180                 185                 190

Leu His Tyr Glu Phe Asp Leu Thr Asp Ser Ala Asp Val His Leu Lys
        195                 200                 205

Asp Ala Ala Gly Glu His Gln Ile Asn Gly Arg Lys Asp Ser Arg Met
    210                 215                 220

Leu Tyr Gly Val Gly Leu Asn Ala Arg Phe Gly Asp Asn Thr Arg Leu
225                 230                 235                 240

Gly Leu Glu Val Glu Arg Ser Ala Phe Gly Lys Tyr Asn Thr Asp Asp
                245                 250                 255

Ala Ile Asn Ala Asn Ile Arg Tyr Ser Phe
            260                 265

(2) INFORMATION FOR SEQ ID NO: 40:

(i) SEQUENCE CHARACTERISTICS:
        (A) LENGTH: 864 base pairs
        (B) TYPE: nucleic acid
        (C) STRANDEDNESS: both
        (D) TOPOLOGY: linear (ix) FEATURE:
        (A) NAME/KEY: CDS
        (B) LOCATION:1..864

(xi) SEQUENCE DESCRIPTION: SEQ ID NO: 40:

TCT TTA GAA AGC GCG GCG GAA GTG TTG TAT CAA TTT GCC CCT AAA TAT       48
Ser Leu Glu Ser Ala Ala Glu Val Leu Tyr Gln Phe Ala Pro Lys Tyr
            270                 275                 280

GAA AAA CCC ACC AAT GTT TGG GCT AAC GCT ATT GGG GGA ACG AGC TTG       96
Glu Lys Pro Thr Asn Val Trp Ala Asn Ala Ile Gly Gly Thr Ser Leu
        285                 290                 295

AAT AGT GGC GGT AAC GCT TCA TTG TAT GGC ACA AGT GCG GGC GTA GAT      144
Asn Ser Gly Gly Asn Ala Ser Leu Tyr Gly Thr Ser Ala Gly Val Asp
    300                 305                 310

GCT TAC CTT AAC GGG GAA GTG GAA GCC ATT GTG GGC GGT TTT GGA AGC      192
Ala Tyr Leu Asn Gly Glu Val Glu Ala Ile Val Gly Gly Phe Gly Ser
315                 320                 325                 330

TAT GGT TAT AGC TCC TTT AGT AAT CAA GCG AAC TCT CTT AAC TCT GGG      240
Tyr Gly Tyr Ser Ser Phe Ser Asn Gln Ala Asn Ser Leu Asn Ser Gly
                335                 340                 345

GCC AAT AAC ACT AAT TTT GGC GTG TAT AGC CGT ATT TTT GCT AAC CAG      288
Ala Asn Asn Thr Asn Phe Gly Val Tyr Ser Arg Ile Phe Ala Asn Gln
            350                 355                 360

CAT GAA TTT GAC TTT GAA GCT CAA GGG GCG CTA GGG AGT GAT CAA TCA      336
His Glu Phe Asp Phe Glu Ala Gln Gly Ala Leu Gly Ser Asp Gln Ser
        365                 370                 375
```

-continued

```
AGC TTG AAT TTC AAA AGC GCT TTA TTG CGA GAT TTG AAT CAA AGC TAT         384
Ser Leu Asn Phe Lys Ser Ala Leu Leu Arg Asp Leu Asn Gln Ser Tyr
380                 385                 390

AAT TAC TTA GCC TAT AGC GCT GCA ACA AGA GCG AGC TAT GGT TAT GAC         432
Asn Tyr Leu Ala Tyr Ser Ala Ala Thr Arg Ala Ser Tyr Gly Tyr Asp
395                 400                 405                 410

TTC GCG TTT TTT AGG AAC GCT TTG GTG TTA AAA CCA AGC GTG GGC GTG         480
Phe Ala Phe Phe Arg Asn Ala Leu Val Leu Lys Pro Ser Val Gly Val
            415                 420                 425

AGC TAT AAC CAT TTA GGT TCA ACC AAC TTT AAA AGC AAC AGC AAT CAA         528
Ser Tyr Asn His Leu Gly Ser Thr Asn Phe Lys Ser Asn Ser Asn Gln
                430                 435                 440

AAA GTG GCT TTG AAA AAT GGT GCA AGC AGT CAG CAT TTA TTC AAC GCT         576
Lys Val Ala Leu Lys Asn Gly Ala Ser Ser Gln His Leu Phe Asn Ala
                    445                 450                 455

AGT GCT AAT GTG GAA GCG CGC TAT TAT TAT GGG GAC ACT TCA TAC TTC         624
Ser Ala Asn Val Glu Ala Arg Tyr Tyr Tyr Gly Asp Thr Ser Tyr Phe
460                 465                 470

TAC ATG AAC GCT GGA GTT TTA CAA GAG TTC GCT AAC TTT GGT TCT AGC         672
Tyr Met Asn Ala Gly Val Leu Gln Glu Phe Ala Asn Phe Gly Ser Ser
475                 480                 485                 490

AAT GCG GTG TCT TTA AAC ACC TTT AAA GTG AAT GCT ACT CGT AAC CCT         720
Asn Ala Val Ser Leu Asn Thr Phe Lys Val Asn Ala Thr Arg Asn Pro
            495                 500                 505

TTA AAT ACC CAT GCG AGA GTG ATG ATG GGT GGG GAA TTA AAA TTA GCT         768
Leu Asn Thr His Ala Arg Val Met Met Gly Gly Glu Leu Lys Leu Ala
                510                 515                 520

AAA GAA GTG TTT TTG AAT TTG GGC TTT GTT TAT TTG CAC AAT TTG ATT         816
Lys Glu Val Phe Leu Asn Leu Gly Phe Val Tyr Leu His Asn Leu Ile
                    525                 530                 535

TCC AAT ATA GGC CAT TTC GCT TCC AAT TTA GGA ATG AGG TAT AGT TTC         864
Ser Asn Ile Gly His Phe Ala Ser Asn Leu Gly Met Arg Tyr Ser Phe
540                 545                 550
```

(2) INFORMATION FOR SEQ ID NO: 41:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO: 41:

```
Ser Leu Glu Ser Ala Ala Glu Val Leu Tyr Gln Phe Ala Pro Lys Tyr
1               5                   10                  15

Glu Lys Pro Thr Asn Val Trp Ala Asn Ala Ile Gly Gly Thr Ser Leu
            20                  25                  30

Asn Ser Gly Gly Asn Ala Ser Leu Tyr Gly Thr Ser Ala Gly Val Asp
        35                  40                  45

Ala Tyr Leu Asn Gly Glu Val Glu Ala Ile Val Gly Phe Gly Ser
    50                  55                  60

Tyr Gly Tyr Ser Ser Phe Ser Asn Gln Ala Asn Ser Leu Asn Ser Gly
65                  70                  75                  80

Ala Asn Asn Thr Asn Phe Gly Val Tyr Ser Arg Ile Phe Ala Asn Gln
                85                  90                  95

His Glu Phe Asp Phe Glu Ala Gln Gly Ala Leu Gly Ser Asp Gln Ser
            100                 105                 110

Ser Leu Asn Phe Lys Ser Ala Leu Leu Arg Asp Leu Asn Gln Ser Tyr
```

-continued

```
                     115                 120                 125
Asn Tyr Leu Ala Tyr Ser Ala Ala Thr Arg Ala Ser Tyr Gly Tyr Asp
        130                 135                 140

Phe Ala Phe Phe Arg Asn Ala Leu Val Leu Lys Pro Ser Val Gly Val
145                 150                 155                 160

Ser Tyr Asn His Leu Gly Ser Thr Asn Phe Lys Ser Asn Ser Asn Gln
                165                 170                 175

Lys Val Ala Leu Lys Asn Gly Ala Ser Ser Gln His Leu Phe Asn Ala
                180                 185                 190

Ser Ala Asn Val Glu Ala Arg Tyr Tyr Tyr Gly Asp Thr Ser Tyr Phe
        195                 200                 205

Tyr Met Asn Ala Gly Val Leu Gln Glu Phe Ala Asn Phe Gly Ser Ser
        210                 215                 220

Asn Ala Val Ser Leu Asn Thr Phe Lys Val Asn Ala Thr Arg Asn Pro
225                 230                 235                 240

Leu Asn Thr His Ala Arg Val Met Met Gly Gly Glu Leu Lys Leu Ala
                245                 250                 255

Lys Glu Val Phe Leu Asn Leu Gly Phe Val Tyr Leu His Asn Leu Ile
                260                 265                 270

Ser Asn Ile Gly His Phe Ala Ser Asn Leu Gly Met Arg Tyr Ser Phe
            275                 280                 285
```